(12) United States Patent
Chun et al.

(10) Patent No.: US 12,371,736 B2
(45) Date of Patent: Jul. 29, 2025

(54) TD PROBE AND ITS USES

(71) Applicant: SEEGENE, INC., Seoul (KR)

(72) Inventors: Jong Yoon Chun, Seoul (KR); In Taek Hwang, Seoul (KR); Sang Kil Lee, Seoul (KR)

(73) Assignee: SEEGENE, INC., Seoul (KR)

( * ) Notice: Subject to any disclaimer, the term of this patent is extended or adjusted under 35 U.S.C. 154(b) by 34 days.

(21) Appl. No.: 15/599,948

(22) Filed: May 19, 2017

(65) Prior Publication Data

US 2017/0260576 A1 Sep. 14, 2017

Related U.S. Application Data

(63) Continuation-in-part of application No. 13/392,400, filed as application No. PCT/KR2010/005971 on Sep. 2, 2010, now abandoned.

(30) Foreign Application Priority Data

Sep. 3, 2009 (KR) .......................... 1020090083196
Jun. 24, 2010 (WO) ................ PCT/KR2010/004119

(51) Int. Cl.
| | | |
|---|---|---|
| *C12Q 1/6813* | (2018.01) | |
| *C12Q 1/6818* | (2018.01) | |
| *C12Q 1/6827* | (2018.01) | |
| *C12Q 1/6832* | (2018.01) | |
| *C12Q 1/686* | (2018.01) | |
| *C07H 21/00* | (2006.01) | |

(52) U.S. Cl.
CPC ......... *C12Q 1/6832* (2013.01); *C12Q 1/6818* (2013.01); *C12Q 1/6827* (2013.01); *C12Q 1/686* (2013.01)

(58) Field of Classification Search
None
See application file for complete search history.

(56) References Cited

U.S. PATENT DOCUMENTS

| | | | | | |
|---|---|---|---|---|---|
| 5,508,168 | A * | 4/1996 | Orle | .................. | C12Q 1/705 435/6.15 |
| 5,928,907 | A * | 7/1999 | Woudenberg | ........ | G01N 21/645 422/82.07 |
| 6,130,073 | A * | 10/2000 | Eggerding | ........... | C12Q 1/6846 435/6.12 |
| 7,320,860 | B2 * | 1/2008 | Landegren | ........... | C12Q 1/6848 435/6.12 |
| 9,885,081 | B2 * | 2/2018 | Chun | .................. | C12Q 1/6818 |
| 2002/0164661 | A1 | 11/2002 | Clinton et al. | | |
| 2002/0182602 | A1 * | 12/2002 | Woo | ...................... | C07H 21/04 435/6.12 |
| 2003/0175749 | A1 * | 9/2003 | Chun | .................. | C12Q 1/6876 435/6.14 |
| 2005/0222403 | A1 * | 10/2005 | Lyles | .................. | C12Q 1/6818 435/6.14 |
| 2007/0292861 | A1 * | 12/2007 | Thompson | ........... | C12Q 1/6816 435/6.12 |
| 2009/0099786 | A1 * | 4/2009 | Oliver | .................. | C12Q 1/6869 702/19 |
| 2009/0203013 | A1 * | 8/2009 | Jay | ......................... | C12Q 1/689 435/5 |
| 2010/0105120 | A1 * | 4/2010 | Zebala | .................. | C12N 13/00 536/24.5 |
| 2011/0020823 | A1 * | 1/2011 | Burns | .................... | C12Q 1/689 435/6.15 |
| 2012/0010086 | A1 * | 1/2012 | Froehlich | ........... | C12N 15/1096 506/26 |

FOREIGN PATENT DOCUMENTS

| | | | |
|---|---|---|---|
| WO | 199606190 A2 | 2/1996 | |
| WO | 2005078122 A2 | 8/2005 | |
| WO | 2006/095941 A1 | 9/2006 | |
| WO | 2006095981 A1 | 9/2006 | |
| WO | 2007/058499 A1 | 5/2007 | |
| WO | WO-2007115242 A2 * | 10/2007 | ........... C12Q 1/6816 |
| WO | 2008/051039 A1 | 5/2008 | |
| WO | 2008/111741 A1 | 9/2008 | |

OTHER PUBLICATIONS

"Viruses", Wikipedia.com, accessed Nov. 24, 2012. (Year: 2012).*
"How many species of bacteria are there", Wisegeek.com; accessed Jan. 21, 2014. (Year: 2014).*
"Fungi," Wikipedia.com; accessed Jun. 3, 2013. (Year: 2013).*
"Plant," Wikipedia.com; accessed Aug. 28, 2015. (Year: 2015).*
"Mammal," Wikipedia.com; accessed Sep. 22, 2011. (Year: 2011).*
"Murinae," Wikipedia.com, accessed Mar. 18, 2013. (Year: 2013).*
"Fish," Wikipedia.com, accessed Nov. 2, 2014. (Year: 2014).*
"Archaea," Wikipedia.com, accessed May 11, 2016. (Year: 2016).*
"Algae," Wikipedia.com, accessed Mar. 4, 2016. (Year: 2016).*
"Protozoa," Wikipedia.com, accessed May 11, 2016. (Year: 2016).*

(Continued)

*Primary Examiner* — Bradley L. Sisson
(74) *Attorney, Agent, or Firm* — Studebaker Brackett PLLC

(57) ABSTRACT

The present invention relates to a target discriminative probe (TD probe) and its uses or applications. The TD probe is hybridized with a target nucleic acid sequence through both of the 5'-second hybridization portion and the 3'-first hybridization portion. When the TD probe is hybridized with a non-target nucleic acid sequence, both the 5'-second hybridization portion and the separation portion are not hybridized with the non-target nucleic acid sequence such that both portions form a single strand due to its low Tm value. As such, the TD probe exhibits distinctly different hybridization patterns for each of the target and the non-target nucleic acid sequence, discriminating the target nucleic acid sequence from the non-target nucleic acid sequence with much higher specificity.

35 Claims, 19 Drawing Sheets
Specification includes a Sequence Listing.

(56) References Cited

OTHER PUBLICATIONS

Hwang et al., "Annealing control primer system for improving specificity of PCR amplification", BioTechniques, 35: 1180-1184, Dec. 2003. (Year: 2003).*
Parashar et al., "Applications of real-time PCR technology to mycobacterial research", Indian Journal of Medical Research, 124, Oct. 2006, 385-398. (Year: 2006).*
Kim et al., Annealing control primer system for identification of differentially expressed genes on agarose gels, BioTechniques, 36: 424-434, Mar. 2004. (Year: 2004).*
International Search Report, dated Jun. 28, 2011, issued in International Application No. PCT/KR2010/005971.
Keck, Michael V., et al.; Chemical and Structural Characterization of the Interaction of Bleomycin A2 with d (CGCGAATTCGCG)2. Efficient, Double-Strand DNA Cleavage Accessible without Structural Reorganization; J. Am. Chem. Soc. 2001, 123, 8690-8700.

* cited by examiner

Signal generation on target-specific hybridization

No signal on non-target hybridization

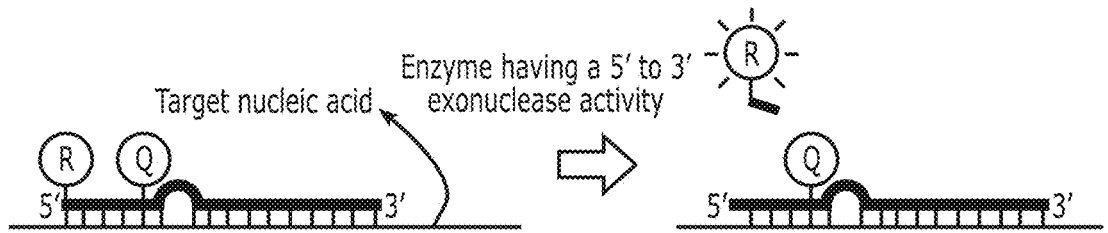

When a dual-labeled target discriminative (TD) probe is hybidized with a target nucleic acid sequence, the 5'-second hybridization portion of the TD probe is digested by an enzyme having a 5' to 3' exonuclease activity.

FIG. 2A

Signal generation on target-specific hybridization

- (R) : Reporter molecule
- (Q) : Quencher molecule

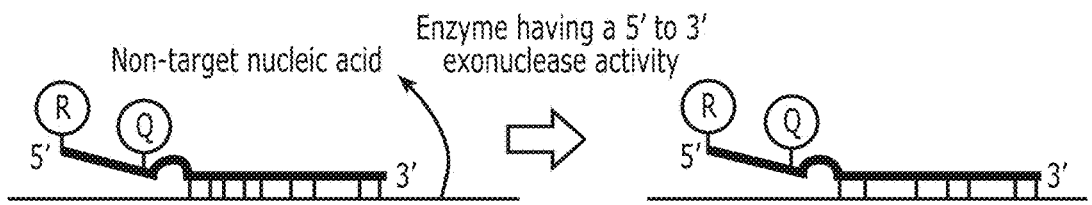

When a dual-labeled target discriminative (TD) probe is hybridized with a non-target nucleic acid sequence, the 5'-second hybridization portion of the TD probe forms a single strand such that the 5'-second hybridization portion is not digested by an enzyme having a 5' to 3' exonuclease activity.

FIG. 2B

No signal on non-target hybridization

- (R) : Reporter molecule
- (Q) : Quencher molecule

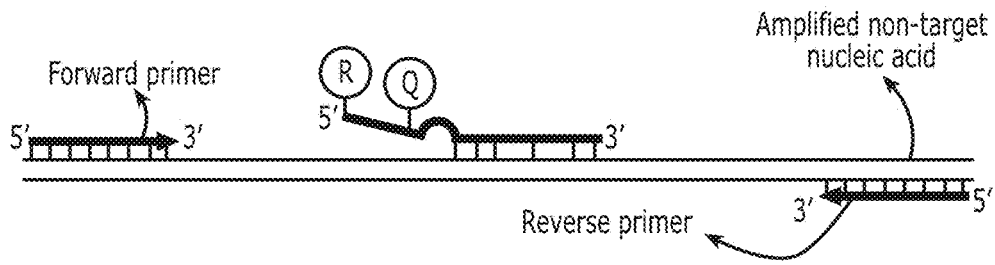
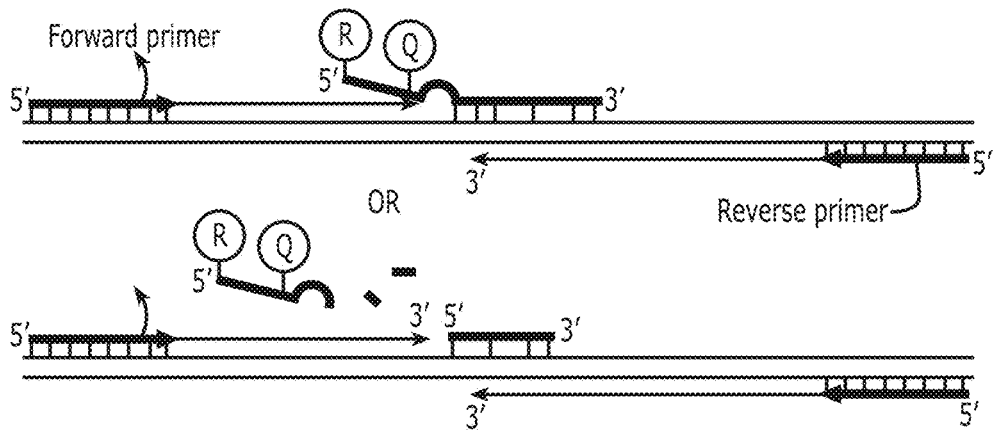
FIG. 3
Non-target hybridization in Real-time PCR

Target-specific hybridization

Non-target hybridization

Signal generation on target-specific hybridization

No signal on non-target hybridization

Target-specific hybridization

Non-target hybridization

Target-specific hybridization

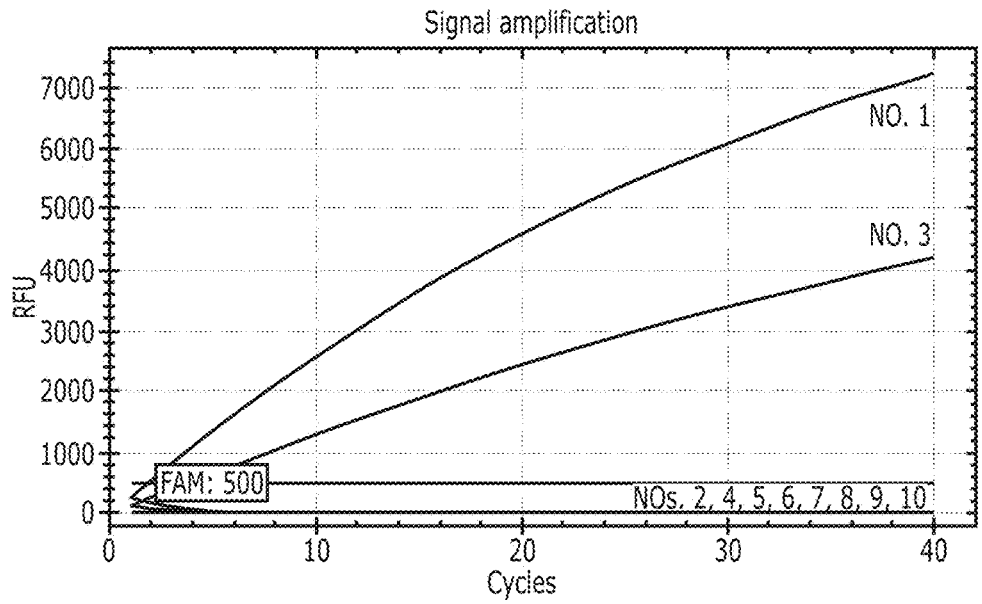

| No. | Template [1] | Probe [2] | Ct value |
|---|---|---|---|
| 1 | + | SA_P0 [3] | 1.93 |
| 2 | - | SA_P0 | - |
| 3 | + | SA_P1 [4] | 3.81 |
| 4 | - | SA_P1 | - |
| 5 | + | SA_P3 [5] | - |
| 6 | - | SA_P3 | - |
| 7 | + | SA_P6 [6] | - |
| 8 | - | SA_P6 | - |
| 9 | + | SA_P9 [7] | - |
| 10 | - | SA_P9 | - |

1) Template is a synthetic oligonucleotide for *Staphylococcus aureus* gene.
2) Probe has a reporter molecule at its 5'-end and a quencher molecule at its 3'-end portion.
3) SA_P0 has a matched sequence at its 5'-end portion.
4) SA_P1 has a single mismatched nucleotide at its 5'-end.
5) SA_P3 has three mismatched nucleotides at its 5'-end portion.
6) SA_P3 has six mismatched nucleotides at its 5'-end portion.
7) SA_P9 has nine mismatched nucleotides at its 5'-end portion.

FIG. 8

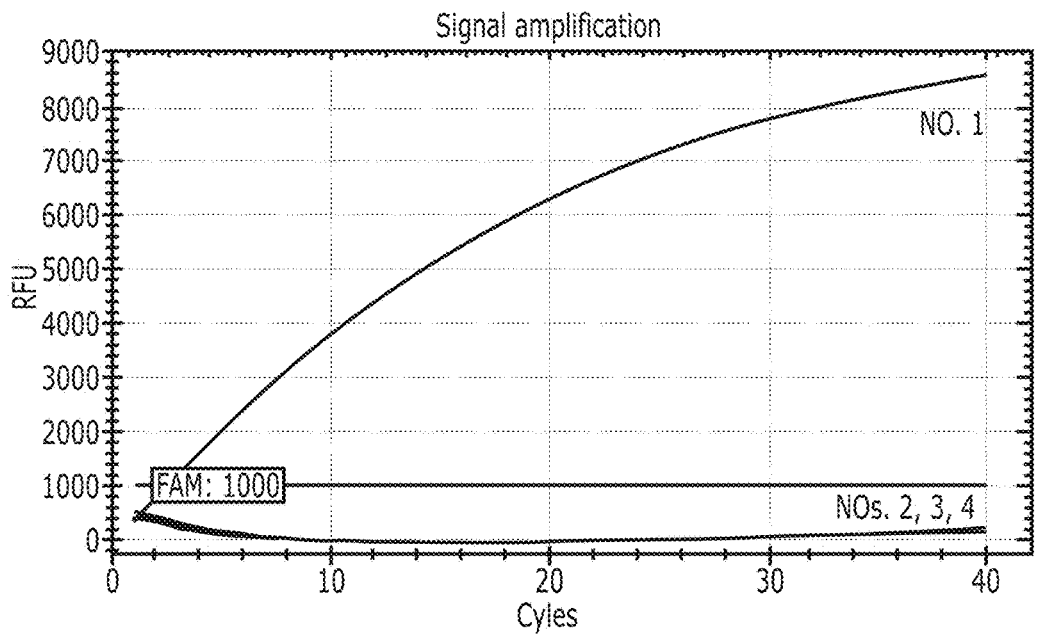

| No. | Template [1] | Probe [2] | Ct value |
|---|---|---|---|
| 1 | + | SA_TD_M [3] | 2.53 |
| 2 | - | SA_TD_M | - |
| 3 | + | SA_TD_m [4] | - |
| 4 | - | SA_TD_m | - |

1) Template is a synthetic oligonucleotide for *Staphylococcus aureus* gene.
2) TD probe has a reporter molecule at its 5'-end and a quencher molecule at its 3'-first hybridization portion.
3) SA_TD_M has a matched sequence at its 5'-second hybridization portion.
4) SA_TD_m has a mismatched sequence at its 5'-second hybridization portion.

FIG. 9A

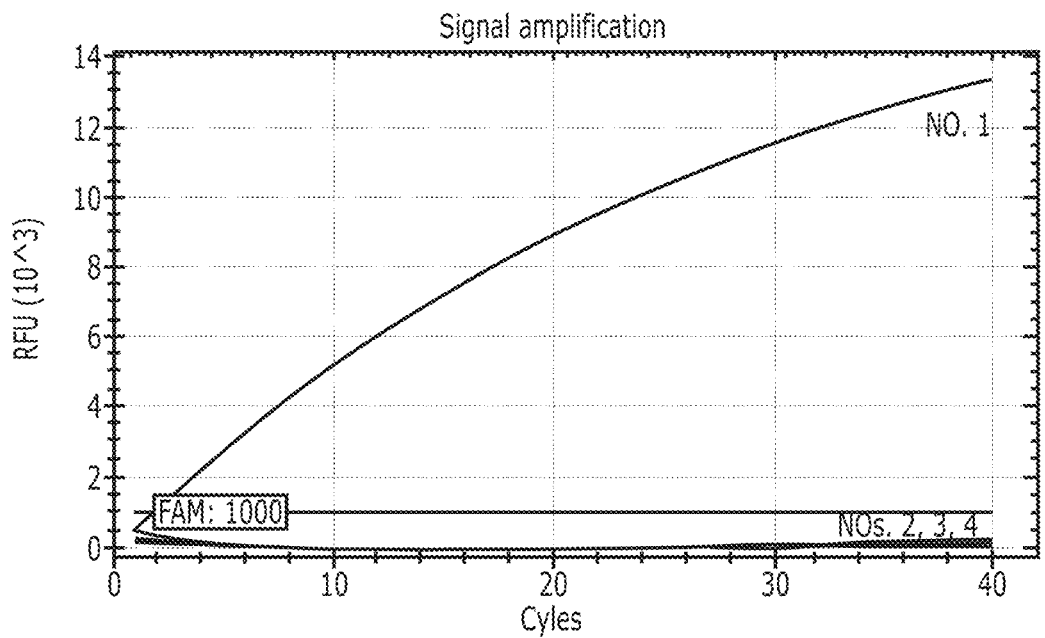

| No. | Template[1] | Probe[2] | Ct value |
|---|---|---|---|
| 1 | + | NG_TD_M[3] | 1.88 |
| 2 | - | NG_TD_M | - |
| 3 | + | NG_TD_m[4] | - |
| 4 | - | NG_TD_m | - |

1) Template is a synthetic oligonucleotide for *Neisseria gonorrhoeae* gene.
2) TD probe has a reporter molecule at its 5'-end and a quencher molecule at its 3'-first hybridization portion.
3) NG_TD_M has a matched sequence at its 5'-second hybridization portion.
4) NG_TD_m has a mismatched sequence at its 5'-second hybridization portion.

FIG. 9B

| No. | Template [1] | Probe [2] | Ct value |
|---|---|---|---|
| 1 | + | NG_TD2_M [3] | 26.31 |
| 2 | - | NG_TD2_M | - |
| 3 | + | NG_TD2_m [4] | - |
| 4 | - | NG_TD2_m | - |

1) Template is a genomic DNA of *Neisseria gonorrhoeae*.
2) TD probe has both a reporter molecule and a quencher molecule at its 5'-second hybridization portion.
3) NG_TD2_M has a matched sequence at its 5'-second hybridization portion.
4) NG_TD2_m has a mismatched sequence at its 5'-second hybridization portion.

| No. | Template[1] | Probe[2] | Ct value |
|---|---|---|---|
| 1 | + | SA_TD_S_M[3] | 22.95 |
| 2 | - | SA_TD_S_M | - |
| 3 | + | SA_TD_S_m[4] | - |
| 4 | - | SA_TD_2_m | - |

1) Template is a genomic DNA of *Staphylococcus aureus*.
2) TD probe has both a reporter molecule and a quencher molecule at its 5'-second hybridization portion.
3) SA_TD_S_M has a matched sequence at its 5'-second hybridization portion.
4) SA_TD_S_m has a mismatched nucleotide at its 5'-second hybridization portion.

- SA_TD1_Chip_M is a TD probe having a matched sequence at its 5'-second hybridization portion.
- SA_TD1_Chip_m is a TD probe having a mismatched sequence at its 5'-second hybridization portion.
- Each spot was duplicated for the test of reproducibility.
- The fluorescence intensity indicates the average value of the duplicated spots.

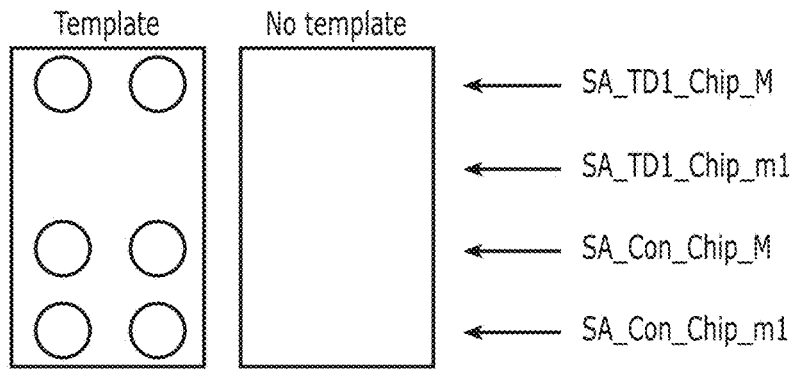

FIG. 14A

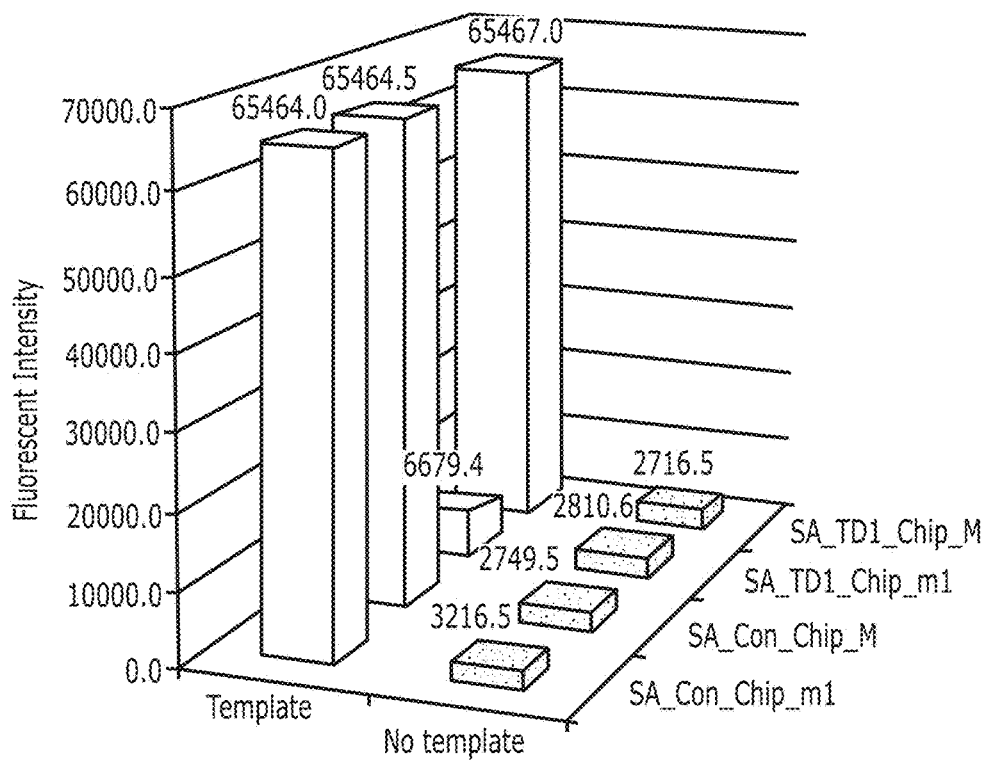

- SA_TD1_Chip_M is a TD probe having a matched sequence at its 5'-second hybridization portion.
- SA_TD1_Chip_m1 is a TD probe having three mismatched nucleotides at its 5'-second hybridization portion.
- SA_Con_Chip_M is a conventional probe having a matched sequence at its 5'-end portion.
- SA_Con_Chip_m1 is a conventional probe having three mismatched nucleotides at its 5'-end portion.

FIG. 14B

TD PROBE AND ITS USES

CROSS REFERENCE TO RELATED APPLICATIONS

This application claims the priority of Ser. No. 13/392,400 filed Feb. 24, 2012, which claims the priority of PCT/KR2010/005971, filed on Sep. 2, 2010, which claims the benefit of priority to PCT/KR2010/004119, filed on Jun. 24, 2010, and Korea Application No. 10-2009-0083196, filed on Sep. 3, 2009, the entire contents of which are hereby incorporated in total by reference.

BACKGROUND OF THE INVENTION

Field of the Invention

The present invention relates to a target discriminative probe (TD probe) and its uses or applications.

SEQUENCE LISTING

This application incorporates by reference the Sequence Listing contained in an ASCII text file named "361406_00009_ST25.txt" submitted via EFS-Web. The text file was created on May 19, 2017, and is 10 kb in size.

DESCRIPTION OF THE RELATED ART

DNA hybridization is a fundamental process in molecular biology. Many technologies using DNA hybridization will surely be very useful tools in specific target sequence detection and clearly be valuable in clinical diagnosis, genetic research, and forensic laboratory analysis.

Recently, there have been many efforts to improve the specificity of oligonucleotide hybridization because DNA hybridization is affected by many conditions like salt concentration, temperature, organic solvents, base composition, length of the complementary strands, and the number of nucleotide base mismatches between the hybridizing nucleic acids (Maniatis et al., Molecular Cloning, A Laboratory Manual, Cold Springs Harbor Laboratory, 1982 and Sambrook et al., 1989). Over the past decade a lot of methods have been proposed; a method for chemically modifying bases of DNA for high-sensitivity hybridization (Azhikina et al., (1993) Proc. Natl. Acad. Sci., USA, 90:11460-11462) and a method in which the washing after the hybridization is conducted at low temperatures for a long period to enhance the ability of discriminating the mismatch (Drmanac et al., (1990) DNA and Cell Biology, 9:527-534). Recently, another method has been introduced for increasing the resolution power of single nucleotide polymorphisms (SNPs) in DNA hybridization by means of artificial mismatches (Guo et al., (1997) Nature Biotechnology, 15:331-5). In addition, many U.S. patents including U.S. Pat. Nos. 6,077,668, 6,329,144, 6,140,054, 6,350,580, 6,309,824, 6,342,355 and 6,268,128 disclose the probe for hybridization and its applications.

Many methods have been proposed for the detection of target sequences using probes. Among these types of methods, there are a number of proposed methods using hybridization probes and nucleolytic enzymes. The TaqMan™ probe method is one of the typical examples of using these principles. The TaqMan™ probes are oligonucleotides that contain a fluorescent dye, typically on the 5'-end, and a quenching dye, typically located on the 3'-end. When irradiated, the excited fluorescent dye transfers energy to the nearby quenching dye molecule rather than fluorescing, resulting in a non-fluorescent substrate. The TaqMan™ probes are designed to hybridize to an internal region of a PCR product. During PCR, when the polymerase replicates a template on which the TaqMan™ probes are bound, the 5' to 3' exonuclease activity of the polymerase cleaves the probes. This separates the fluorescent and quenching dyes and the fluorescence resonance energy transfer (FRET) no longer occurs. Fluorescence increases in each cycle, proportional to the rate of probe cleavage. (Parashar et al, Indian J Med Res 124: 385-398(2006)). Namely, it is the feature of the TaqMan™ probe method to utilize the hybridization and cleavage reactions by the 5' to 3' nuclease activity of the polymerase. However, this technology carries an inherent limitation by itself. The most critical problem associated with the TaqMan™ probe method is the non-specific hybridization of probes because it is necessarily accompanied with the hybridization between the probes and the target sequences. In addition, this method is very likely to produce false positive signals (results), especially in multiplex detection of a plurality of target sequences.

Another approach for the detection of target sequences is to use probe ligation methods (D. Y. Wu, et al., Genomics 4:560 (1989), U. Landegren, et al., Science 241:1077 (1988), and E. Winn-Deen, et al., Clin. Chem. 37:1522 (1991)). Ligation reaction is considered as a promising tool for the detection of point mutations. In oligonucleotide ligation assay (OLA), two probes spanning a target region of interest are hybridized to the target region. Where the probes are hybridized with adjacent target bases, the confronting ends of the probe elements can be joined by ligation, e.g., by treatment with ligase. The ligated probe is indicative of the presence of the target sequence. It is reported that DNA ligases catalyze to link DNA substrates with mismatched nucleotides at the ligation site (Luo J, et al., Nucleic acid res 24:3071 (1996)). Even in the ligation-based target detection approaches, there also remains need to prevent non-specific binding of probes to target sequences. Also, it is required that the ligation reaction occurs with much higher specificity, e.g., with discriminating a single mismatch nucleotide present at a ligation site.

There are growing needs for a useful method to detect the presence, level or expression patterns of each of a large number of a gene or a gene population simultaneously. One of the most promising methods for these purposes is microarray-based technologies (Schena et al., 1995. Quantitative Monitoring of Gene Expression Patterns with a Complementary DNA Microarray, Science, 270:467-470; DeRisi et al., 1996, Use of a cDNA Microarray to Analyse Gene Expression Patterns in Human Cancer, Nature Genetics 14:457-460). Microarray-based technologies suggested so far relate to detection of genes or nucleotide variations and analysis of their expression patterns.

Microarray-based technologies generally use single-stranded oligonucleotides (nucleic acid probes) which is complementary to a specific nucleic acid sequence in the target nucleic acid. However, since the conventional DNA microarrays depend mostly on hybridization to detect target nucleotide sequences, they have serious shortcomings of a high rate of false positives. Especially, when a large number of probes are used, the occurrence of cross hybridization events cannot be excluded. This cross-hybridization can dramatically affect the data quality and cause false positive/false negative results. Furthermore, Microarray needs numerous liquid handling steps, and the temperatures for incubation and washing should be cautiously controlled for the discrimination of single nucleotide mismatch. It has been proven that the multiplexing of this approach is very difficult because of the different optimal hybridization conditions among many probe sequences. (William E. Bunney, et al. 2003. Microarray Technology: A Review of New Strategies to Discover Candidate Vulnerability Genes in Psychiatric Disorders, Am. J. Psychiatry 160:4, 657-666).

Although the improved approaches to each method have been continuously introduced, all these methods and techniques involving oligonucleotide hybridization could not be completely free from the limitations and problems arising from non-specificity of oligonucleotide hybridization.

Throughout this application, various patents and publications are referenced and citations are provided in parentheses. The disclosure of these patents and publications in their entities are hereby incorporated by references into this application in order to more fully describe this invention and the state of the art to which this invention pertains.

SUMMARY OF THE INVENTION

Under such circumstances, we have understood that novel probes capable of specifically hybridizing with target sequences in a different hybridization manner from conventional probes should be provided to overcome drawbacks of conventional technologies. In particular, we appreciated that the novel probes should have peculiar target-discrimination performance in nucleolytic reactions by nuclease as well as ligations.

The present inventors have made intensive studies to develop novel target detection technologies for detection or identification of target nucleic acid sequences with no false positive and negative results in more convenient manner. As a result, the present inventors have designed a novel target discriminative probe that has different hybridization patterns for target and non-target nucleic acid sequences and therefore inherently capability of discriminating target nucleic acid sequences from non-target nucleic acid sequences. In addition, with help of the novel target discriminative probes, the present inventors have proposed novel detection protocols for target nucleic acid sequences plausibly applicable to both liquid phase and solid phase reactions.

Accordingly, it is an object of this invention to provide a target discriminative probe (TD probe) to allow for discrimination of a target nucleic acid sequence from a non-target nucleic acid sequence.

It is another object of this invention to provide a method for detecting a target nucleic acid sequence from a DNA or a mixture of nucleic acids using a target discriminative probe (TD probe) by a 5' to 3' exonucleolytic reaction in a liquid phase or a solid phase.

It is still another object of this invention to provide a method for detecting a target nucleic acid sequence from a DNA or a mixture of nucleic acids using a target discriminative probe (TD probe) and a polymerase chain reaction (PCR).

It is further object of this invention to provide a method for detecting a target nucleic acid sequence from a DNA or a mixture of nucleic acids using a target discriminative probe (TD probe) by a ligation reaction.

It is still further object of this invention to provide kits for detecting a target nucleic acid sequence from a DNA or a mixture of nucleic acids.

Other objects and advantages of the present invention will become apparent from the detailed description to follow taken in conjugation with the appended claims and drawings.

BRIEF DESCRIPTION OF THE DRAWINGS

FIG. 1A illustrates signal generation on target-specific hybridization. FIG. 1B illustrates no signal on non-target hybridization.

FIGS. 2A and 2B schematically represent the discrimination of a target nucleic acid from a non-target nucleic acid sequence using a dual-labeled TD probe and an enzyme having a 5' to 3' exonuclease activity. The TD probe has both a reporter molecule and a quencher molecule at its 5'-second hybridization portion. FIG. 2A illustrates signal generation on target-specific hybridization. FIG. 2B illustrates no signal on non-target hybridization.

FIG. 3 schematically represents no signal generation in a real-time PCR reaction using a template-dependent DNA polymerase having a 5' to 3' exonuclease activity when a dual-labeled TD probe having both a reporter molecule and a quencher molecule at its 5'-second hybridization portion is hybridized on a non-target nucleic acid sequence.

FIG. 4A represents a change of fluorescent signal intensity on target-specific hybridization of the immobilized TD probe. FIG. 4B represents no change of fluorescent signal intensity on non-target hybridization of the immobilized TD probe.

FIG. 5A represents signal generation on target-specific hybridization of the immobilized TD probe. FIG. 5B represents no signal on non-target hybridization of the immobilized TD probe.

FIG. 6A represents the ligation between the first probe and the second probe on target-specific hybridization. FIG. 6B represents no ligation of the probes on non-target hybridization.

FIG. 8 shows the results of the cleavage activity of an enzyme having a 5' to 3' exonuclease activity on 5'-end mismatched probes. Symbols, [1]Template is a synthetic oligonucleotide for Staphylococcus aureus gene; [2]Probe has a reporter molecule at its 5'-end and a quencher molecule at its 3'-end portion; [3]SA_P0 has a matched sequence at its 5'-end portion; [4]SA_P1 has a single mismatched nucleotide at its 5'-end; [5]SA_P3 has three mismatched nucleotides at its 5'-end portion; [6]SA_P6 has six mismatched nucleotides at its 5'-end portion; [7]SA_P9 has nine mismatched nucleotides at its 5'-end portion.

FIGS. 9A and 9B show the results of the discrimination of a target nucleic acid sequence from a non-target nucleic acid sequence depending on the hybridization of the 5'-second hybridization portion of a dual-labeled TD probe. FIGS. 9A and 9B show the detection of *Staphylococcus aureus* gene and *Neisseria gonorrhoeae* gene, respectively. In FIG. 9A, Symbols: [1]Template is a synthetic oligonucleotide for *Staphylococcus aureus* gene; [2]TD probe has a reporter molecule at its 5'-end and a quencher molecule at its 3'-first hybridization portion; [3]SA_TD_M has a matched sequence at its 5'-second hybridization portion; [4]SA_TD_m has a mismatched sequence at its 5'-second hybridization portion. In FIG. 9B, Symbols: [1]Template is a synthetic oligonucleotide for *Neisseria gonorrhoeae* gene; [2]TD probe has a reporter molecule at its 5'-end and a quencher molecule at its 3'-first hybridization portion; [3]NG_TD_M has a matched sequence at its 5'-second hybridization portion; [4]NG_TD_m has a mismatched sequence at its 5'-second hybridization portion.

FIGS. 11A and 11B show the detection of *Staphylococcus aureus* gene and *Neisseria gonorrhoeae* gene, respectively. In FIG. 11A, Symbols: [1]Template is a genomic DNA of *Staphylococcus aureus*, [2]TD probe has both a reporter molecule and a quencher molecule at its 5'-second hybridization portion; [3]SA_TD2_M has a matched sequence at its 5'-second hybridization portion; [4]SA_TD2_m has a mismatched sequence at its 5'-second hybridization portion. In FIG. 11B, Symbols: [1]Template is a genomic DNA of *Neisseria gonorrhoeae*; [2]TD probe has both a reporter molecule and a quencher molecule at its 5'-second hybridization portion; [3]NG_TD2_M has a matched sequence at its 5'-second hybridization portion; [4]NG_TD2_m has a mismatched sequence at its 5'-second hybridization portion.

FIGS. 14A and 14B show the results of comparison between a TD probe and a conventional probe for the detection of *Staphylococcus aureus* gene in solid phase. Symbols: SA_TD1_Chip_M is a TD probe having a matched sequence at its 5'-second hybridization portion; SA_TD1_Chip_m1 is a TD probe having three mismatched nucleotides at its 5'-second hybridization portion; SA_Con_Chip_M is a conventional probe having a matched sequence at its 5'-end portion; SA_Con_Chip_m1 is a conventional probe having three mismatched nucleotides at its 5'-end portion.

DETAILED DESCRIPTION OF THIS INVENTION

Figure 1A:
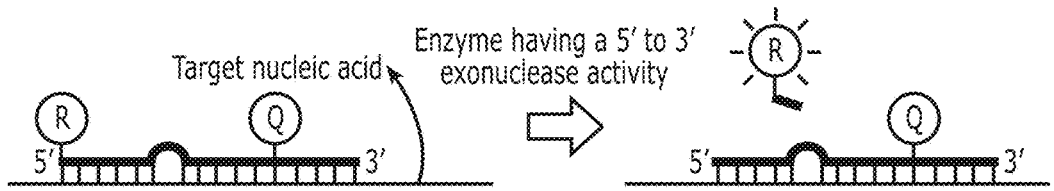
FIGS. 1A and 1B schematically represent the discrimination of a target nucleic acid sequence from a non-target nucleic acid sequence using a dual-labeled TD probe and an enzyme having a 5' to 3' exonuclease activity. The TD probe has a reporter molecule at its 5'-second hybridization portion and a quencher molecule at its 3'-first hybridization portion.

The present invention is drawn to a target discriminative probe (TD probe) and its uses or applications.

As used herein "Known Nucleic Acid Sequence(s)" shall mean nucleic acid sequence(s) having a sequence that is publicly available as of the filing date of the present application.

As used herein "Previously Known Nucleic Acid Sequence(s)" shall mean nucleic acid sequence(s) having a sequence that is publicly available as of the priority date of the present application.

As used herein "Nucleic Acid Sequence Known To The User" shall mean a nucleic acid sequence that is publicly available at the time of use of the method of the present invention.

TD Probes

In one aspect of the present invention, there is provided a target discriminative probe (TD probe) having a modified dual specificity oligonucleotide (mDSO) structure represented by the following general formula I to allow for discrimination of a target nucleic acid sequence from a non-target nucleic acid sequence:

$$5'\text{-}X'_p\text{—}Y'_q\text{—}Z'_r\text{-}3' \quad (I)$$

wherein, $X'_p$ represents a 5'-second hybridization portion having a hybridizing nucleotide sequence complementary to the target nucleic acid sequence; $Y'_q$ represents a separation portion comprising at least three universal bases, $Z'_r$ represents a 3'-first hybridization portion having a hybridizing nucleotide sequence complementary to the target nucleic acid sequence; p, q and r represent the number of nucleotides; and X, Y' and Z' are deoxyribonucleotides or ribonucleotides; the $T_m$ of the 5'-second hybridization portion is lower than that of the 3'-first hybridization portion and the separation portion has the lowest $T_m$ in the three portions of $X'_p$, $Y'_q$ and $Z'_r$; the separation portion separates the 5'-second hybridization portion from the 3'-first hybridization portion in terms of hybridization events to the target nucleic acid sequence, whereby the hybridization specificity of the TD probe are determined dually by the 5'-second hybridization portion and the 3'-first hybridization portion such that the overall hybridization specificity of the TD probe is enhanced; wherein when the TD probe is hybridized with the target nucleic acid sequence, both of the 5'-second hybridization portion and the 3'-first hybridization portion are hybridized with the target nucleic acid sequence; wherein when the TD probe is hybridized with the non-target nucleic acid sequence, both of the 5'-second hybridization portion and the separation portion form a single strand, whereby the TD probe allows discriminating the target nucleic acid sequence from the non-target nucleic acid sequence.

The present inventors have made intensive studies to develop novel target detection technologies for detection or identification of target nucleic acid sequences with no false positive and negative results in more convenient manner. As a result, the present inventors have designed a novel target discriminative probe that has different hybridization patterns for target and non-target nucleic acid sequences and therefore inherently capability of discriminating target nucleic acid sequences from non-target nucleic acid sequences. In addition, with help of the novel target discriminative probes, the present inventors have proposed novel detection protocols for target nucleic acid sequences plausibly applicable to both liquid phase and solid phase reactions.

Therefore, the probe used in the present invention is called a "Target Discriminative Probe" (TD probe) and the present technologies using the TD probe called "TD probe Target Detection Assay".

The TD probe of the present invention has the modified dual specificity oligonucleotide (mDSO) structure comprising three different portions with distinct properties within one oligonucleotide molecule: 5'-second hybridization portion, 3'-first hybridization portion and separation portion. Such a structure permits TD probe to serve as a probe exhibiting much higher specificity, rendering the present invention to be novel and unobvious over prior art.

The mDSO structure is a newly modified version of a DSO (dual specificity oligonucleotide) structure that was first proposed by the present inventor (see WO 2006/095981). The DSO structure is also called DPO (dual priming oligonucleotide) as it serves as primers (Chun et al., Dual priming oligonucleotide system for the multiplex detection of respiratory viruses and SNP genotyping of CYP2C19 gene, *Nucleic Acid Research*, 35:6e40(2007)).

The DSO embodies a novel concept in which its hybridization or annealing is dually determined by the 5'-high $T_m$ specificity portion (or the 5'-first hybridization portion, the 5'-first priming portion) and the 3'-low $T_m$ specificity portion (or the 3'-second hybridization portion, the 3'-second priming portion) separated by the separation portion, exhibiting dramatically enhanced hybridization specificity (see WO 2006/095981; Kim et al, Direct detection of lamivudine-resistant hepatitis B virus mutants by multiplex PCR using dual-priming oligonucleotide primers, *Journal of Virological Methods*, 149:76-84(2008); Kim, et. al, Rapid detection and identification of 12 respiratory viruses using a dual priming oligonucleotide system-based multiplex PCR assay, Journal of Virological Methods, doi:10.1016/j.jviromet.2008.11.007(2008); Horii et. al, Use of dual priming oligonucleotide system to detect multiplex sexually transmitted pathogens in clinical specimens, Letters in Applied Microbiology, doi:10.111/j.1472-765X2009.02618x (2009)). As such, the DSO has eventually two segments with distinct hybridization properties: the 5'-first hybridization portion that initiates stable hybridization, and the 3'-second hybridization portion that mainly determines target specificity.

The mDSO structure is a reversal of the DSO structure: the 5'-second hybridization portion that mainly determines target specificity, and the 3'-first hybridization portion that initiates stable hybridization.

Where the TD probe having the mDSO structure is hybridized with non-target sequences, its 5'-end portion rather than the 3'-end portion is not involved in the hybridization, which is distinctly different from the DSO structure previously suggested by the present inventor.

To completely overcome problems associated with false positive signals particularly associated with probes, the present inventors have made intensive efforts to propose more reliable and accurate approaches in which the signal generation indicative of target sequences is accomplished by not only probe hybridization but also additional enzymatic reactions such as 5' to 3' exonuclease reaction and ligation of two probes. Given that the novel approaches are dependent heavily on hybridization of the 5'-end portion of probes, the present inventors have designed probes being able to exhibit maximized 5'-end specificity performance and have modified the known DSO to propose the TD probe.

The TD probe with peculiar 5'-end hybridization patterns allows for detection of target sequences with no false positive signals, which has not been accomplished by conventional probes and DSO probes.

The hybridization specificity (or target specificity) of the TD probe owing to the mDSO structure contributes to false-free target detection in the present invention.

Figure 1B:
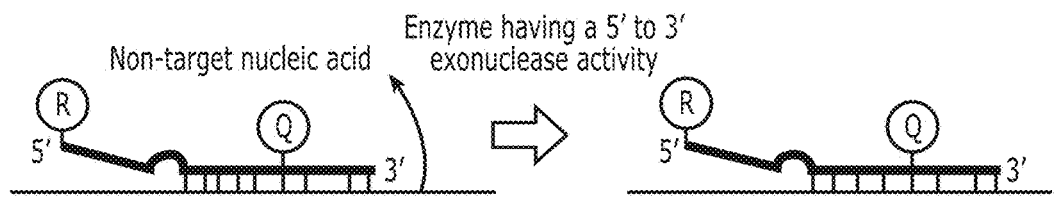

Interestingly, the TD probe having the mDSO structure exhibits distinctly different hybridization behaviors for each of target and non-target nucleic acid sequences. As schematically represented in FIGS. 1-3, when the TD probe is hybridized with a target nucleic acid sequence, both the 5'-second hybridization portion and the 3'-first hybridization portion of the TD probe form a double strand with the target nucleic acid sequence. Where the TD probe is hybridized with a non-target nucleic acid sequence (i.e., non-target hybridization or binding), its 3'-first hybridization portion prevailingly binds to the non-target nucleic acid sequence but both of the 5'-second hybridization portion and the separation portion are not hybridized with the non-target nucleic acid sequence such that both portions form a single strand.

While the 3'-first hybridization portion is annealed to a non-target sequence, the 5'-second hybridization portion having a shorter sequence (lower $T_m$ value) is unlikely to hybridize to the non-target sequence under the target-specific hybridization condition of TD probe. The reasons are that the 3'-first hybridization portion and the 5'-second hybridization portion are separated by the separation portion in terms of hybridization events. In other words, the 5'-second hybridization portion is involved in hybridization events in a relatively independent manner from the 3'-first hybridization portion and the hybridization of the 5'-second hybridization portion is less affected by the hybridization of the 3'-first hybridization portion. In this connection, the likelihood of hybridization of the 5'-second hybridization portion to a non-target sequence becomes much lower.

Where both 3'-first hybridization portion and 5'-second hybridization portion of the TD probe have a sequence complementary to a template, the TD probe can be specifically hybridized to the target nucleic acid sequence of the template under the target-specific hybridization condition. However, where only the 5'-second hybridization portion of TD probe has a sequence complementary to a template, the TD probe can not be hybridized to the template under the target-specific hybridization condition.

The characteristics of the TD probe described above permit to detect target sequences with dramatically enhanced target-specificity through the following two target-surveillance events. First, the TD probe having different hybridization patterns for each of target and non-target nucleic acid sequences as described above is capable of discriminating target nucleic acid sequences from non-target nucleic acid sequences with much higher specificity. Second, the occurrence of successive enzymatic reactions (5' to 3' exonucleolytic reaction or ligation) is determined depending on the hybridization patterns of the TD probe, elevating target-specificity in the target detection procedures.

TD probe is hybridized with a target nucleic acid sequence and it forms a double strand. As discussed hereinabove, the TD probe having the mDSO structure with such intriguing design allows to perfectly discriminate target nucleic acid sequences from non-target nucleic acid sequences.

According to a preferred embodiment, the universal base in the separation portion is selected from the group consisting of deoxyinosine, inosine, 7-deaza-2'-deoxyinosine, 2-aza-2'-deoxyinosine, 2'-OMe inosine, 2'-F inosine, deoxy 3-nitropyrrole, 3-nitropyrrole, 2'-OMe 3-nitropyrrole, 2'-F 3-nitropyrrole, 1-(2'-deoxy-beta-D-ribofuranosyl)-3-nitropyrrole, deoxy 5-nitroindole, 5-nitroindole, 2'-OMe 5-nitroindole, 2'-F 5-nitroindole, deoxy 4-nitrobenzimidazole, 4-nitrobenzimidazole, deoxy 4-aminobenzimidazole, 4-aminobenzimidazole, deoxy nebularine, 2'-F nebularine, 2'-F 4-nitrobenzimidazole, PNA-5-introindole, PNA-nebularine, PNA-inosine, PNA-4-nitrobenzimidazole, PNA-3-nitropyrrole, morpholino-5-nitroindole, morpholino-nebularine, morpholino-inosine, morpholino-4-nitrobenzimidazole, morpholino-3-nitropyrrole, phosphoramidate-5-nitroindole, phosphoramidate-nebularine, phosphoramidate-inosine, phosphoramidate-4-nitrobenzimidazole, phosphoramidate-3-nitropyrrole, 2'-0-methoxyethyl inosine, 2'0-methoxyethyl nebularine, 2'-0-methoxyethyl 5-nitroindole, 2'-0-methoxyethyl 4-nitro-benzimidazole, 2'-0-methoxyethyl 3-nitropyrrole, and combinations thereof. More preferably, the universal base is deoxyinosine, 1-(2'-deoxy-beta-D-ribofuranosyl)-3-nitropyrrole or 5-nitroindole, most preferably, deoxyinosine.

Preferably, the separation portion comprises nucleotides having at least three, more preferably at least four most preferably at least five universal bases. More preferably, the separation portion comprises contiguous nucleotides having at least three, more preferably at least four most preferably at least five universal bases. Alternatively, the separation portion comprises 3-10, 3-8, 4-7 or 4-5 contiguous universal bases.

Preferably, the 3'-first hybridization portion is longer than the 5'-second hybridization portion. The 3'-first hybridization portion is preferably 15-60 nucleotides, more preferably 15-40 nucleotides, still more preferably 15-30 nucleotides in length.

Preferably, the 5'-second hybridization portion is at least 3, more preferably 5 and still more preferably 6 nucleotides in length. Preferably, the 5'-second hybridization portion is no more than 15, more preferably no more than 13 and still more preferably no more than 12 nucleotides in length.

It is preferable that the 5'-second hybridization portion is 3-15 nucleotides, more preferably 3-13 nucleotides, still more preferably 4-12 nucleotides and most preferably 5-11 nucleotides in length. The separation portion is preferably 3-10 nucleotides, more preferably 3-8 nucleotides, still more preferably 4-7 nucleotides, most preferably 4-5 nucleotides in length. The length of both 5'-second hybridization portion and separation portion is preferably at least six, more preferably at least nine, still more preferably at least twelve and most preferably at least fifteen nucleotides.

According to a preferred embodiment, the $T_m$ of the 3'-first hybridization portion ranges from 40° C. to 80° C., more preferably 45° C. to 70° C. The $T_m$ of the 5'-second hybridization portion ranges preferably from 6° C. to 40° C. and more preferably from 10° C. to 40° C. The $T_m$ of the separation portion ranges preferably from 2° C. to 15° C. and more preferably 3° C. to 15° C.

According to a preferred embodiment, the TD probe has a label or an interactive label system containing a plurality of labels to generate a detectable signal indicative of target nucleic acid sequences.

The label generating a detectable signal useful in the present invention includes any label known to one of skill in the art. Some of labels are composed of a single molecule or a single atom label; however most of labels (e.g., interactive label system) composed of at least two or more label molecules or atoms.

According to a preferred embodiment, the label on the TD probe is a chemical label, an enzymatic label, a radioactive label, a fluorescent label, a luminescent label, a chemiluminescent label or a metal label (e.g., gold).

The chemical label includes biotin. The binding specificity of biotin to streptavidin (or avidin) allows for an indirect signal generation indicative of target nucleic acid sequences.

The enzymatic label includes alkaline phosphatase, β-galactosidase, β-glucosidase, luciferase, cytochrome $P_{450}$ and horseradish peroxidase. Using substrates for the enzymatic labels, the signal indicative of target nucleic acid sequences may be obtained. Where using alkaline phosphatase, bromochloroindolylphosphate (BCIP), nitro blue tetrazolium (NBT) or ECF may be used as a substrate for color-developing reactions in the case of using horseradish peroxidase, chloronaphtol, aminoethylcarbazol, diaminobenzidine, D-luciferin, lucigenin (bis-N-methylacridinium nitrate), resorufin benzyl ether, luminol, Amplex Red reagent (10-acetyl-3,7-dihydroxyphenoxazine), HYR (p-phenylenediamine-HCl and pyrocatechol), TMB (3,3,5, 5-tetramethylbenzidine), ABTS (2,2-Azine-di[3-ethylbenzthiazoline sulfonate]), o-phenylenediamine (OPD) or naphtol/pyronine may be used as a substrate; and in the case of using glucose oxidase, t-NBT (nitroblue tetrazolium) or m-PMS (phenzaine methosulfate) may be used as a substrate.

The radioactive label includes $C^{14}$, $I^{125}$, $P^{32}$ and $S^{35}$.

According to a preferred embodiment of the present invention, the label linked to TD probe is a single label capable of providing real-time signal. For example, the single label is fluorescent terbium chelat (Nurmi et al, *Nucleic Acids Research,* 2000, Vol. 28 No. 8). Nurmi et al disclosed that the label emits low level of fluorescence in a probe-linked form, but when the label is released from the probe-template duplex by 5' to 3' nucleolytic activity, the fluorescence signal is enhanced. Therefore, the fluorescent terbium chelate allows real-time target detection even though a single label is linked to the TD probe for the prevent invention.

The interactive label system is a signal generating system in which energy is passed non-radioactively between a donor molecule and an acceptor molecule.

As a representative of the interactive label system, the FRET (fluorescence resonance energy transfer) label system includes a fluorescent reporter molecule (donor molecule) and a quencher molecule (acceptor molecule). In FRET, the energy donor is fluorescent, but the energy acceptor may be fluorescent or non-fluorescent.

In another form of interactive label systems, the energy donor is non-fluorescent, e.g., a chromophore, and the energy acceptor is fluorescent. In yet another form of interactive label systems, the energy donor is luminescent, e.g. bioluminescent, chemiluminescent, electrochemiluminescent, and the acceptor is fluorescent.

More preferably, the label on the TD probe is the interactive label systems, still more preferably the FRET label system, most preferably a pair of a reporter molecule and a quencher molecule.

Preferably, where the FRET label is used, two labels (a reporter molecule and a quencher molecule positioned on the TD probe) are separated by a site within the TD probe susceptible to nuclease cleavage, whereby allowing the 5' to 3' exonuclease activity to separate the reporter molecule from the quencher molecule by cleaving at the susceptible site thereby obtaining the signal indicative of the presence of the target nucleic acid sequence.

The label may be linked to the TD probe in accordance with conventional methods. For example, the label may be linked to the TD probe via a spacer containing at least three carbon atoms (e.g., 3-carbon spacer, 6-carbon spacer or 12-carbon spacer).

According to a preferred embodiment, the reporter molecule and the quencher molecule all are positioned on the 5'-second hybridization portion or the reporter molecule and the quencher molecule each is positioned on each different portion of the 5'-second hybridization portion and the separation portion. For example, the reporter molecule is positioned on the 5'-second hybridization portion and the quencher molecule on the separation portion. Alternatively, the quencher molecule is positioned on the 5'-second hybridization portion and the reporter molecule on the separation portion.

More preferably, one of the reporter molecule and the quencher molecule is located at the 5'-end of the TD probe and the other located at a site of the 5'-second hybridization portion.

According to a preferred embodiment, the TD probe has one of the reporter molecule and the quencher molecule on its 5'-second hybridization portion and the other on its 3'-first hybridization portion.

More preferably, one of the reporter molecule and the quencher molecule is located at the 5'-end of the TD probe and the other located at a site of the 3'-first hybridization portion.

The TD probe of the present invention has a wide variety of applications for target sequence detection as follows:

I. Target Detection Process by 5' to 3' Exonucleolytic Reaction in a Liquid Phase or on a Solid Phase 1. Target Detection Process in a Liquid Phase The TD probe of the present invention exhibits excellent performance in target sequence detection.

In another aspect of the present invention, there is provided a method for detecting a target nucleic acid sequence from a DNA or a mixture of nucleic acids using a target discriminative probe (TD probe), which comprises the steps of:

(a) hybridizing the target nucleic acid sequence with the TD probe having a hybridizing nucleotide sequence complementary to the target nucleic acid sequence; wherein the TD probe has a modified dual specificity oligonucleotide (mDSO) structure represented by the following general formula I:

$$5'\text{-}X'_p\text{—}Y'_q\text{—}Z'_r\text{-}3' \qquad (I)$$

wherein, $X'_p$ represents a 5'-second hybridization portion having a hybridizing nucleotide sequence complementary to the target nucleic acid sequence; $Y'_q$ represents a separation portion comprising at least three universal bases, $Z'_r$ represents a 3'-first hybridization portion having a hybridizing nucleotide sequence complementary to the target nucleic acid sequence; the TD probe is dually labeled with a fluorescent reporter molecule and a quencher molecule capable of quenching the fluorescence of the reporter molecule; at least one of the reporter molecule and the quencher molecule is positioned on the 5'-second hybridization portion; p, q and r represent the number of nucleotides; and X, Y' and Z' are deoxyribonucleotides or ribonucleotides; the $T_m$ of the 5'-second hybridization portion is lower than that of the 3'-first hybridization portion and the separation portion has the lowest $T_m$ in the three portions of $X'_p$, $Y'_q$ and $Z'_r$; the separation portion separates the 5'-second hybridization portion from the 3'-first hybridization portion in terms of hybridization events to the target nucleic acid sequence, whereby the hybridization specificity of the TD probe is determined dually by the 5'-second hybridization portion and the 3'-first hybridization portion such that the overall hybridization specificity of the TD probe is enhanced;

wherein when the TD probe is hybridized with the target nucleic acid sequence, both of the 5'-second hybridization portion and the 3'-first hybridization portion are hybridized with the target nucleic acid sequence and the 5'-second hybridization portion is digested by an enzyme having a 5' to 3' exonuclease activity; wherein when the TD probe is hybridized with the non-target nucleic acid sequence, both the 5'-second hybridization portion and the separation portion form a single strand such that the 5'-second hybridization portion is not digested by the enzyme having the 5' to 3' exonuclease activity, whereby the TD probe allows discriminating the target nucleic acid sequence from the non-target nucleic acid sequence;

(b) contacting the resultant of step (a) to the enzyme having the 5' to 3' exonuclease activity; wherein when the TD probe is hybridized with the target nucleic acid sequence, the 5'-second hybridization portion is digested by the enzyme having the 5' to 3' exonuclease activity to separate the fluorescent reporter molecule from the quencher molecule on the TD probe, resulting in generation of a fluorescence signal; wherein when the TD probe is hybridized with the non-target nucleic acid sequence, the 5'-second hybridization portion is not digested by the enzyme having the 5' to 3' exonuclease activity, resulting in no fluorescence signal; and (c) detecting the fluorescence signal, such that the fluorescence signal generated by the digestion on the 5'-second hybridization portion is indicative of the presence of the target nucleic acid sequence.

In accordance with the present invention, the TD probe is hybridized with the target nucleic acid sequence.

In accordance with the present invention, the target nucleic acid sequence may be detected only using the TD probe and the enzyme having the 5' to 3' exonuclease activity without false positive signals, which is first proposed by the present inventors.

As represented in FIG. 1, the TD probe exhibits distinctly different hybridization behaviors for each of target and non-target nucleic acid sequences. When the TD probe is hybridized with the target nucleic acid sequence, both the 5'-second hybridization portion and the 3'-first hybridization portion of the TD probe form a double strand with the target nucleic acid sequence. In contrast, where the TD probe is hybridized with a non-target nucleic acid sequence (i.e., non-target hybridization or binding), its 3'-first hybridization portion prevailingly binds to the non-target nucleic acid sequence but both the 5'-second hybridization portion and the separation portion of the TD probe are not hybridized with the non-target nucleic acid sequence such that both portions form a single strand.

Consequently, where the TD probe is hybridized with the target nucleic acid sequence, its 5'-second hybridization portion is digested by the enzyme having the 5' to 3' exonuclease activity (e.g., a template-dependent nucleic acid polymerase having a 5' to 3' exonuclease activity) and the fluorescent reporter molecule and the quencher molecule are separated from each other to generate the fluorescence signal for the target nucleic acid sequence. Generally, the digestion of the TD probe occurs initially at its 5'-end and subsequently in a 5' to 3'-direction.

In contrast, where the TD probe is hybridized with a non-target nucleic acid sequence, both the 5'-second hybridization portion and the separation portion form a single strand which is not digested by the 5' to 3' exonuclease activity of the enzyme. Finally, the TD probe generates no signals on non-target hybridization.

By such unique hybridization behaviors of the TD probe, the target nucleic acid sequence may be detected only using the TD probe and the enzyme having the 5' to 3' exonuclease activity without false signals.

According to a preferred embodiment, the enzyme having the 5' to 3' exonuclease activity used acts only on the 5'-end of double strand nucleic acids and catalyzes exonucleolytic reaction in a 5' to 3' direction, with no digesting single strand nucleic acids.

According to a preferred embodiment, the enzyme having the 5' to 3' exonuclease activity is a thermostable enzyme. According to a preferred embodiment, the enzyme having the 5' to 3' exonuclease activity is a template-dependent nucleic acid polymerase, more preferably a thermostable template-dependent nucleic acid polymerase.

According to a preferred embodiment, the fluorescent reporter molecule and the quencher molecule each is positioned on each different portion of the 5'-second hybridization portion and the 3'-first hybridization portion. For example, the fluorescent reporter molecule may be positioned on the 5'-second hybridization portion and the quencher molecule on the 3'-first hybridization portion. Alternatively, the quencher molecule may be positioned on the 5'-second hybridization portion and the fluorescent reporter molecule on the 3'-first hybridization portion.

According to a preferred embodiment, the fluorescent reporter molecule and the quencher molecule all are positioned on the 5'-second hybridization portion or the reporter molecule and the quencher molecule each is positioned on each different portion of the 5'-second hybridization portion and the separation portion. Most preferably, the fluorescent reporter molecule and the quencher molecule all are positioned on the 5'-second hybridization portion of the TD probe.

It is known that some enzymes (including template-dependent nucleic acid polymerases) having the 5' to 3' exonuclease activity have also the endonuclease activity that is generally very low. The extent of the endonuclease activity may be affected by (i) types of enzymes, (ii) reaction conditions such as temperate, reaction time and reaction composition, (iii) length, sequence and 5' mismatch sequence length of probes or (iv) target sequences. According to a preferred embodiment, where the present method uses enzymes having both 5' to 3' exonuclease activity and endonuclease activity, it is carried out under conditions sufficient to shield the endonuclease activity. Preferably, the present invention is performed using enzymes having 5' to 3' exonuclease activity and little or no endonuclease activity.

Therefore, the endonuclease activity is not a considerable factor in target detection using TD probes with an enzyme having 5' to 3' exonuclease activity and endonuclease activity. However, for more definite target detection, a blocker may be incorporated into the 3'-first hybridization portion of the TD probe to block a endonuclease activity-catalyzed digestion of the 3'-first hybridization portion of TD probe hybridized with a non-target nucleic acid sequence. Particularly when TD probe is used in a liquid phase, the fluorescent reporter molecule and the quencher molecule all may be positioned on the 5'-second hybridization portion of the TD probe for more definite target detection.

In the present invention, the enzyme having a 5' to 3' exonuclease activity generally includes enzymes having a 5' to 3' exonuclease activity and usually includes enzymes having an additional endonuclease activity as well as the 5' to 3' exonuclease activity. In the present invention, the template-dependent nucleic acid polymerase having a 5' to 3' exonuclease activity generally includes nucleic acid polymerases having a 5' to 3' exonuclease activity and usually includes nucleic acid polymerases having an additional endonuclease activity as well as the 5' to 3' exonuclease activity.

According to a preferred embodiment, the TD probe comprises at least one label on any site of a sequence comprising 1-10 nucleotides from its 5'-end, still more preferably, any site of a sequence comprising 1-5 nucleotides from its 5'-end, still much more preferably, any site of a sequence comprising 1-3 nucleotides from its 5'-end. Most preferably, the TD probe comprises at least one label at its 5'-end.

According to a preferred embodiment, the step (a) is carried out using the TD probe together with an upstream primer to be hybridized with a site downstream of a hybridized site of the TD probe and the enzyme having the 5' to 3' exonuclease activity is a template-dependent nucleic acid polymerase having the 5' to 3' exonuclease activity such that the upstream primer is extended by the template-dependent nucleic acid polymerase in the step (b).

Following the hybridization, the upstream primer hybridized with the target nucleic acid sequence is extended by the polymerase activity of the template-dependent nucleic acid polymerase and the TD probe is digested by the 5' to 3' exonuclease activity to separate the fluorescent reporter molecule and the quencher molecule, generating the fluorescence signal.

According a preferred embodiment, the step (a) is carried out using the TD probe together with a reverse primer and the enzyme having the 5' to 3' exonuclease activity is a template-dependent nucleic acid polymerase having the 5' to 3' exonuclease activity such that the step (b) produces the target nucleic acid sequence hybridizable with the TD probe by an extension reaction of the reverse primer by the template-dependent nucleic acid polymerase.

The reverse primer produces additional target nucleic acid sequences to be hybridized with the TD probe, resulting in obtaining more evident and higher fluorescence signals indicative of target nucleic acid sequences.

The reporter molecule and the quencher molecule useful in the present invention may be fluorescent materials. Reporter molecules and quencher molecules known in the art are useful in this invention. Examples of those are: Cy2™ (506), YO-PRO™-1 (509), YOYO™-1 (509), Calcein (517), FITC (518), FluorX™ (519), Alexa™ (520), Rhodamine 110 (520), Oregon Green™ 500 (522), Oregon Green™ 488 (524), RiboGreen™ (525), Rhodamine Green™ (527), Rhodamine 123 (529), Magnesium Green™ (531), Calcium Green™ (533), TO-PRO™-1 (533), TOTO1 (533), JOE (548), BODIPY530/550 (550), Dil (565), BODIPY TMR (568), BODIPY558/568 (568), BODIPY564/570 (570), Cy3™ (570), Alexa™ 546 (570), TRITC (572), Magnesium Orange™ (575), Phycoerythrin R&B (575), Rhodamine Phalloidin (575), Calcium Orange™ (576), Pyronin Y (580), Rhodamine B (580), TAMRA (582), Rhodamine Red™ (590), Cy3.5™ (596), ROX (608), Calcium Crimson™ (615), Alexa™ 594 (615), Texas Red (615), Nile Red (628), YO-PRO™-3 (631), YOYO™-3 (631), R-phycocyanin (642), C-Phycocyanin (648), TO-PRO™-3 (660), TOTO3 (660), DiD DilC (5) (665), Cy5™ (670), Thiadicarbocyanine (671), Cy5.5 (694), HEX (556), TET (536), Biosearch Blue (447), CAL Fluor Gold 540 (544), CAL Fluor Orange 560 (559), CAL Fluor Red 590 (591), CAL Fluor Red 610 (610), CAL Fluor Red 635 (637), FAM (520), Fluorescein (520), Fluorescein-C3 (520), Pulsar 650 (566), Quasar 570 (667), Quasar 670 (705) and Quasar 705 (610). The numeric in parenthesis is a maximum emission wavelength in nanometer.

Suitable pairs of reporter-quencher are disclosed in a variety of publications as follows: Pesce et al., editors, Fluorescence Spectroscopy (Marcel Dekker, New York, 1971); White et al., Fluorescence Analysis: A Practical Approach (Marcel Dekker, New York, 1970); Berlman, Handbook of Fluorescence Spectra of Aromatic Molecules, $2^{nd}$ Edition (Academic Press, New York, 1971); Griffiths, Color AND Constitution of Organic Molecules (Academic Press, New York, 1976); Bishop, editor, Indicators (Pergamon Press, Oxford, 1972); Haugland, Handbook of Fluorescent Probes and Research Chemicals (Molecular Probes, Eugene, 1992); Pringsheim, Fluorescence and Phosphorescence (Interscience Publishers, New York, 1949); Haugland, R. P., Handbook of Fluorescent Probes and Research Chemicals, $6^{th}$ Edition, Molecular Probes, Eugene, Oreg., 1996; U.S. Pat. Nos. 3,996,345 and 4,351,760.

It is noteworthy that a non-fluorescent black quencher molecule capable of quenching a fluorescence of a wide range of wavelengths or a specific wavelength may be used in the present invention. Examples of those are BHQ and DABCYL.

In the FRET label adapted to the TD probe, the reporter encompasses a donor of FRET and the quencher encompasses the other partner (acceptor) of FRET. For example, a fluorescein dye is used as the reporter and a rhodamine dye as the quencher.

The term used herein "target nucleic acid", "target nucleic acid sequence" or "target sequence" refers to a nucleic acid sequence of interest for detection, which is annealed to or hybridized with a primer or probe under hybridization, annealing or amplifying conditions.

The term used herein "probe" refers to a single-stranded nucleic acid molecule comprising a portion or portions that are substantially complementary to a target nucleic acid sequence. The probes of this invention may be comprised of naturally occurring dNMP (i.e., dAMP, dGM, dCMP and dTMP), modified nucleotide, or non-natural nucleotide. The probes may also include ribonucleotides.

Preferably, the 3'-end of the labeled probe is blocked to prohibit extension of the probe. Blocking can be achieved by using non-complementary bases or by adding a chemical moiety such as biotin or a phosphate group to the 3' hydroxyl of the last nucleotide. Blocking can also be achieved by removing the 3'-OH or by using a nucleotide that lacks a 3'-OH such as a dideoxynucleotide.

The term "primer" as used herein refers to an oligonucleotide, which is capable of acting as a point of initiation of synthesis when placed under conditions in which synthesis of primer extension product which is complementary to a nucleic acid strand (template) is induced, i.e., in the presence of nucleotides and an agent for polymerization, such as DNA polymerase, and at a suitable temperature and pH. The primer is preferably single stranded for maximum efficiency in amplification. Preferably, the primer is an oligodeoxyribonucleotide. The primer of this invention may be comprised of naturally occurring dNMP (i.e., dAMP, dGM, dCMP and dTMP), modified nucleotide, or non-natural nucleotide. The primer may also include ribonucleotides.

The primer must be sufficiently long to prime the synthesis of extension products in the presence of the agent for polymerization. The exact length of the primers will depend on many factors, including temperature, application, and source of primer. The term "annealing" or "priming" as used herein refers to the apposition of an oligodeoxynucleotide or nucleic acid to a template nucleic acid, whereby the apposition enables the polymerase to polymerize nucleotides into a nucleic acid molecule which is complementary to the template nucleic acid or a portion thereof.

The term used "hybridizing" used herein refers to the formation of a double-stranded nucleic acid from complementary single stranded nucleic acids. There is no intended distinction between the terms "annealing" and "hybridizing", and these terms will be used interchangeably.

The annealing or hybridization of the TD probe may be a wide variety of hybridization processes known to those of skill in the art. The suitable hybridization conditions in the present invention may be routinely determined by optimization procedures. Conditions such as temperature, concentration of components, hybridization and washing time, buffer components, and their pH and ionic strength may be varied depending on various factors, including the length and GC content of oligonucleotides such as probes and target nucleic acid sequences. The detailed conditions for hybridization can be found in Joseph Sambrook, et al., *Molecular Cloning, A Laboratory Manual*, Cold Spring Harbor Laboratory Press, Cold Spring Harbor, N.Y. (2001); and M. L. M. Anderson, *Nucleic Acid Hybridization*, Springer-Verlag New York Inc. N.Y. (1999).

According to a preferred embodiment, the hybridization temperature of the TD probe ranges from about 40° C. to 80° C., more preferably 45° C. to 75° C., still more preferably 50° C. to 72° C.

The term used herein "upstream primer" refers to a primer to be hybridized with a site downstream of a hybridized site of the TD probe and to form a complementary sequence to the target nucleic acid sequence with help of the template-dependent nucleic acid polymerase.

The TD probe, the upstream primer and the reverse primer each has a hybridizing nucleotide sequence complementary to the target nucleic acid sequence. The term "complementary" is used herein to mean that primers or probes are sufficiently complementary to hybridize selectively to a target nucleic acid sequence under the designated annealing conditions or stringent conditions, encompassing the terms "substantially complementary" and "perfectly complementary", preferably perfectly complementary.

According to a preferred embodiment, the 5'-second hybridization portion of the TD probe is complementary to the target nucleic acid sequence. In other words, the 5'-second hybridization portion may have a perfectly match sequence or imperfectly match sequence to the target nucleic acid sequence. If necessary, the 5'-second hybridization portion may be designed to have some mismatch nucleotides.

According to a specific embodiment of this invention, the 5'-second hybridization portion of the TD probe may have one to three additional mismatch nucleotides at its 5'-end. Among enzymes (e.g., nucleic acid polymerases) having 5' to 3' exonuclease activity, there have been reported enzymes to be capable of digesting one to three nucleotides from the 5'-end of oligonucleotides hybridized with target sequences (see Murante et al, Journal of Biological Chemistry Vol. 269. 1191-1196 (1994) and Example 1). Where such enzymes are used, the TD probe may be constructed to have one to three artificial mismatch nucleotides at its 5'-end.

The target nucleic acid sequence to be detected in the present invention includes any nucleic acid molecule, e.g., DNA (gDNA and cDNA) and RNA. The target nucleic acid sequence includes any naturally occurring procaryotic, eukaryotic (for example, protozoans and parasites, fungi, yeast, higher plants, lower and higher animals, including mammals and humans) or viral (for example, Herpes viruses, HIV, influenza virus, Epstein-Barr virus, hepatitis virus, polio virus, etc.) or viroid nucleic acid.

The target nucleic acid sequences in a sample may be either DNA or RNA. The molecule may be in either a double-stranded or single-stranded form. Where the nucleic acid as starting material is double-stranded, it is preferred to render the two strands into a single-stranded or partially single-stranded form. Methods known to separate strands includes, but not limited to, heating, alkali, formamide, urea and glycoxal treatment, enzymatic methods (e.g., helicase action), and binding proteins. For instance, strand separation can be achieved by heating at temperature ranging from 80° C. to 105° C. General methods for accomplishing this treatment are provided by Joseph Sambrook, et al., Molecular Cloning, A Laboratory Manual, Cold Spring Harbor Laboratory Press, Cold Spring Harbor, N.Y. (2001).

Where a mRNA is employed as starting material, a reverse transcription step is necessary prior to performing annealing step, details of which are found in Joseph Sambrook, et al., Molecular Cloning, A Laboratory Manual, Cold Spring Harbor Laboratory Press, Cold Spring Harbor, N.Y. (2001); and Noonan, K. F. et al., Nucleic Acids Res. 16:10366 (1988)). For reverse transcription, a random hexamer or an oligonucleotide dT primer hybridizable to poly A tail of mRNA is used. The oligonucleotide dT primer is comprised of dTMPs, one or more of which may be replaced with other dNMPs so long as the dT primer can serve as primer. Reverse transcription can be done with reverse transcriptase that has RNase H activity. If one uses an enzyme having RNase H activity, it may be possible to omit a separate RNase H digestion step by carefully choosing the reaction conditions.

The probes or primers used in the present invention are hybridized or annealed to sites on target nucleic acid sequences (as templates) that double-stranded structure is formed. Conditions of nucleic acid hybridization or annealing suitable for forming such double stranded structures are described by Joseph Sambrook, et al., Molecular Cloning, A Laboratory Manual, Cold Spring Harbor Laboratory Press, Cold Spring Harbor, N.Y. (2001) and Haymes, B. D., et al., Nucleic Acid Hybridization, A Practical Approach, IRL Press, Washington, D.C. (1985).

According to a preferred embodiment, the upstream primer and/or the reverse primer has a dual specificity oligonucleotide (DSO) structure represented by the following general formula II:

$$5'\text{-}X_p\text{-}Y_q\text{-}Z_r\text{-}3' \tag{II}$$

wherein, Xp represents a 5'-first hybridization portion having a hybridizing nucleotide sequence complementary to the target nucleic acid; Yq represents a separation portion comprising at least three universal bases, Zr represents a 3'-second hybridization portion having a hybridizing nucleotide sequence complementary to the target nucleic acid; p, q and r represent the number of nucleotides, and X, Y, and Z are deoxyribonucleotides or ribonucleotides; the Tm of the 5'-first hybridization portion is higher than that of the 3'-second hybridization portion and the separation portion has the lowest Tm in the three portions; the separation portion separates the 5'-first hybridization portion from the 3'-second hybridization portion in terms of hybridization events to the target nucleic acid, whereby the hybridization specificity of the oligonucleotide are determined dually by the 5'-first hybridization portion and the 3'-second hybridization portion such that the overall hybridization specificity of the oligonucleotide is enhanced.

The descriptions of the DSO structure can be made with reference to those of the mDSO structure.

Preferably, in the DSO structure the 5'-first hybridization portion is longer than the 3'-second hybridization portion. The 5'-first hybridization portion is preferably 15-60 nucleotides, more preferably 15-40 nucleotides, still more preferably 15-25 nucleotides in length. It is preferable that the 3'-second hybridization portion is 3-15 nucleotides, more preferably 5-15 nucleotides, still more preferably 6-13 nucleotides in length. The separation portion is preferably 3-10 nucleotides, more preferably 4-8 nucleotides, most preferably 5-7 nucleotides in length. According to a preferred embodiment, the $T_m$ of the 5'-first hybridization portion ranges from 40° C. to 80° C., more preferably 45° C. to 65° C. The $T_m$ of the 3'-second hybridization portion ranges preferably from 10° C. to 40° C. It is preferable that the $T_m$ of the separation portion ranges from 3° C. to 15° C.

Preferably, the enzyme having the 5' to 3' exonuclease activity and the template-dependent nucleic acid polymerase having the 5' to 3' exonuclease activity used in the present invention may include any template-dependent nucleic acid polymerase having the 5' to 3' exonuclease activity (e.g., *E coli* DNA polymerase I, a thermostable DNA polymerase and bacteriophage T7 DNA polymerase), most preferably a thermostable DNA polymerase obtained from a variety of bacterial species, including *Thermus aquaticus* (Taq), *Thermus thermophilus, Thermus filiformis, Thermus flavus, Thermus antranikianii, Thermus caldophilus, Thermus chliarophilus, Thermus igniterrae, Thermus lacteus, Thermus oshimai, Thermus ruber, Thermus rubens, Thermus scotoductus, Thermus silvans, Thermus* species Z05 and *Thermus* species sps 17 Most preferably, the template-dependent nucleic acid polymerase having the 5' to 3' exonuclease activity is Taq DNA polymerase.

By the enzyme having the 5' to 3' exonuclease activity (preferably, the template-dependent nucleic acid polymerase having the 5' to 3' exonuclease activity), the TD probe is cleaved and the signal indicative of the target nucleic acid sequence is generated. The signal may be detected or measured by conventional methods for each label. For example, the fluorescence signal may be detected or measured by conventional methods, e.g., fluorometers.

The term "signal generation" or "generation of signal" is used herein to encompass a change in fluorescent signal intensity, including not only increase in fluorescent signal intensity but also decrease in fluorescent signal intensity. According to a preferred embodiment, the signal indicative of the presence of the target nucleic acid sequence to be detected is a signal from the fluorescent reporter molecule. Alternatively, the quencher molecule is fluorescent and the signal indicative of the presence of the target nucleic acid sequence to be detected is a signal from the fluorescent quencher molecule.

When the TD probe is hybridized with the non-target nucleic acid sequence, the 5'-second hybridization portion is not digested by the enzyme having the 5' to 3' exonuclease activity, resulting in no fluorescence signal.

The term "no fluorescence signal" refers to no fluorescence signal as well as negligible fluorescence signal. For example, the term encompasses fluorescence intensity generally measured or observed from negative control or background.

According to a preferred embodiment, the present invention further comprises repeating the steps (a)-(b) or (a)-(c), and for the repetition of the steps (a)-(b) or (a)-(c), the present invention further comprise denaturation between repeating cycles.

Methods for denaturation includes, but not limited to, heating, alkali, formamide, urea and glycoxal treatment, enzymatic methods (e.g., helicase action) and binding proteins. For instance, the denaturation may be achieved by heating at temperature ranging from 80° C. to 105° C. General methods for accomplishing this treatment are provided by Joseph Sambrook, et al., Molecular Cloning, A Laboratory Manual, Cold Spring Harbor Laboratory Press, Cold Spring Harbor, N.Y. (2001).

The repetition permits to increase intensity of the fluorescence signal from the fluorescent reporter molecule. In particular, the repetition in the present method using reverse primers permits to increase amounts of the target nucleic acid sequence, contributing to increase in intensity of the fluorescence signal from the fluorescent reporter molecule.

According to a preferred embodiment, the target nucleic acid sequence used is a pre-amplified nucleic acid sequence by an amplification primer.

The pre-amplified target nucleic acid sequence may include a target nucleic acid sequence pre-amplified in other reaction environment (or reaction vessel) than a reaction environment (or reaction vessel) for the steps (a)-(c).

Where the present invention further comprises repeating the steps (a)-(b) or (a)-(c), it is preferred that the signal detection is performed for each cycle of the repetition (i.e., real-time manner), at the end of the repetition (i.e., end-point manner) or at each of predetermined time intervals during the repetition. Preferably, the signal detection may be performed for each cycle of the repetition to improve the detection accuracy.

According to a preferred embodiment, the amplification primer (e.g., including a forward primer and a reverse primer) for production of pre-amplified target nucleic acid sequences has a dual specificity oligonucleotide (DSO) structure represented by the general formula II described above.

According to a preferred embodiment, the TD probe has a blocker site containing as a blocker at least one nucleotide resistant to cleavage by an enzyme having a 5' to 3' exonuclease activity. According to a preferred embodiment, the blocker site is positioned at a site of the TD probe cleaved by the enzyme having the 5' to 3' exonuclease activity and preferably at 3'-hybridization portion of the TD probe.

When an enzyme having a 5' to 3' exonuclease and endonuclease activities (e.g. a template-dependent nucleic acid polymerase having a 5' to 3' exonuclease and endonuclease activities) is used, for more definite target detection, a blocker may be incorporated into the 3'-first hybridization portion of a TD probe to block the endonuclease activity-catalyzed digestion of the 3'-first hybridization portion of the TD probe hybridized with a non-target nucleic acid sequence.

According to a preferred embodiment, the TD probe has a blocker site containing as a blocker at least one nucleotide resistant to cleavage by an enzyme having a 5' to 3' exonuclease activity and the blocker site is positioned at a site to be cleaved by the enzyme having the 5' to 3' exonuclease activity when the TD probe is hybridized with the non-target nucleic acid sequence; wherein when the TD probe having the blocker site is hybridized with the target nucleic acid sequence, its 5'-second hybridization portion is digested by the enzyme having the 5' to 3' exonuclease activity to separate the fluorescent reporter molecule from the quencher molecule on the TD probe, resulting in generation of the fluorescence signal; wherein when the TD probe having the blocker site is hybridized with the non-target nucleic acid sequence, it is not digested by the enzyme having an exonuclease activity to generate no fluorescence signal.

According to a preferred embodiment, the blocker site of the TD probe is positioned on the 3'-first hybridization portion of the TD probe. More preferably, the blocker site of the TD probe is positioned on the 3'-first hybridization portion adjacent to the 3'-end of the separation portion.

According to a preferred embodiment, the blocker site comprises 1-15 blockers, more preferably 2-10 blockers, still more preferably 3-5 blockers.

Nucleotides serving as blockers, i.e., those having a backbone resistant to cleavage by an enzyme having a 5' to 3' exonuclease activity include any one known to one of skill in the art. For example, they include various phosphorothioate linkages, phosphonate linkages, phosphoroamidate linkages and 2'-carbohydrates modifications. According to a preferred embodiment, nucleotides having a backbone resistant to cleavage by an enzyme having a 5' to 3' exonuclease activity include phosphorothioate linkage, alkyl phosphotriester linkage, aryl phosphotriester linkage, alkyl phosphonate linkage, aryl phosphonate linkage, hydrogen phosphonate linkage, alkyl phosphoroamidate linkage, aryl phosphoroamidate linkage, phosphoroselenate linkage, 2'-O-aminopropyl modification, 2'-O-alkyl modification, 2'-O-allyl modification, 2'-O-butyl modification, α-anomeric oligodeoxynucleotide and 1-(4'-thio-β-D-ribofuranosyl) modification. The blocker nucleotide present in the TD probe may be one or more in continuous or intermittent manner.

According to a preferred embodiment, the target nucleic acid sequence comprises at least two types (more preferably, at least three types, still more preferably at least five types) of nucleic acid sequences and the TD probe comprises at least two types (more preferably, at least three types, still more preferably at least five types) of probes.

According to a preferred embodiment, the target nucleic acid sequence comprises at least two types (more preferably, at least three types, still more preferably at least five types) of nucleic acid sequences, the TD probe comprises at least two types (more preferably, at least three types, still more preferably at least five types) of probes and the upstream primer comprises at least two types (more preferably, at least three types, still more preferably at least five types) of primers.

According to a preferred embodiment, the target nucleic acid sequence comprises at least two types (more preferably, at least three types, still more preferably at least five types) of nucleic acid sequences, the TD probe comprises at least two types (more preferably, at least three types, still more preferably at least five types) of probes and the reverse primer comprises at least two types (more preferably, at least three types, still more preferably at least five types) of primers.

Furthermore, the present invention is very useful in detection of a nucleotide variation. The term "nucleotide variation" used herein refers to a nucleotide polymorphism in a DNA sequence at a particular location among contiguous DNA segments that are otherwise similar in sequence. Such contiguous DNA segments include a gene or any other portion of a chromosome. For example, the nucleotide variation detected in the present invention includes SNP (single nucleotide polymorphism), deletion, insertion, substitution and translocation. Exemplified nucleotide variation includes numerous variations in a human genome (e.g., variations in the MTHFR (methylenetetrahydrofolate reductase) gene), variations involved in drug resistance of pathogens and tumorigenesis-causing variations.

According to a preferred embodiment, the nucleotide variation on the target nucleic acid sequence is present at a site opposite to the 5'-second hybridization portion of a TD probe.

2. Target Detection Process On a Solid phase

The present invention has excellent adaptability on a solid phase (e.g., microarray) as well as in a liquid phase.

In another aspect of this invention, there is provided a method for detecting a target nucleic acid sequence on a solid phase from a DNA or a mixture of nucleic acids using a target discriminative probe (TD probe), which comprises the steps of:

(a) hybridizing the target nucleic acid sequence with the TD probe having a hybridizing nucleotide sequence complementary to the target nucleic acid sequence; wherein the TD probe is immobilized through its 3'-end on the surface of the solid substrate; wherein the TD probe has a modified dual specificity oligonucleotide (mDSO) structure represented by the following general formula I:

 (I)

wherein, $X'_p$ represents a 5'-second hybridization portion having a hybridizing nucleotide sequence complementary to the target nucleic acid sequence; $Y'_q$ represents a separation portion comprising at least three universal bases, $Z'_r$ represents a 3'-first hybridization portion having a hybridizing nucleotide sequence complementary to the target nucleic acid sequence; the TD probe has a label generating a detectable signal and the label is positioned on the 5'-second hybridization portion of the TD probe; p, q and r represent the number of nucleotides; and X, Y' and Z' are deoxyribonucleotides or ribonucleotides; the $T_m$ of the 5'-second hybridization portion is lower than that of the 3'-first hybridization portion and the separation portion has the lowest $T_m$ in the three portions of $X'_p$, $Y'_q$ and $Z'_r$; the separation portion separates the 5'-second hybridization portion from the 3'-first hybridization portion in terms of hybridization events to the target nucleic acid sequence, whereby the hybridization specificity of the TD probe are determined dually by the 5'-second hybridization portion and the 3'-first hybridization portion such that the overall hybridization specificity of the TD probe is enhanced;

wherein when the TD probe is hybridized with the target nucleic acid sequence, both of the 5'-second hybridization portion and the 3'-first hybridization portion are hybridized with the target nucleic acid sequence and the 5'-second hybridization portion is digested by the enzyme having the 5' to 3' exonuclease activity; wherein when the TD probe is hybridized with the non-target nucleic acid sequence, both the 5'-second hybridization portion and the separation portion form a single strand such that the 5'-second hybridization portion is not digested by the enzyme having the 5' to 3' exonuclease activity, whereby the TD probe allows discriminating the target nucleic acid sequence from the non-target nucleic acid sequence;

(b) contacting the resultant of step (a) to the enzyme having the 5' to 3' exonuclease activity; wherein when the TD probe is hybridized with the target nucleic acid sequence, its 5'-second hybridization portion is digested by the enzyme having the 5' to 3' exonuclease activity to release the label from the TD probe, resulting in a signal change on the TD probe immobilized on the solid substrate; wherein when the TD probe is hybridized with the non-target nucleic acid sequence, the 5'-second hybridization portion is not digested by the enzyme having the 5' to 3' exonuclease activity, resulting in no signal change, whereby the signal change on the solid substrate is detected to determine the presence of the target nucleic acid sequence; and (c) detecting the signal change on the solid substrate, such that the signal change by the digestion on the 5'-second hybridization portion is indicative of the presence of the target nucleic acid sequence.

Since the process of the present invention on the solid phase uses the TD probe and follows the steps of the present method described in the liquid phase, the common descriptions between them are omitted in order to avoid undue redundancy leading to the complexity of this Specification.

For the solid phase reaction, the TD probe may be immobilized directly or indirectly (preferably indirectly) through its 3'-end onto the surface of the solid substrate. Furthermore, the probes may be immobilized on the surface of the solid substrate in a covalent or non-covalent manner. Where the immobilized probes are immobilized onto the surface of the solid substrate, suitable linkers are used. The linkers useful in this invention may include any linkers utilized for probe immobilization on a microarray. For example, alkyl, or aryl compounds with amine functionality, or alkyl or aryl compounds with thiol functionality serve as linkers for probe immobilization. In addition, poly (T) bases or poly (A) bases may be used as a linker to minimize the space hindrance for enzymatic reactions (e.g. enzymatic cleavage reactions) or to increase hybridization efficiency. It could be appreciated that the poly (T) bases or poly (A) bases are not considered as a sequence spanning the TD probe. For instance, the poly (T) bases or poly (A) bases linked to the end of the 3'-first hybridization portion of the TD probe are not considered as the 3'-first hybridization portion.

According to a preferred embodiment, the solid substrate used in the present invention is a microarray. The microarray to provide a reaction environment in this invention may include any those known to one of skill in the art. All processes of the present invention, i.e., annealing to target nucleic acid, extension/digestion and fluorescence detection, are carried out on the microarray. The immobilized probes on the microarray serve as hybridizable array elements. The solid substrate to fabricate microarray include, but not limited to, metals (e.g., gold, alloy of gold and copper, aluminum), metal oxide, glass, ceramic, quartz, silicon, semiconductor, Si/SiO$_2$ wafer, germanium, gallium arsenide, carbon, carbon nanotube, polymers (e.g., polystyrene, polyethylene, polypropylene and polyacrylamide), sepharose, agarose and colloids. A plurality of immobilized probes in this invention may be immobilized on an addressable region or two or more addressable regions on a solid substrate that may comprise 2-1,000,000 addressable regions. Immobilized probes may be fabricated to produce array or arrays for a given application by conventional fabrication technologies such as photolithography, ink-jetting, mechanical microspotting, and derivatives thereof.

According to a preferred embodiment, the enzyme having the 5' to 3' exonuclease activity is a thermostable enzyme. According to a preferred embodiment, the enzyme having the 5' to 3' exonuclease activity is a template-dependent nucleic acid polymerase, more preferably a thermostable template-dependent nucleic acid polymerase.

According to a preferred embodiment, the step (a) is carried out using the TD probe together with an upstream primer to be hybridized with a site downstream of a hybridized site of the TD probe and the enzyme having the 5' to 3' exonuclease activity is a template-dependent nucleic acid polymerase having the 5' to 3' exonuclease activity such that the upstream primer is extended by the template-dependent nucleic acid polymerase in the step (b).

According to a preferred embodiment, the step (a) is carried out using the TD probe together with a reverse primer and the enzyme having the 5' to 3' exonuclease activity is a template-dependent nucleic acid polymerase having the 5' to 3' exonuclease activity such that the step (b) produces the target nucleic acid sequence hybridizable with the TD probe by an extension reaction of the reverse primer by the template-dependent nucleic acid polymerase.

According to a preferred embodiment, the label is a chemical label, an enzymatic label, a radioactive label, a fluorescent label, an interactive label, a luminescent label, a chemiluminescent label or a metal label.

Figure 4A:
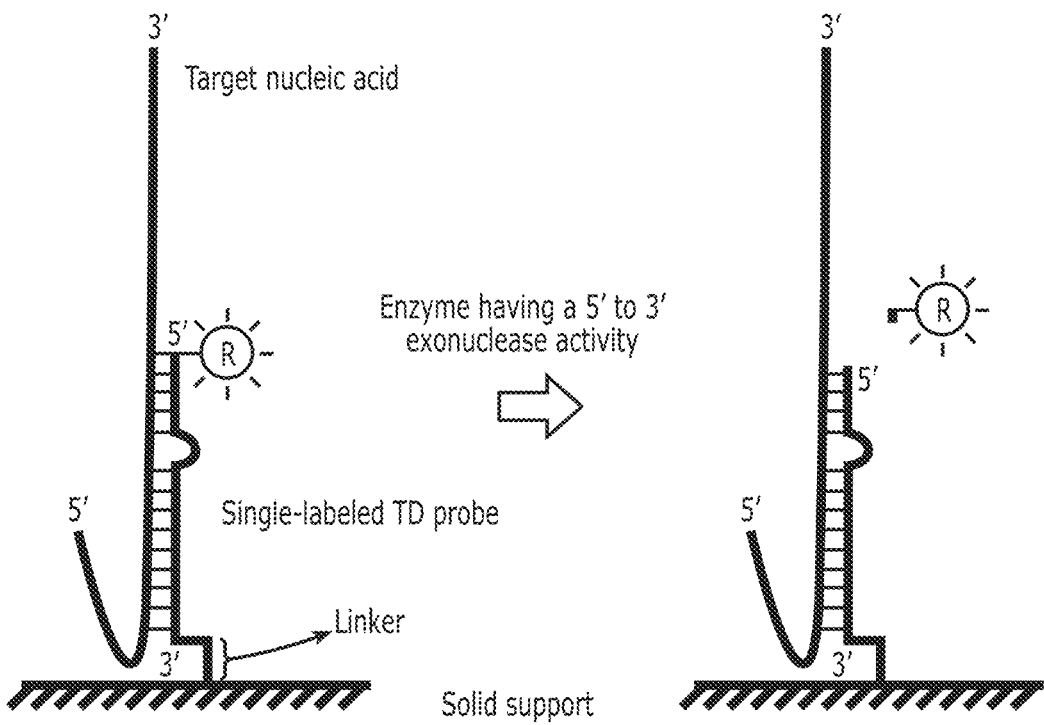
FIGS. 4A and 4B schematically represent the discrimination of a target nucleic acid sequence from a non-target nucleic acid sequence using an immobilized TD probe having a single label and an enzyme having a 5' to 3' exonuclease activity in solid phase.
Figure 4B:
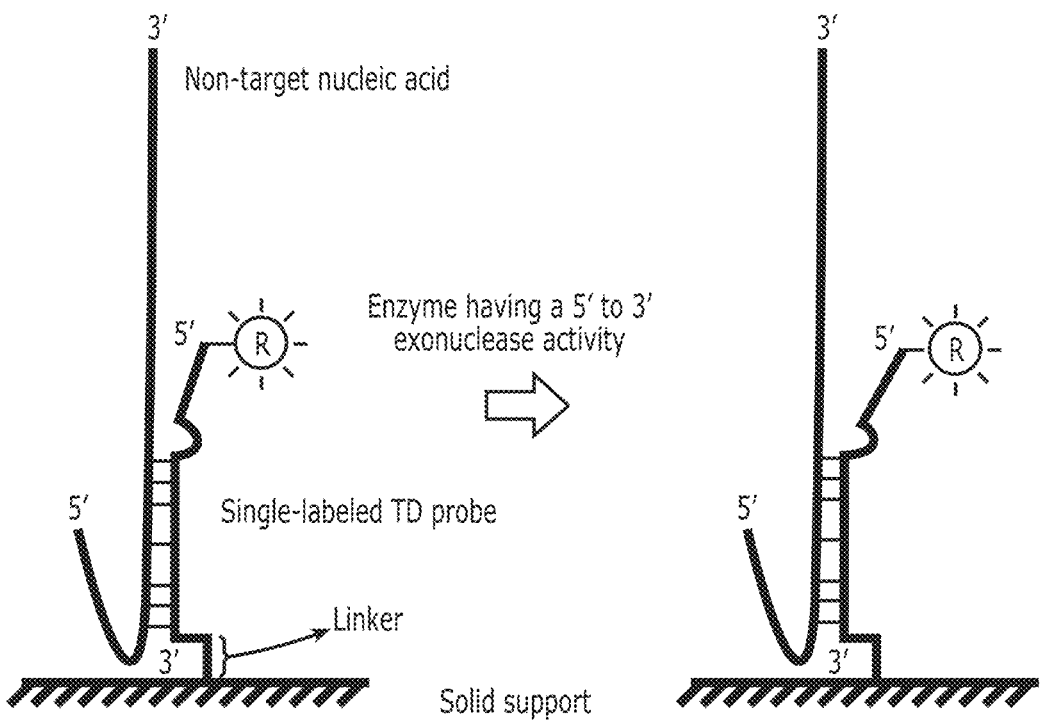
Figure 5A:
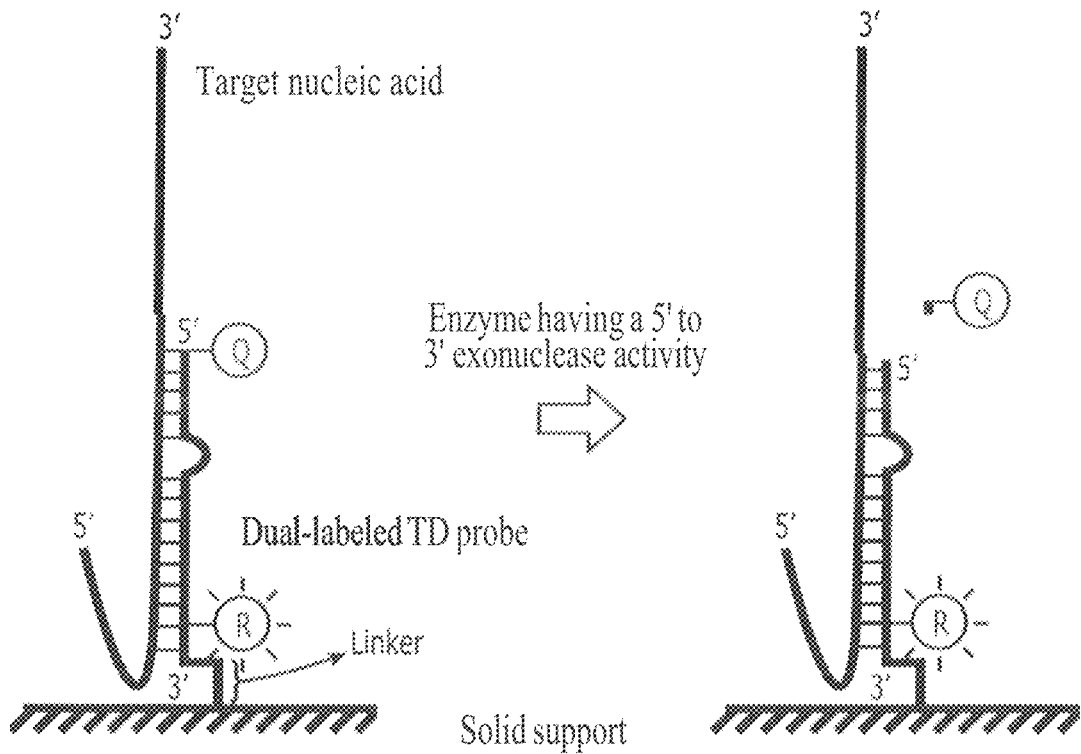
FIGS. 5A and 5B schematically represent the discrimination of a target nucleic acid and a non-target nucleic acid sequence using an immobilized TD probe having dual labels and an enzyme having a 5' to 3' exonuclease activity in solid phase.
Figure 5B:
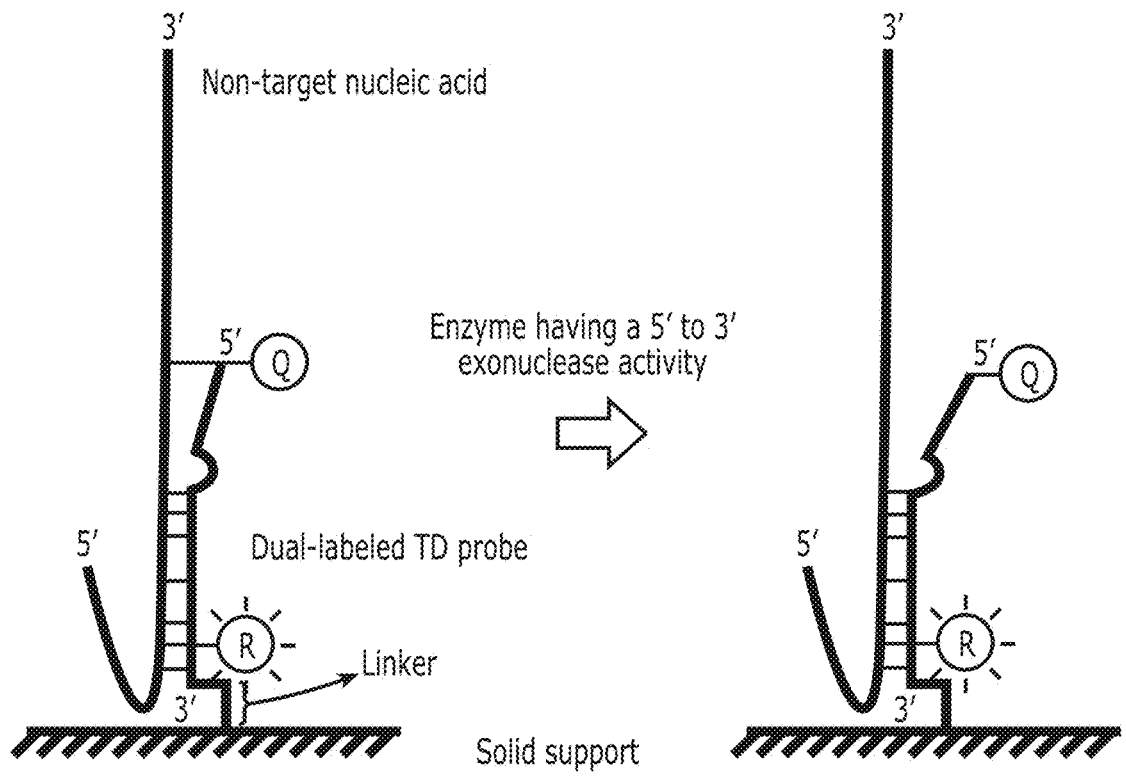

As shown in FIG. 4 or 5, the present method on the solid phase may be carried out using a single label (e.g., a single fluorescent label) or an interactive label (e.g., a reporter molecule and a quencher molecule).

For example, where the TD probe having a single fluorescent label is used for the detection of a target nucleic acid sequence, the fluorescent label on the 5'-second hybridization portion is released from the TD probe immobilized on the solid substrate, leading to decrease in fluorescence signal intensity on the solid substrate. The fluorescence signal decrease or elimination may indicate the presence of the target nucleic acid sequence.

According to a preferred embodiment, where the single label is a fluorescent reporter molecule, the signal change is the decrease or elimination of fluorescence signals on the solid substrate.

According to a preferred embodiment, where the TD probe having a single fluorescent label is used, the washing step is optionally further comprised prior to the detection in the step (c). Alternatively, where the TD probe having a single fluorescent label is used, the washing step is not comprised prior to the detection in the step (c).

According to a preferred embodiment, the single fluorescent molecule is positioned at a site on the 5'-second hybridization portion to be digested by the enzyme having the 5' to 3' exonuclease activity.

For clarity, it should be appreciated that the phrase "a site on the 5'-second hybridization portion to be digested by the enzyme having the 5' to 3' exonuclease activity" means that all, a part or a position of the 5'-second hybridization portion may be digested by the enzyme having the 5' to 3' exonuclease activity and the label may be positioned at any one site to be digested on the 5'-second hybridization portion. Therefore, the phrase "a site on the 5'-second hybridization portion to be digested by the enzyme having the 5' to 3' exonuclease activity" can be written as "a site to be digested by the enzyme having the 5' to 3' exonuclease activity, on the 5'-second hybridization portion".

More preferably, the single fluorescent molecule is positioned on any site of a sequence comprising 1-10 nucleotides from 5'-end, still more preferably, any site of a sequence comprising 1-5 nucleotides from 5'-end, still much more preferably, any site of a sequence comprising 1-3 nucleotides from 5'-end of TD probe. Most preferably, the single fluorescent molecule is positioned on at 5'-end of TD probe.

According to a preferred embodiment, the label is the interactive label system comprising a pair of a fluorescent reporter molecule and a quencher molecule.

According to a preferred embodiment, one of the reporter molecule and the quencher molecule is positioned at a site on the 5'-second hybridization portion of a TD probe and the other on a site not to be digested by the enzyme having the 5' to 3' exonuclease activity.

According to a preferred embodiment, one of the reporter molecule and the quencher molecule is positioned at a site to be digested by the enzyme having the 5' to 3' exonuclease activity, on the 5'-second hybridization portion of the TD probe and the other on a site not to be digested by the enzyme having the 5' to 3' exonuclease activity.

According to a preferred embodiment, the site not to be digested by the enzyme having the 5' to 3' exonuclease activity can exist on the 5'-second hybridization portion, separation portion or 3'-first hybridization portion of a TD probe.

According to a preferred embodiment, where the present method is performed on the solid phase, the TD probe is immobilized through its 3'-end on the surface of a solid substrate; wherein the quencher molecule is positioned at a site on the 5'-second hybridization portion of the TD probe to be digested by the enzyme having the 5' to 3' exonuclease activity and the fluorescent reporter molecule is positioned on a site not to be digested by the enzyme having the 5' to 3' exonuclease activity; wherein when the TD probe is hybridized with the target nucleic acid sequence, its 5'-second hybridization portion is digested by the enzyme having the 5' to 3' exonuclease activity to separate the fluorescent reporter molecule from the quencher molecule on the TD probe, resulting in generation of the fluorescence signal from the reporter molecule; wherein when the TD probe is hybridized with the non-target nucleic acid sequence, the 5'-second hybridization portion is not digested by the enzyme having the 5' to 3' exonuclease activity, resulting in no fluorescence signal, whereby the fluorescent signal on the solid substrate is detected to determine the presence of the target nucleic acid sequence.

Where the immobilized TD probe is hybridized with the target nucleic acid sequence, it is digested by an enzyme having a 5' to 3' exonuclease activity from the 5'-end toward the 3'-end. At this time, the binding between a fragment of the immobilized TD probe and the target nucleic acid becomes weaker, thereby resulting in release of the target nucleic acid from the fragment of the immobilized TD probe on the solid substrate. In this regard, the immobilized probe TD can be considered to have two portions, a digested portion and an undigested portion by the enzyme having a 5' to 3' exonuclease activity. Therefore, the label positioned on the undigested portion of the probe is remained to the surface of the solid substrate.

Given the digestion patterns of the immobilized TD probe, it could be understood that the TD probe may also have a digested portion and an undigested portion within the 5'-second hybridization portion. The formation of the digested portion and undigested portion within the TD probe may be affected by the separation portion.

According to a preferred embodiment, when a blocker such as modified nucleotides or backbones resistant to the 5' to 3' exonuclease activity is incorporated into a site of the TD probe between a quencher molecule and a reporter molecule, the enzyme having the 5' to 3' exonuclease activity is not capable of further digesting the TD probe due to the presence of the blocker such that a single-label containing fragment of the immobilized TD probe as an undigested portion remains on the solid substrate.

According to a preferred embodiment, the quencher molecule is positioned on the 5'-second hybridization portion to be digested by the enzyme having the 5' to 3' exonuclease activity.

According to a preferred embodiment, the fluorescent reporter molecule is positioned on the 5'-second hybridization portion not to be digested by the enzyme having the 5' to 3' exonuclease activity.

According to a preferred embodiment, the fluorescent reporter molecule is positioned on the 3'-first hybridization portion not to be digested by the enzyme having the 5' to 3' exonuclease activity.

According to a preferred embodiment, the fluorescent reporter molecule positioned at a site not to be digested by the enzyme having the 5' to 3' exonuclease activity is remained onto the surface of the solid substrate after the step (b), which enables to conveniently detect the fluorescence signal from the reporter molecule in a real-time manner without washing steps.

Preferably, the quencher molecule is positioned at the 5'-end of the TD probe or 1-3 nucleotides apart from the 5'-end and the fluorescent reporter molecule is positioned on the adjacent 3'-end of the TD probe or on the middle of the 3'-first hybridization portion of TD probe.

According to a preferred embodiment, the quencher molecule is positioned on any site of a sequence comprising 1-10 nucleotides from 5'-end, still more preferably, any site of a sequence comprising 1-5 nucleotides from 5'-end, still much more preferably, any site of a sequence comprising 1-3 nucleotides from 5'-end of TD probe. Most preferably, the quencher molecule is positioned on at 5'-end of TD probe.

According to a preferred embodiment, the reporter molecule is positioned on any site of a sequence comprising 1-30 nucleotides from 3'-end, still more preferably, any site of a sequence comprising 1-20 nucleotides from 3'-end, still much more preferably, any site of a sequence comprising 1-15 nucleotides from 3'-end of TD probe.

According to a preferred embodiment, the upstream primer and/or the reverse primer has a dual specificity oligonucleotide (DSO) structure represented by the general formula II described above.

According to a preferred embodiment, the present invention further comprises repeating the steps (a)-(b) or (a)-(c) and for the repetition of the steps (a)-(b) or (a)-(c), the present invention further comprise denaturation between repeating cycles.

Where the present invention further comprises repeating the steps (a)-(b) or (a)-(c), it is preferred that the signal detection is performed for each cycle of the repetition (i.e., real-time manner), at the end of the repetition (i.e., end-point manner) or at each of predetermined time intervals during the repetition. Preferably, the signal detection may be performed for each cycle of the repetition to improve the detection accuracy and further to quantify target nucleic acid.

According to a preferred embodiment, the target nucleic acid sequence used is a pre-amplified nucleic acid sequence by an amplification primer.

According to a preferred embodiment, the amplification primer (e.g., including a forward primer and a reverse primer) for production of pre-amplified target nucleic acid sequences has a dual specificity oligonucleotide (DSO) structure represented by the general formula II described above.

According to a preferred embodiment, the steps (a) and (b) is carried out simultaneously with amplification of the target nucleic acid sequence for detecting target nucleic acid sequence in a real-time manner.

According to a preferred embodiment, the TD probe has a blocker site containing as a blocker at least one nucleotide resistant to cleavage by an enzyme having a 5' to 3' exonuclease activity. According to a preferred embodiment, the blocker site is positioned at a site of the TD probe cleaved by the enzyme having the 5' to 3' exonuclease activity and preferably at 3'-hybridization portion of the TD probe.

According to other preferred embodiment, the TD probe has a blocker site containing as a blocker at least one nucleotide resistant to a 5' to 3' exonuclease activity of an enzyme (e.g., the template-dependent nucleic acid polymerase having 5' to 3' exonuclease activity) and the blocker site is positioned at a site cleaved by the endonuclease activity of the enzyme when the TD probe is hybridized with the non-target nucleic acid sequence.

According to a preferred embodiment, the blocker site of the TD probe is positioned on the 3'-first hybridization portion of the TD probe. More preferably, the blocker site of the TD probe is positioned on the 3'-first hybridization portion adjacent to the 3'-end of the separation portion.

According to a preferred embodiment, the target nucleic acid sequence comprises at least two types (more preferably, at least three types, still more preferably at least five types) of nucleic acid sequences and the TD probe comprises at least two types (more preferably, at least three types, still more preferably at least five types) of probes.

According to a preferred embodiment, the target nucleic acid sequence comprises at least two types (more preferably, at least three types, still more preferably at least five types) of nucleic acid sequences, the TD probe comprises at least two types (more preferably, at least three types, still more preferably at least five types) of probes and the upstream primer comprises at least two types (more preferably, at least three types, still more preferably at least five types) of primers.

According to a preferred embodiment, the target nucleic acid sequence comprises at least two types (more preferably, at least three types, still more preferably at least five types) of nucleic acid sequences, the TD probe comprises at least two types (more preferably, at least three types, still more preferably at least five types) of probes and the reverse primer comprises at least two types (more preferably, at least three types, still more preferably at least five types) of primers.

Furthermore, the present invention is very useful in detection of a nucleotide variation.

According to a preferred embodiment, the nucleotide variation on the target nucleic acid sequence is present at a site opposite to the 5'-second hybridization portion of a TD probe.

II. Preferable Embodiment: Real-Time PCR Assay Using TD Probe

Preferably, the present invention is carried out simultaneously with amplification of the target nucleic acid sequence using a primer pair composed of two primers as a forward primer and a reverse primer capable of amplifying the target nucleic acid sequence. Preferably, the amplification is performed in accordance with PCR (polymerase chain reaction) which is disclosed in U.S. Pat. Nos. 4,683,195, 4,683,202, and 4,800,159.

In still another aspect of this invention, there is provided a method for detecting a target nucleic acid sequence from a DNA or a mixture of nucleic acids using a target discriminative probe (TD probe) and a polymerase chain reaction (PCR), which comprises the steps of:

(a) preparing a PCR mixture containing (i) the target nucleic acid sequence, (ii) the TD probe having a hybridizing nucleotide sequence complementary to the target nucleic acid sequence, (iii) a primer pair composed of two primers as a forward primer and a reverse primer each having a hybridizing nucleotide sequence complementary to the target nucleic acid sequence, and (iv) a template-dependent nucleic acid polymerase having a 5' to 3' exonuclease activity; wherein the TD probe is hybridized with a site between the two primers; wherein the TD probe has a modified dual specificity oligonucleotide (mDSO) structure represented by the following general formula I:

$$5'\text{-}X'_p\text{—}Y'_q\text{—}Z'_r\text{-}3' \qquad (I)$$

wherein, $X'_p$ represents a 5'-second hybridization portion having a hybridizing nucleotide sequence complementary to the target nucleic acid sequence; $Y'_q$ represents a separation portion comprising at least three universal bases, $Z'_r$ represents a 3'-first hybridization portion having a hybridizing nucleotide sequence complementary to the target nucleic acid sequence; the TD probe is dually labeled with a fluorescent reporter molecule and a quencher molecule capable of quenching the fluorescence of the reporter molecule; the fluorescent reporter molecule and the quencher molecule all are positioned on the 5'-second hybridization portion, or the reporter molecule and the quencher molecule each is positioned on each different portion of the 5'-second hybridization portion and the separation portion; p, q and r represent the number of nucleotides; and X, Y' and Z' are deoxyribonucleotides or ribonucleotides; the $T_m$ of the 5'-second hybridization portion is lower than that of the 3'-first hybridization portion and the separation portion has the lowest $T_m$ in the three portions of $X'_p$, $Y'_q$ and $Z'_r$; the separation portion separates the 5'-second hybridization portion from the 3'-first hybridization portion in terms of hybridization events to the target nucleic acid sequence, whereby the hybridization specificity of the TD probe are determined dually by the 5'-second hybridization portion and the 3'-first hybridization portion such that the overall hybridization specificity of the TD probe is enhanced;

wherein when the TD probe is hybridized with the target nucleic acid sequence, both of the 5'-second hybridization portion and the 3'-first hybridization portion are hybridized with the target nucleic acid sequence and the 5'-second hybridization portion is digested by the 5' to 3' exonuclease activity of the template-dependent nucleic acid polymerase; wherein when the TD probe is hybridized with the non-target nucleic acid sequence, both the 5'-second hybridization portion and the separation portion form a single strand such that the 5'-second hybridization portion is not digested by the 5' to 3' exonuclease activity of the template-dependent nucleic acid polymerase, whereby the TD probe allows discriminating the target nucleic acid sequence from the non-target nucleic acid sequence;

(b) amplifying the target nucleic acid sequence using the PCR mixture by performing at least two cycles of primer annealing, primer extending and denaturing, wherein the two primers are extended by a polymerase activity of the template-dependent nucleic acid polymerase to amplify the target nucleic acid sequence; wherein when the TD probe is hybridized with the target nucleic acid sequence, the 5'-second hybridization portion is digested by the 5' to 3' exonuclease activity of the template-dependent nucleic acid polymerase to separate the fluorescent reporter molecule from the quencher molecule on the TD probe, resulting in generation of a fluorescence signal; wherein when the TD probe is hybridized with the non-target nucleic acid sequence, the 5'-second hybridization portion is not digested by the 5' to 3' exonuclease activity of the template-dependent nucleic acid polymerase such that the fluorescent reporter molecule is not separated from the quencher molecule on the TD probe, resulting in no fluorescence signal; and (c) detecting the fluorescence signal, such that the fluorescence signal generated is indicative of the presence of the target nucleic acid sequence.

Since the real-time PCR assay of the present invention uses the TD probe and follows the steps of the present method described above, the common descriptions between them are omitted in order to avoid undue redundancy leading to the complexity of this Specification.

In a real-time PCR assay using 5' to 3' nucleolytic reactions, template-dependent nucleic acid polymerases having a 5' to 3' exonuclease activity is employed for target amplification as well as signal generation (e.g. TaqMan probe method). As described hereinabove, the template-dependent nucleic acid polymerase may have two nucleolytic activities including 5' to 3' exonuclease activity and endonuclease activity. The endonuclease activity may cause generation of false positive signals in processes accompanied with target amplification.

To completely overcome problems and troublesome associated with the endonuclease activity, the present invention adopts an unique strategy in which all dual labels are positioned on the 5'-second hybridization portion of the TD probe.

According to a preferred embodiment, the fluorescent reporter molecule and the quencher molecule all are positioned on the 5'-second hybridization portion of TD probe or the fluorescent reporter molecule and the quencher molecule each is positioned on each different portion of the 5'-second hybridization portion and the separation portion of TD probe in the real-time PCR reaction.

Even though the endonuclease activity of the template-dependent nucleic acid polymerase may act at the bifurcation site formed on the 3'-first hybridization portion when the TD probe is hybridized with non-target nucleic acid sequences during real-time PCR, the fluorescent reporter molecule and the quencher molecule positioned on the 5'-second hybridization portion are not separated from each other, such that a fluorescent signal from the fluorescent reporter molecule is not generated by the endonuclease activity.

In this regard, the real-time PCR assay of the present invention completely ensures to eliminate any possibilities of false signal generation.

According to a preferred embodiment, the signal detection is performed for each cycle of the repetition (i.e., real-time manner), at the end of the repetition (i.e., end-point manner) or at each of predetermined time intervals during the repetition. Preferably, the signal detection may be performed for each cycle of the repetition to improve the detection accuracy.

According to a preferred embodiment, the target nucleic acid sequence comprises at least two types (more preferably, at least three types, still more preferably at least five types) of nucleic acid sequences, the TD probe comprises at least two types (more preferably, at least three types, still more preferably at least five types) of probes, the forward primer comprises at least two types (more preferably, at least three types, still more preferably at least five types) of primers and the reverse primer comprises at least two types (more preferably, at least three types, still more preferably at least five types) of primers.

According to a preferred embodiment, the target nucleic acid sequence comprises a nucleotide variation.

According to a preferred embodiment, the nucleotide variation on the target nucleic acid sequence is present at a site opposite to the 5'-second hybridization portion of a TD probe.

According to a preferred embodiment, the forward primer and/or the reverse primer has a dual specificity oligonucleotide (DSO) structure represented by the general formula II described above.

III. Target Detection Process by Ligation Reaction in a Liquid Phase or on a Solid Phase In further aspect of this invention, there is provided a method for detecting a target nucleic acid sequence from a DNA or a mixture of nucleic acids using a target discriminative probe (TD probe), which comprises the steps of:

(a) hybridizing the target nucleic acid sequence with a first probe having a hybridizing nucleotide sequence complementary to a first site of the target nucleic acid sequence and a second probe having a hybridizing nucleotide sequence complementary to a second site of the target nucleic acid sequence which is positioned upstream of the first site; wherein at least one of the first probe and the second probe has a label to generate a detectable signal; wherein the second probe is a TD probe; wherein the TD probe has a modified dual specificity oligonucleotide (mDSO) structure represented by the following general formula I:

$$5'\text{-}X'_p\text{—}Y'_q\text{—}Z'_r\text{-}3' \qquad (I)$$

wherein, $X'_p$ represents a 5'-second hybridization portion having a hybridizing nucleotide sequence complementary to the target nucleic acid sequence; $Y'_q$ represents a separation portion comprising at least three universal bases, $Z'_r$ represents a 3'-first hybridization portion having a hybridizing nucleotide sequence complementary to the target nucleic acid sequence; p, q and r represent the number of nucleotides; and X, Y' and Z' are deoxyribonucleotides or ribonucleotides; the $T_m$ of the 5'-second hybridization portion is lower than that of the 3'-first hybridization portion and the separation portion has the lowest $T_m$ in the three portions of $X'_p$, $Y'_q$ and $Z'_r$; the separation portion separates the 5'-second hybridization portion from the 3'-first hybridization portion in terms of hybridization events to the target nucleic acid sequence, whereby the hybridization specificity of the TD probe are determined dually by the 5'-second hybridization portion and the 3'-first hybridization portion such that the overall hybridization specificity of the TD probe is enhanced; wherein when the second probe is hybridized with the target nucleic acid sequence, both of the 5'-second hybridization portion and the 3'-first hybridization portion of the second probe are hybridized with the target nucleic acid sequence to allow ligation of the first probe and the second probe; wherein when the second probe is hybridized with the non-target nucleic acid sequence, both of the 5'-second hybridization portion and the separation portion of the second probe form a single strand such that the first probe and the second probe are not ligated, whereby the second probe allows discriminating the target nucleic acid sequence from the non-target nucleic acid sequence;

(b) ligating the first probe and the second probe hybridized with the target nucleic acid sequence such that a ligated probe is produced;

(c) denaturing the resultant of step (b);

(d) detecting the signal from the label on the ligated probe such that the signal is indicative of the presence of the target nucleic acid sequence.

Since the present method using ligation reactions employs the TD probe, the common descriptions are omitted in order to avoid undue redundancy leading to the complexity of this Specification.

The present method may be performed in a liquid phase or on a solid phase. Preferably, the present method is carried out on a solid phase.

In the present method using ligation reactions, the first probe and the second probe are first hybridized with the target nucleic acid sequence. The second probe is the TD probe described above. The first probe has a hybridizing nucleotide sequence complementary to the first site of the target nucleic acid sequence and the second probe has a hybridizing nucleotide sequence complementary to a second site of the target nucleic acid sequence which is positioned upstream of the first site. The first probe and the second probe must be hybridized with the target nucleic acid sequence in the order described above. Unless the hybridization positions of the first probe and the second probe are complied with the above, the target-specific detection by the present invention is not accomplished.

According to a preferred embodiment, the first probe and the second probe are positioned at immediately adjacent locations to each other when hybridized with the target nucleic acid sequence.

The adjacent positioning is necessary for ligation reactions between the two probes. The term used herein "adjacent" in conjunction with hybridization positions of the first probe and the second probe means that the 3'-end of one probe and the 5'-end of the other probe are sufficiently near each other to allow connection of the ends of both probes to one another.

According to a preferred embodiment, the 3'-end of the first probe has a hydroxyl group and the 5'-end of the second probe has a phosphate group.

The term used herein "immediately adjacent" in conjunction with hybridization positions of the first probe and the second probe means that refers to a sufficient proximity between two probes to allow the 5'-end of second probe that is brought into juxtaposition with the 3'-end of the first probe so that they may be ligated by a suitable agent such as ligase. Where the 5'-end of the second probe is 0 nucleotide apart from the 3'-end of the first probe, both probes generate a nick to be ligated by ligase.

Either the first probe or the second probe has a label to generate a detectable signal. Alternatively, both the first probe and the second probe have a label.

According to a preferred embodiment, the label is a chemical label, an enzymatic label, a radioactive label, a fluorescent label, an interactive label, a luminescent label, a chemiluminescent label or a metal label.

More preferably, the label is the interactive label system comprising a pair of a reporter molecule and a quencher molecule. For example, the first probe is labeled with either the reporter molecule or the quencher molecule and the second probe is labeled with either the quencher molecule or the reporter molecule.

According to a preferred embodiment, the first probe has a dual specific oligonucleotide (DSO) structure represented by the general formula II described above.

More preferably, the first probe has the DSO structure and the second probe is TD probe and the 3'-end of the first probe is positioned at immediately adjacent to the 5'-end of the second probe.

Figure 6A:
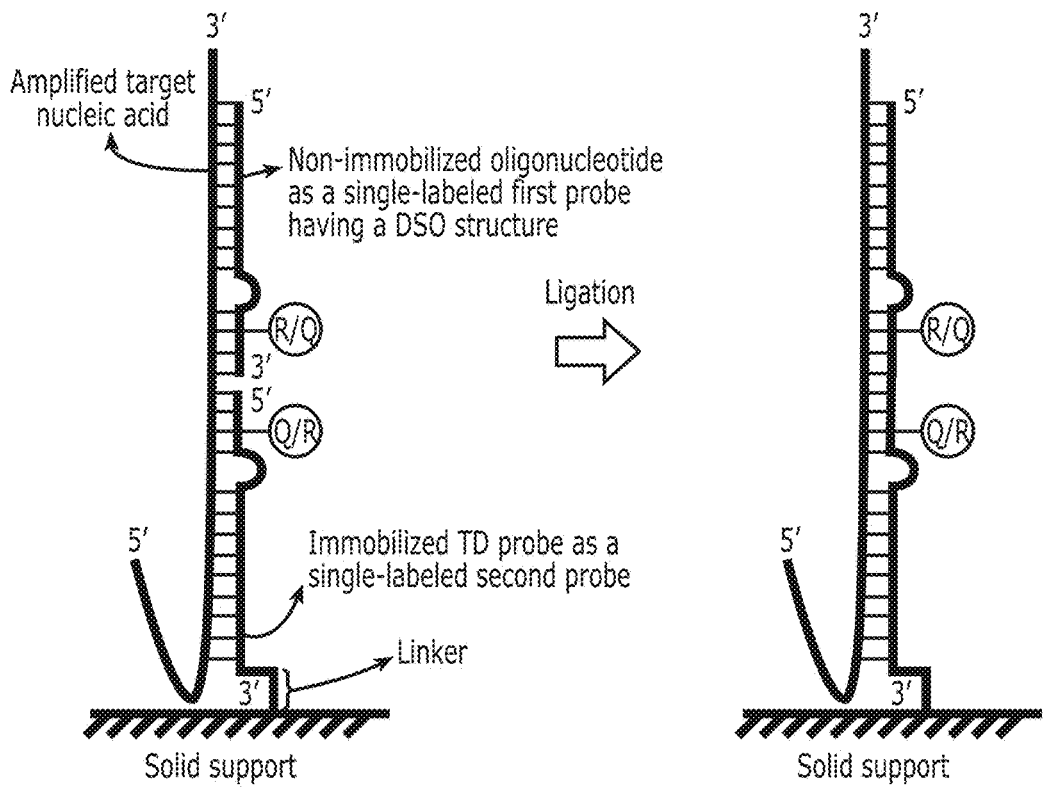
FIGS. 6A and 6B schematically represent the discrimination of a target nucleic acid sequence from a non-target nucleic acid sequence using a non-immobilized oligonucleotide as a single-labeled first probe, an immobilized TD probe as a single-labeled second probe, and a ligase in solid phase.
Figure 6B:
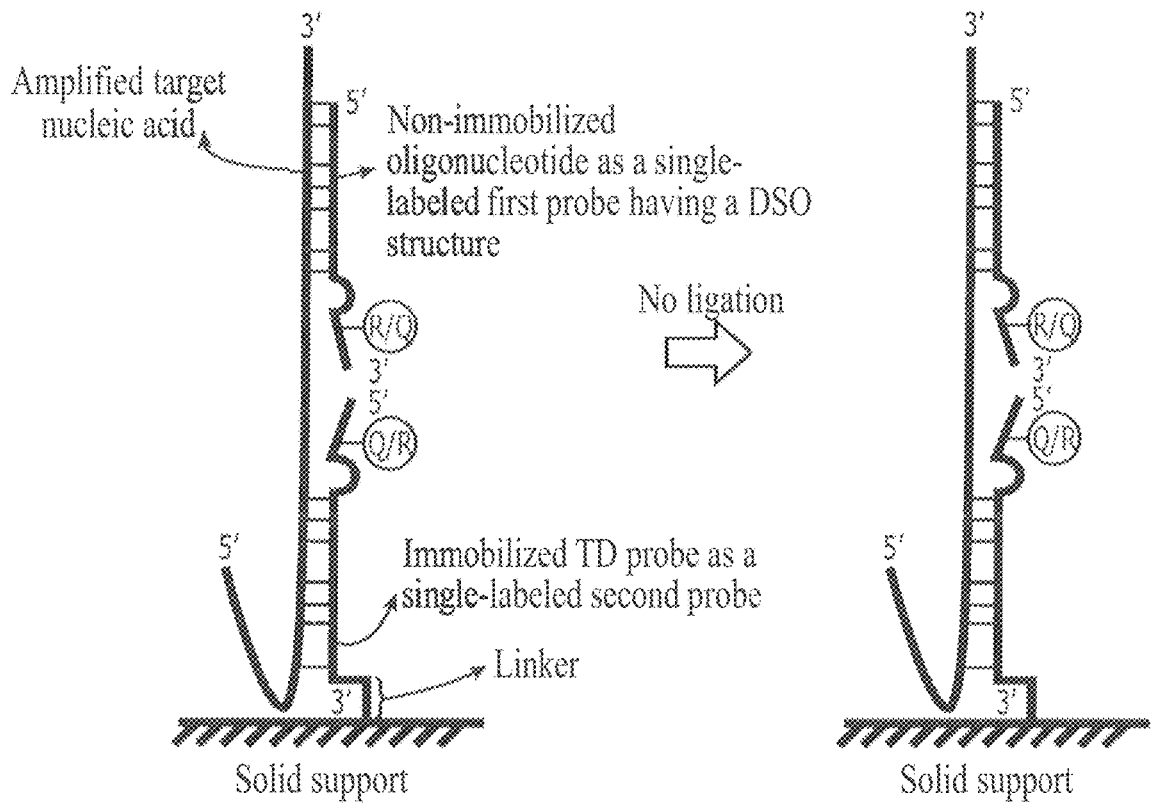

The accuracy in the detection of target sequences using probes generally depends on specificity of probes to target sequences. Where the first probe having the DSO structure and the second probe having the mDSO structure (TD probe) are used, the 3'-second hybridization portion of the first probe and the 5'-second hybridization portion of the second probe are positioned at immediately adjacent to each other when the two probes are hybridized with the target nucleic acid sequence. Then, the 3'-second hybridization portion of the first probe and the 5'-second hybridization portion of the second probe are ligated. When the first probe and the second probe are hybridized with the non-target sequence, only their first hybridization portions are involved in the non-specific hybridization but their second hybridization portions each forms a single strand, resulting in no ligation of the first probe and the second probe (FIG. 6).

As described above, it could be understood that the probe pair of the first probe having the DSO structure and the second probe having the mDSO structure are completely free from false positive results in target detection.

Following the hybridization, the first probe and the second probe hybridized with the target nucleic acid sequence are ligated.

Since enzymatic ligation is the preferred method of covalently attaching the first probe and the second probe, the term "ligation" will be used throughout the application. However, the term "ligation" is a general term and is to be understood to include any method of covalently attaching both probes. One alternative to enzymatic ligation is photoligation as described in EP 0324616.

The ligation in the present invention may be carried out according to both alternative methods: First, the ligation may be performed by a gap filling ligation method (U.S. Pat. No. 6,004,826). The 3'-end of one probe extended by DNA polymerases is ligated to the 5'-end of the other probe. Second, the ligation may be performed by a nick sealing method without extension reactions.

According to a preferred embodiment, the ligation in the present invention is performed by nick sealing without any further extension reactions to connect the 3'-end of one probe to the 5'-end of the other probe.

The ligation reactions may be carried out using a wide variety of ligation agents, including enzymatic ligation agents and non-enzymatic ligation agents such as chemical and photoligation agents. Chemical ligation agents include, without limitation, activating, condensing, and reducing agents, such as carbodiimide, cyanogen bromide (BrCN), N-cyanoimidazole, imidazole, 1-methylimidazole/carbodiimide/cystamine, dithiothreitol (DTT) and ultraviolet light. Autoligation, i.e., spontaneous ligation in the absence of a ligating agent, is also within the scope of the teachings herein. Detailed protocols for chemical ligation methods and descriptions of appropriate reactive groups can be found in Xu et al., Nucl. Acids Res., 27:875-81(1999); Gryaznov and Letsinger, Nucl. Acids Res. 21:1403-08(1993); Gryaznov et al., Nucleic Acid Res. 22:2366-69(1994); Kanaya and Yanagawa, Biochemistry 25:7423-30(1986); Luebke and Dervan, Nucl. Acids Res. 20:3005-09(1992); Sievers and von Kiedrowski, Nature 369:221-24(1994); Liu and Taylor, Nucl. Acids Res. 26:3300-04(1999); Wang and Kool, Nucl. Acids Res. 22:2326-33(1994)).

Photoligation using light of an appropriate wavelength as a ligation agent is also within the scope of the teachings. In certain embodiments, photoligation comprises probes comprising nucleotide analogs, including but not limited to, 4-thiothymidine (s4T), 5-vinyluracil and its derivatives, or combinations thereof. In certain embodiments, the ligation agent comprises: (a) light in the UV-A range (about 320 nm to about 400 nm), the UV-B range (about 290 nm to about 320 nm), or combinations thereof, (b) light with a wavelength between about 300 nm and about 375 nm, (c) light with a wavelength of about 360 nm to about 370 nm; (d) light with a wavelength of about 364 nm to about 368 nm, or (e) light with a wavelength of about 366 nm. Descriptions of photoligation can be found in, among other places, Fujimoto et al., Nucl. Acid Symp. Ser. 42:39-40(1999); Fujimoto et al., Nucl. Acid Res. Suppl. 1:185-86(2001); Fujimoto et al., Nucl. Acid Suppl., 2:155-56(2002); Liu and Taylor, Nucl. Acid Res. 26:3300-04(1998).

According to a preferred embodiment, the ligation reaction is performed using a ligase such as bacteriophage T4 ligase, E. coli ligase and thermostable ligase. More preferably, the ligation reaction is carried out using thermostable ligase including Afu ligase, Taq ligase, Tfl ligase, Mth ligase, Tth ligase, Tth HB8 ligase, Thermus species AK16D ligase, Ape ligase, LigTk ligase, Aae ligase, Rm ligase and Pfu ligase (Housby et al., Nucl. Acids Res. 28:e10(2000); Tong et al., Nucl. Acids Res. 28:1447-54(2000); Nakatani et al., Eur, J. Biochem. 269:650-56(2002); Zirvi et al., Nucl. Acids Res. 27:e40(1999); Sriskanda et al., Nucl. Acids Res. 11:2221-28(2000)).

The internucleotide linkage generated by the ligation includes phosphodiester bond and other linkages. For instance, the ligation using ligases generally produces phosphodiester bonds. Non-enzymatic methods for ligation may form other internucleotide linkages. Other internucleotide linkages include, without limitation, covalent bond formation between appropriate reactive groups such as between an α-haloacyl group and a phosphothioate group to form a thiophosphorylacetylamino group, a phosphorothioate and tosylate or iodide group to form a 5'-phosphorothioester, and pyrophosphate linkages.

After the ligation reaction, its resultant is then denatured to separate from the target nucleic acid sequence.

In the present method performed on the solid phase, the first probe or the second probe as an immobilized probe is immobilized on the surface of the solid substrate. The other probe as a mobilized probe is not immobilized.

Figure 7:
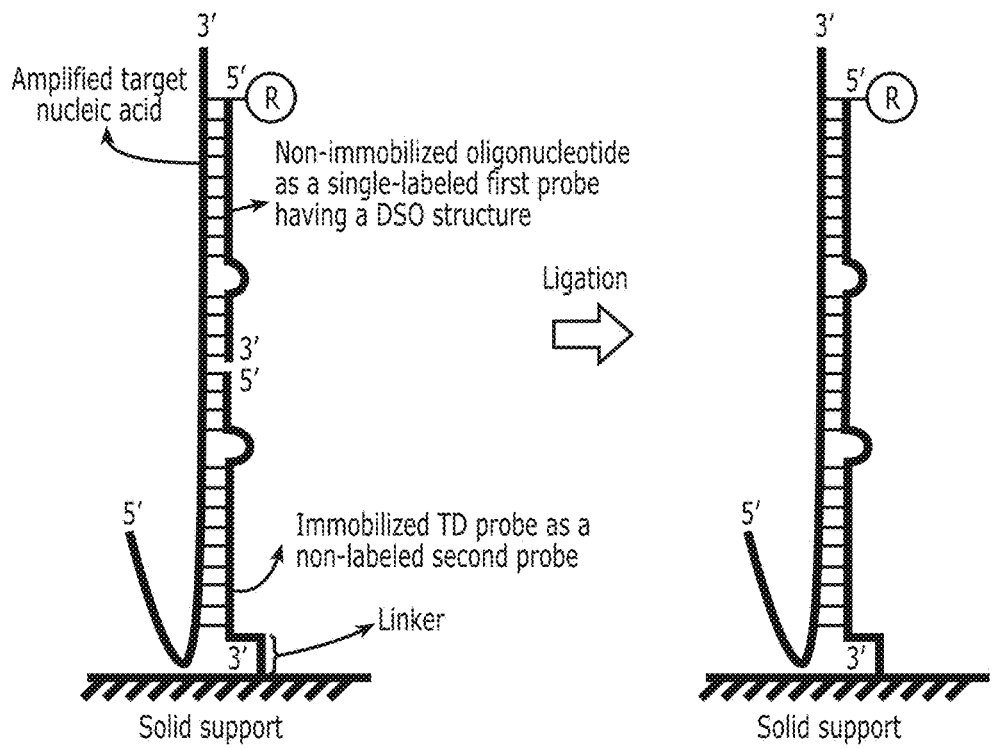
FIG. 7 schematically represents the ligation on target-specific hybridization using a non-immobilized oligonucleotide as a single-labeled first probe, an immobilized TD probe as a non-labeled second probe, and a ligase in solid phase.

More preferably, in the method performed on the solid phase, the first probe is immobilized through its 5'-end on the surface of a solid substrate and the second probe is not immobilized. Alternatively, in the method performed on the solid phase, the second probe is immobilized through its 3'-end on the surface of the solid substrate and the first probe is not immobilized (FIG. 6).

Where a single label molecule is used on the solid phase, it is preferably positioned on the mobilized probe (FIG. 7).

When the two probes are hybridized with the non-target nucleic acid sequence, they are not ligated to each other and the mobilized probe is separated from the immobilized probe during the denaturation such that no signal is generated.

As such, the denaturation step is one of checkpoints to specifically detect the target nucleic acid sequence in the present invention.

Finally, the signal from the label on a ligation of the first probe and the second probe is detected to identify the presence of the target nucleic acid sequence.

According to a preferred embodiment, the preset solid-phase method further comprises, prior to the step (d), washing the resultant of step (c) for removal of the mobilized probe not ligated with the immobilized probe.

According to a preferred embodiment, the method further comprises repeating the steps (a)-(c) or (a)-(d).

According to a preferred embodiment, the target nucleic acid sequence used in step (a) is a pre-amplified nucleic acid sequence by using an amplification primer. Preferably, the amplification primer has the dual hybridization oligonucleotide (DSO) structure represented by the general formula II.

The pre-amplified target nucleic acid sequence may include a target nucleic acid sequence pre-amplified in other reaction environment (or reaction vessel) than a reaction environment (or reaction vessel) for the steps (a)-(c). Alternatively, the pre-amplified target nucleic acid sequence may be obtained in the same reaction environment (or reaction vessel) as a reaction environment (or reaction vessel) for the steps (a)-(c).

According to a preferred embodiment, the target nucleic acid sequence comprises at least two types (more preferably, at least three types, still more preferably at least five types) of nucleic acid sequences, the first probe comprises at least two types (more preferably, at least three types, still more preferably at least five types) of probes and the second probe comprises at least two types (more preferably, at least three types, still more preferably at least five types) of probes.

According to a preferred embodiment, the target nucleic acid sequence comprises a nucleotide variation, more preferably a SNP (single nucleotide polymorphism).

According to a preferred embodiment, the nucleotide variation on the target nucleic acid sequence is present at a site opposite to the 5'-second hybridization portion of the second probe.

IV. Target Detection Process by Fluorescent Signal Change Depending on the Hybridization in a Liquid Phase or on a Solid Phase In still further aspect of this invention, there is provided a method for detecting a target nucleic acid sequence from a DNA or a mixture of nucleic acids using a target discriminative probe (TD probe), which comprises the steps of:

(a) hybridizing the target nucleic acid sequence with the TD probe having a hybridizing nucleotide sequence complementary to the target nucleic acid sequence; wherein the TD probe has a modified dual specificity oligonucleotide (mDSO) structure represented by the following general formula I:

$$5'\text{-}X'_p\text{—}Y'_q\text{-}T_r\text{-}3' \qquad (I)$$

wherein, $X'_p$ represents a 5'-second hybridization portion having a hybridizing nucleotide sequence complementary to the target nucleic acid sequence; $Y'_q$ represents a separation portion comprising at least three universal bases, $Z'_r$ represents a 3'-first hybridization portion having a hybridizing nucleotide sequence complementary to the target nucleic acid sequence; the TD probe is labeled with a fluorescent reporter molecule on the 5'-second hybridization portion; p, q and r represent the number of nucleotides; and X', Y' and Z' are deoxyribonucleotides or ribonucleotides; the $T_m$ of the 5'-second hybridization portion is lower than that of the 3'-first hybridization portion and the separation portion has the lowest $T_m$ in the three portions of $X'_p$, $Y'_q$ and $Z'_r$; the separation portion separates the 5'-second hybridization portion from the 3'-first hybridization portion in terms of hybridization events to the target nucleic acid sequence, whereby the hybridization specificity of the TD probe is determined dually by the 5'-second hybridization portion and the 3'-first hybridization portion such that the overall hybridization specificity of the TD probe is enhanced; wherein when the TD probe is hybridized with the target nucleic acid sequence, both of the 5'-second hybridization portion and the 3'-first hybridization portion are hybridized with the target nucleic acid sequence to induce a change in fluorescence from the fluorescent reporter molecule; wherein when the TD probe is hybridized with the non-target nucleic acid sequence, both the 5'-second hybridization portion and the separation portion form a single strand to induce no change in fluorescence from the fluorescent reporter molecule, whereby the TD probe allows discriminating the target nucleic acid sequence from the non-target nucleic acid sequence; and (b) detecting the fluorescence change such that the fluorescence change is indicative of the presence of the target nucleic acid sequence.

Since the present invention utilizes the different hybridization patterns of 5'-second hybridization portion of the TD probe, the common descriptions are omitted in order to avoid undue redundancy leading to the complexity of this Specification.

It was disclosed that a single fluorophore-labeled oligonucleotide generates different fluorescence emission in single-stranded and double-stranded states (see U.S. Pat. Nos. 7,348,141 and 7,537,886).

We have found that when the TD probe is labeled with a single fluorescent reporter molecule on its 5'-second hybridization portion, a different fluorescence intensity was generated depending on hybridization with target or non-target nucleic acid sequences.

The change in fluorescence from the fluorescent reporter to be finally detected includes decrease in fluorescence as well as increase in fluorescence. The types of fluorescence in which the change may be detected include, but not limited to, fluorescent intensity, fluorescent polarization, fluorescence lifetime and quantum yield of fluorescence. Most preferably, the fluorescence to be detected is fluorescent intensity from the fluorescent reporter molecule.

The change in fluorescence from the fluorescent reporter upon hybridization with target sequences is dependent on several factors such as types and positions of labels, as found in U.S. Pat. Nos. 7,348,141 and 7,537,886.

The fluorescent reporter molecule used in the present invention may be described with referring to descriptions indicated hereinabove. According to a preferred embodiment, the fluorescent reporter molecule is a fluorescein based molecule (ex, JOE, TET or FAM), rhodamine based molecule (ex, TAMRA or ROX) or BODIPY530/550.

The fluorescent reporter molecule is positioned on the 5'-second hybridization portion which possesses the greatest discrimination potential in the TD probe for target and non-target sequences. As demonstrated throughout the application, the hybridization behavior of the 5'-second hybridization portion is the most determinant factor in discriminating target sequences from non-target sequences.

The fluorescent reporter molecule is positioned on 5'-end, 3' end or internal nucleotide of the 5'-second hybridization portion. More preferably, the fluorescent reporter molecule is positioned on internal nucleotide.

According to a preferred embodiment, the fluorescent reporter molecule is linked to uracil residue.

According to a preferred embodiment, the fluorescent change is observed at a predetermined temperature, or over a range of temperatures.

According to a preferred embodiment, the step (a) is carried out using the TD probe together with a reverse primer and a template-dependent nucleic acid polymerase such that the target nucleic acid sequence hybridizable with the TD probe is additionally generated to enhance the fluorescence change indicative of the presence of the target nucleic acid sequence.

According to a preferred embodiment, the step (a) is carried out using the TD probe together with a primer pair composed of two primers as a forward primer and a reverse primer and a template-dependent nucleic acid polymerase such that the target nucleic acid sequence hybridizable with the TD probe is amplified by PCR to enhance the fluorescence change indicative of the presence of the target nucleic acid sequence.

Alternatively, the TD probe is additionally labeled with a quencher molecule capable of quenching the fluorescence of the reporter molecule and the quencher is positioned on the TD probe to quench the fluorescence of the reporter molecule when the TD probe or the 5'-second hybridization portion of the TD probe is not involved in hybridization with the target nucleic acid sequence.

According to a preferred embodiment, the quencher is positioned on the TD probe to quench the fluorescence of the reporter molecule conformationally when the TD probe or the 5'-second hybridization portion of the TD probe is not involved in hybridization with the target nucleic acid sequence.

According to a preferred embodiment, the quencher molecule is fluorescent and the signal indicative of the presence of the target nucleic acid sequence to be detected is a signal from the fluorescent quencher molecule.

Where the present invention is performed together with the reverse primer or the primer pair, the template-dependent nucleic acid polymerase is preferably a thermostable polymerase with no 5' to 3' exonuclease activity including Stoffel fragment of Taq polymerase (F C Lawyer et al., *Genome Res.* 2:275-287(1993)) and mutant forms of DNA polymerase of *Thermus aquaticus, Thermus flavus* or *Thermus thermophilus* (U.S. Pat. No. 5,885,813). Examples of those are: KOD (exo-) DNA polymerase (TOYOBO), Vent (exo-) DNA polymerase (NEB), Deep vent (exo-) DNA polymerase (NEB), Platinum™ Tfi Exo(–) DNA Polymerase (Invitrogen), Amplitaq DNA polymerase stoffel fragment (ABI), Exo-Pfu DNA Polymerase (Agilent).

The present method may be also carried out using thermostable polymerases with 5' to 3' exonuclease activities.

According to a preferred embodiment, the present method is performed in a liquid phase or on a solid phase. When the present method is performed on the solid phase, the TD probe is immobilized through its 3'-end on the surface of a solid substrate.

V. Designing and Preparation of Probe Capable of Discriminating Target Sequences In another aspect of this invention, there is provided a method for enabling a probe molecule to discriminate a target nucleic acid sequence from a non-target nucleic acid sequence, which comprises the steps of:

(a) selecting a target nucleic acid sequence;
(b) designing a sequence of a probe molecule having (i) a hybridizing sequence complementary to the target nucleic acid and (ii) a separation portion comprising at least three universal bases, such that the separation portion intervenes in the hybridizing sequence to form three portions in the probe molecule; and
(c) determining the position of the separation portion in the probe molecule to allow a portion at the 5'-direction of the separation portion to have a lower $T_m$ than a portion at the 3'-direction of the separation portion and to allow the separation portion to have the lowest $T_m$ in the three portions, thereby providing the probe molecule having three distinct portions with different $T_m$ values from one another in which (i) a 5'-second hybridization portion of the probe molecule has a hybridizing nucleotide sequence complementary to the target nucleic acid, (ii) a 3'-first hybridization portion of the probe molecule has a hybridizing nucleotide sequence complementary to the target nucleic acid; and (iii) the separation portion of the probe molecule between the 5'-second hybridization portion and the 3'-first hybridization portion comprises at least three universal bases; and the $T_m$ of the 5'-second hybridization portion is lower than that of the 3'-first hybridization portion and the separation portion has the lowest $T_m$ in the three portions, wherein when the probe molecule is hybridized with the target nucleic acid sequence, both of the 5'-second hybridization portion and the 3'-first hybridization portion are hybridized with the target nucleic acid sequence; wherein when the probe molecule is hybridized with the non-target nucleic acid sequence, both of the 5'-second hybridization portion and the separation portion form a single strand, whereby the probe molecule allows discriminating the target nucleic acid sequence from the non-target nucleic acid sequence.

The present method is directed to provide a novel approach to dramatically increase discrimination power of probes for target sequences. The present method may be also expressed as a method for improving a discrimination ability of a probe for target sequences.

The present method is performed to prepare the TD probe discussed hereinabove. Therefore, in the interest of avoiding unnecessary redundancy, the common descriptions between them are not being repeated but they are incorporated into this description of the method as if they were repeated.

The present method provides a novel strategy for increasing discrimination ability by introducing novel characteristics into oligonucleotide sequences per se, which provides novel probes to show different hybridization behaviors with target and non-target sequences.

It is critical in the present method to design a sequence of a probe molecule having (i) a hybridizing sequence complementary to the target nucleic acid and (ii) a separation portion comprising at least three universal bases, such that the separation portion intervenes in the hybridizing sequence to form three portions in the probe molecule.

In this step, the structural outline of the oligonucleotide is presented to show a 5'-end portion/separation portion/3'-end portion in the oligonucleotide. Both the 5'-end and 3'-end portions carry a hybridizing sequence complementary to the target nucleic acid and are intervened by the separation portion.

The most critical step in the present invention is to determine the position of the separation portion in the probe to allow a portion at the 5'-direction of the separation portion to have a lower $T_m$ than a portion at the 3'-direction of the separation portion and to allow the separation portion to have the lowest $T_m$ in the three portions, thereby providing an oligonucleotide having three distinct portions with different $T_m$ values from one another.

The novel structural characteristics introduced into oligonucleotides by the present method are: (i) three distinct portions (5'-second hybridization portion, separation portion and 3'-first hybridization portion) in oligonucleotide sequences; (ii) different $T_m$ values of the three portions from one another; (iii) separation portion comprising at least three universal bases between the 5'-second hybridization portion and 3'-first hybridization portion; (iv) two portions involved in molecular interaction with targets in hybridization, which is separated in terms of hybridization event by the separation portion; (v) $T_m$ values following the order of the 3'-first hybridization portion, 5'-second hybridization portion and separation portion. Such structural features ensure the hybridization of probes to occur in distinctly different fashions with target and non-target sequences, permitting dramatic increase in hybridization specificity of probes to their target sequences.

IV. Kits for Target Detection

1. Kits for Target Detection in a Liquid Phase

In still further aspect of this invention, there is provided a kit for detecting a target nucleic acid sequence from a DNA or a mixture of nucleic acids, which comprises a target discriminative probe (TD probe) having a modified dual specificity oligonucleotide (mDSO) structure represented by the general formula I described above to allow for discrimination of the target nucleic acid sequence from a non-target nucleic acid sequence.

Since the kit of this invention is constructed to perform the detection methods of the present invention described above, the common descriptions between them are omitted in order to avoid undue redundancy leading to the complexity of this Specification.

According to a preferred embodiment, the TD probe has a label or an interactive label system containing a plurality of labels to generate a detectable signal.

More preferably, the interactive label system is a pair of a reporter molecule and a quencher molecule positioned on the TD probe According to a preferred embodiment, the reporter molecule and the quencher molecule all are positioned on the 5'-second hybridization portion or the reporter molecule and the quencher molecule each is positioned on each different portion of the 5'-second hybridization portion and the separation portion.

According to a preferred embodiment, the TD probe has one of the reporter molecule and the quencher molecule on its 5'-second hybridization portion and the other on its 3'-first hybridization portion.

According to a preferred embodiment, wherein the kit further comprises an enzyme having a 5' to 3' exonuclease activity.

According to a preferred embodiment, kit further comprises a template-dependent nucleic acid polymerase having the 5' to 3' exonuclease activity and at least one of an upstream primer to be hybridized with a site downstream of a hybridized site of the TD probe and a reverse primer.

According to a preferred embodiment, the target nucleic acid sequence used is a pre-amplified nucleic acid sequence by an amplification primer and the kit further comprises the amplification primer.

According to a preferred embodiment, the target nucleic acid sequence comprises at least two types of nucleic acid sequences and the TD probe comprises at least two types of probes.

According to a preferred embodiment, the target nucleic acid sequence comprises at least two types of nucleic acid sequences, the TD probe comprises at least two types of probes and the upstream primer comprises at least two types of primers or the reverse primer comprises at least two types of primers.

According to a preferred embodiment, the target nucleic acid sequence comprises a nucleotide variation.

According to a preferred embodiment, the nucleotide variation on the target nucleic acid sequence is present at a site opposite to the 5'-second hybridization portion of the TD probe.

According to a preferred embodiment, the TD probe has a blocker site containing as a blocker at least one nucleotide resistant to cleavage by an enzyme having a 5' to 3' exonuclease activity and the blocker site is positioned on the 3'-first hybridization portion of the TD probe.

2. Kits for Target Detection on a Solid Phase

In another aspect of this invention, there is provided a kit for detecting a target nucleic acid sequence on a solid phase from a DNA or a mixture of nucleic acids using a target discriminative probe (TD probe), which comprises:

(a) the TD probe having a hybridizing nucleotide sequence complementary to the target nucleic acid sequence; wherein the TD probe is immobilized through its 3'-end on the surface of the solid substrate; wherein the TD probe has a modified dual specificity oligonucleotide (mDSO) structure represented by the following general formula I:

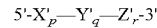

$$5'\text{-}X'_p\text{—}Y'_q\text{—}Z'_r\text{-}3' \tag{I}$$

wherein, $X'_p$ represents a 5'-second hybridization portion having a hybridizing nucleotide sequence complementary to the target nucleic acid sequence; $Y'_q$ represents a separation portion comprising at least three universal bases, $Z'_r$ represents a 3'-first hybridization portion having a hybridizing nucleotide sequence complementary to the target nucleic acid sequence; the TD probe has a label generating a detectable signal and the label is positioned on the 5'-second hybridization portion of the TD probe; p, q and r represent the number of nucleotides; and X, Y' and Z' are deoxyribonucleotides or ribonucleotides; the $T_m$ of the 5'-second hybridization portion is lower than that of the 3'-first hybridization portion and the separation portion has the lowest $T_m$ in the three portions of $X'_p$, $Y'_q$ and $Z'_r$; the separation portion separates the 5'-second hybridization portion from the 3'-first hybridization portion in terms of hybridization events to the target nucleic acid sequence, whereby the hybridization specificity of the TD probe are determined dually by the 5'-second hybridization portion and the 3'-first hybridization portion such that the overall hybridization specificity of the TD probe is enhanced;

wherein when the TD probe is hybridized with the target nucleic acid sequence, both of the 5'-second hybridization portion and the 3'-first hybridization portion are hybridized with the target nucleic acid sequence and the 5'-second hybridization portion is digested by the enzyme having the 5' to 3' exonuclease activity; wherein when the TD probe is hybridized with the non-target nucleic acid sequence, both the 5'-second hybridization portion and the separation portion form a single strand such that the 5'-second hybridization portion is not digested by the enzyme having the 5' to 3' exonuclease activity, whereby the TD probe allows discriminating the target nucleic acid sequence from the non-target nucleic acid sequence; and (b) the solid substrate.

Since the kit of this invention is constructed to perform the detection method of the present invention described above, the common descriptions between them are omitted in order to avoid undue redundancy leading to the complexity of this specification.

According to a preferred embodiment, the label is a chemical label, an enzymatic label, a radioactive label, a fluorescent label, an interactive label, a luminescent label, a chemiluminescent label or a metal label. More preferably, the label is the interactive label system comprising a pair of a fluorescent reporter molecule and a quencher molecule and the TD probe has one of the reporter molecule and the quencher molecule at a site on the 5'-second hybridization portion and the other on a site not to be digested by the enzyme having the 5' to 3' exonuclease activity.

According to a preferred embodiment, the quencher molecule is positioned at a site on the 5'-second hybridization portion of the TD probe and the fluorescent reporter molecule is positioned on a site not to be digested by the enzyme having the 5' to 3' exonuclease activity; wherein when the TD probe is hybridized with the target nucleic acid sequence, its 5'-second hybridization portion is digested by the enzyme having the 5' to 3' exonuclease activity to separate the fluorescent reporter molecule from the quencher molecule on the TD probe, resulting in generation of a fluorescence signal; wherein when the TD probe is hybridized with the non-target nucleic acid sequence, the 5'-second hybridization portion is not digested by the enzyme having the 5' to 3' exonuclease activity, resulting in no fluorescence signal whereby the fluorescent signal on the solid substrate is detected to determine the presence of the target nucleic acid sequence.

According to a preferred embodiment, the kit further comprises an enzyme having a 5' to 3' exonuclease activity.

According to a preferred embodiment, the target nucleic acid sequence comprises at least two types of nucleic acid sequences and the TD probe comprises at least two types of probes.

According to a preferred embodiment, the target nucleic acid sequence comprises a nucleotide variation and the nucleotide variation on the target nucleic acid sequence is present at a site opposite to the 5'-second hybridization portion of the TD probe.

According to a preferred embodiment, the TD probe has a blocker site containing as a blocker at least one nucleotide resistant to cleavage by an enzyme having a 5' to 3' exonuclease activity and the blocker site is positioned on the 3'-first hybridization portion of the TD probe.

3. Kits for Target Detection Using PCR

In still another aspect of this invention, there is provided a kit for detecting a target nucleic acid sequence from a DNA or a mixture of nucleic acids using a target discriminative probe (TD probe) and a polymerase chain reaction (PCR), which comprises:

(a) the TD probe having a hybridizing nucleotide sequence complementary to the target nucleic acid sequence; and (b) a primer pair composed of two primers as an upstream primer and a reverse primer each having a hybridizing nucleotide sequence complementary to the target nucleic acid sequence;

wherein the TD probe is hybridized with a site between the two primers; wherein the TD probe has a modified dual specificity oligonucleotide (mDSO) structure represented by the following general formula I:

$$5'\text{-}X'_p\text{—}Y'_q\text{—}Z'_r\text{-}3' \tag{I}$$

wherein, $X'_p$ represents a 5'-second hybridization portion having a hybridizing nucleotide sequence complementary to the target nucleic acid sequence; $Y'_q$ represents a separation portion comprising at least three universal bases, $Z'_r$ represents a 3'-first hybridization portion having a hybridizing nucleotide sequence complementary to the target nucleic acid sequence; the TD probe is dually labeled with a fluorescent reporter molecule and a quencher molecule capable of quenching the fluorescence of the reporter molecule; the fluorescent reporter molecule and the quencher molecule all are positioned on the 5'-second hybridization portion, or the reporter molecule and the quencher molecule each is positioned on each different portion of the 5'-second hybridization portion and the separation portion; p, q and r represent the number of nucleotides; and X, Y' and Z' are deoxyribonucleotides or ribonucleotides; the $T_m$ of the 5'-second hybridization portion is lower than that of the 3'-first hybridization portion and the separation portion has the lowest $T_m$ in the three portions of $X'_p$, $Y'_q$ and $Z'_r$; the separation portion separates the 5'-second hybridization portion from the 3'-first hybridization portion in terms of hybridization events to the target nucleic acid sequence, whereby the hybridization specificity of the TD probe are determined dually by the 5'-second hybridization portion and the 3'-first hybridization portion such that the overall hybridization specificity of the TD probe is enhanced;

wherein when the TD probe is hybridized with the target nucleic acid sequence, both of the 5'-second hybridization portion and the 3'-first hybridization portion are hybridized with the target nucleic acid sequence and the 5'-second hybridization portion is digested by a 5' to 3' exonuclease activity of a template-dependent nucleic acid polymerase; wherein when the TD probe is hybridized with the non-target nucleic acid sequence, both the 5'-second hybridization portion and the separation portion form a single strand such that the 5'-second hybridization portion is not digested by the 5' to 3' exonuclease activity of the template-dependent nucleic acid polymerase, whereby the TD probe allows discriminating the target nucleic acid sequence from the non-target nucleic acid sequence.

According to a preferred embodiment, the kit further comprises a template-dependent nucleic acid polymerase having a 5' to 3' exonuclease activity.

According to a preferred embodiment, the target nucleic acid sequence used is a pre-amplified nucleic acid sequence by an amplification primer and the kit further comprises the amplification primer.

According to a preferred embodiment, the target nucleic acid sequence comprises at least two types of nucleic acid sequences, the TD probe comprises at least two types of probes, the forward primer comprises at least two types of primers and the reverse primer comprises at least two types of primers.

According to a preferred embodiment, the target nucleic acid sequence comprises a nucleotide variation.

According to a preferred embodiment, the forward primer, the reverse primer or the amplification primer has a dual specificity oligonucleotide (DSO) structure represented by the general formula II.

According to a preferred embodiment, the TD probe has a blocker site containing as a blocker at least one nucleotide resistant to cleavage by an enzyme having a 5' to 3' exonuclease activity and the blocker site is positioned at the 3'-first hybridization portion.

According to a preferred embodiment, the blocker site of the TD probe is positioned on the 3'-first hybridization portion of the TD probe. More preferably, the blocker site of the TD probe is positioned adjacent to the 3'-end of the separation portion.

According to a preferred embodiment, the blocker site comprises 1-10 blockers.

4. Kits for Target Detection Using Ligation Reaction

In further aspect of this invention, there is provided a kit for detecting a target nucleic acid sequence from a DNA or a mixture of nucleic acids using a target discriminative probe (TD probe) by a ligation reaction, which comprises:

(a) a first probe having a hybridizing nucleotide sequence complementary to a first site of the target nucleic acid sequence; and (b) a second probe having a hybridizing nucleotide sequence complementary to a second site of the target nucleic acid sequence which is positioned upstream of the first site;

wherein at least one of the first probe and the second probe has a label to generate a detectable signal; wherein the second probe is a TD probe; wherein the TD probe has a modified dual specificity oligonucleotide (mDSO) structure represented by the following general formula I:

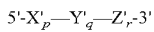   (I)

wherein, $X'_p$ represents a 5'-second hybridization portion having a hybridizing nucleotide sequence complementary to the target nucleic acid sequence; $Y'_q$ represents a separation portion comprising at least three universal bases, $Z'_r$ represents a 3'-first hybridization portion having a hybridizing nucleotide sequence complementary to the target nucleic acid sequence; p, q and r represent the number of nucleotides; and X, Y' and Z' are deoxyribonucleotides or ribonucleotides; the $T_m$ of the 5'-second hybridization portion is lower than that of the 3'-first hybridization portion and the separation portion has the lowest $T_m$ in the three portions of $X'_p$, $Y'_q$ and $Z'_r$; the separation portion separates the 5'-second hybridization portion from the 3'-first hybridization portion in terms of hybridization events to the target nucleic acid sequence, whereby the hybridization specificity of the TD probe are determined dually by the 5'-second hybridization portion and the 3'-first hybridization portion such that the overall hybridization specificity of the TD probe is enhanced;

wherein when the second probe is hybridized with the target nucleic acid sequence, both of the 5'-second hybridization portion and the 3'-first hybridization portion of the second probe are hybridized with the target nucleic acid sequence to allow ligation of the first probe and the second probe; wherein when the second probe is hybridized with the non-target nucleic acid sequence, both of the 5'-second hybridization portion and the separation portion of the second probe form a single strand such that the first probe and the second probe are not ligated, whereby the second probe allows discriminating the target nucleic acid sequence from the non-target nucleic acid sequence;

According to a preferred embodiment, the kit further comprises a ligase to ligate the first probe and the second probe hybridized with the target nucleic acid sequence.

According to a preferred embodiment, the label is a chemical label, an enzymatic label, a radioactive label, a fluorescent label, an interactive label, a luminescent label, a chemiluminescent label or a metal label.

According to a preferred embodiment, the label is the interactive label system comprising a pair of a reporter molecule and a quencher molecule.

According to a preferred embodiment, the first probe has a dual specific oligonucleotide (DSO) structure represented by the general formula II.

According to a preferred embodiment, the target nucleic acid sequence used is a pre-amplified nucleic acid sequence by using an amplification primer and the kit further comprises the amplification primer.

According to a preferred embodiment, the kit is used for a solid phase; wherein the first probe is immobilized through its 5'-end on the surface of a solid substrate and the second probe is not immobilized.

According to a preferred embodiment, the kit is used for a solid phase; wherein the second probe is immobilized through its 3'-end on the surface of the solid substrate and the first probe is not immobilized.

According to a preferred embodiment, the first probe and the second probe are positioned at immediately adjacent locations to each other when hybridized with the target nucleic acid sequence.

According to a preferred embodiment, the target nucleic acid sequence comprises at least two types of nucleic acid sequences and the first probe and the second probe each comprises at least two types of probes.

According to a preferred embodiment, the target nucleic acid sequence comprises a nucleotide variation.

According to a preferred embodiment, the nucleotide variation on the target nucleic acid sequence is present at a site opposite to the 5'-second hybridization portion of the second probe.

5. Kits for Target Detection Based on Hybridization

In still further aspect of this invention, there is provided a kit for detecting a target nucleic acid sequence from a DNA or a mixture of nucleic acids using a target discriminative probe (TD probe), which comprises:

a target discriminative probe (TD probe) having a modified dual specificity oligonucleotide (mDSO) structure represented by the following general formula I to allow for discrimination of the target nucleic acid sequence from a non-target nucleic acid sequence:

$$5'-X'_p-Y'_q-Z'_r-3' \quad \text{(I)}$$

wherein, $X'_p$ represents a 5'-second hybridization portion having a hybridizing nucleotide sequence complementary to the target nucleic acid sequence; $Y'_q$ represents a separation portion comprising at least three universal bases, $Z'_r$ represents a 3'-first hybridization portion having a hybridizing nucleotide sequence complementary to the target nucleic acid sequence; the TD probe is labeled with a fluorescent reporter molecule on the 5'-second hybridization portion; p, q and r represent the number of nucleotides; and X, Y' and Z' are deoxyribonucleotides or ribonucleotides; the $T_m$ of the 5'-second hybridization portion is lower than that of the 3'-first hybridization portion and the separation portion has the lowest $T_m$ in the three portions of $X'_p$, $Y'_q$ and $Z'_r$; the separation portion separates the 5'-second hybridization portion from the 3'-first hybridization portion in terms of hybridization events to the target nucleic acid sequence, whereby the hybridization specificity of the TD probe is determined dually by the 5'-second hybridization portion and the 3'-first hybridization portion such that the overall hybridization specificity of the TD probe is enhanced; wherein when the TD probe is hybridized with the target nucleic acid sequence, both of the 5'-second hybridization portion and the 3'-first hybridization portion are hybridized with the target nucleic acid sequence to induce a change in fluorescence from the fluorescent reporter molecule; wherein when the TD probe is hybridized with the non-target nucleic acid sequence, both the 5'-second hybridization portion and the separation portion form a single strand to induce no change in fluorescence from the fluorescent reporter molecule, whereby the TD probe allows discriminating the target nucleic acid sequence from the non-target nucleic acid sequence.

According to a preferred embodiment, the kit further comprises a reverse primer and a template-dependent nucleic acid polymerase for additionally generating the target nucleic acid sequence hybridizable with the TD probe to enhance the fluorescence change indicative of the presence of the target nucleic acid sequence.

Preferably, the kit further comprises a primer pair composed of two primers as a forward primer and a reverse primer and a template-dependent nucleic acid polymerase for amplifying the target nucleic acid sequence hybridizable with the TD probe by PCR to enhance the fluorescence change indicative of the presence of the target nucleic acid sequence.

Alternatively, the TD probe is additionally labeled with a quencher molecule capable of quenching the fluorescence of the reporter molecule, and the quencher is positioned on the TD probe to induce a self quenching when the TD probe is not involved in hybridization with the target nucleic acid sequence.

Where the present kit comprises the reverse primer or the primer pair, the template-dependent nucleic acid polymerase is preferably a thermostable polymerase with no 5' to 3' exonuclease activity including Stoffel fragment of Taq polymerase and mutant forms of DNA polymerase of *Thermus aquaticus*, *Thermus flavus* or *Thermus thermophilus* (U.S. Pat. No. 5,885,813).

The present kit is in a liquid phase or on a solid phase.

All of the present kits described hereinabove may optionally include the reagents required for performing target amplification PCR reactions (e.g., PCR reactions) such as buffers, DNA polymerase cofactors, and deoxyribonucleotide-5-triphosphates. Optionally, the kits may also include various polynucleotide molecules, reverse transcriptase, various buffers and reagents, and antibodies that inhibit DNA polymerase activity. The kits may also include reagents necessary for performing positive and negative control reactions. Optimal amounts of reagents to be used in a given reaction can be readily determined by the skilled artisan having the benefit of the current disclosure. The kits, typically, are adopted to contain the constituents aforedescribed in separate packaging or compartments.

The features and advantages of this invention will be summarized as follows:

(a) The TD probe having the mDSO structure is hybridized with target nucleic acid sequences through its overall sequence including the 5'-second hybridization portion and the 3'-first hybridization portion. Under the conditions of the target specific hybridization of the TD probe, when the TD probe is hybridized with non-target nucleic acid sequences, its 3'-first hybridization portion non-specifically binds to the non-target nucleic acid sequences but both the 5'-second hybridization portion and the separation portion are not hybridized with the non-target nucleic acid sequence to form a single strand due to their low $T_m$ values.

As such, the 5'-second hybridization portion of the TD probe exhibits distinctly different hybridization patterns for each of target and non-target nucleic acid sequences, discriminating target nucleic acid sequences from non-target nucleic acid sequences with much higher specificity.

(b) The target detection applications using the TD probe show dramatically enhanced target-specificity due to the following target-surveillance events: First, the TD probe having different hybridization patterns for each of target and non-target nucleic acid sequences as described above is capable of discriminating target nucleic acid sequences from non-target nucleic acid sequences with much higher specificity. Second, the occurrence of successive enzymatic reactions (exonucleolytic reaction or ligation) is determined depending on the hybridization patterns of the TD probe, elevating target-specificity in the target detection procedures.

(c) The target-discrimination ability of the TD probe by different hybridization patterns is successfully adopted in target detection methods using 5' to 3' exonuclease activity, completely preventing generation of false positive signals (results). For illustration, where a conventional probe having a label at its 5'-end portion is hybridized with non-target sequences at its 5' portion, the 5' portion is digested by 5' to 3' exonuclease activity to generate false positive signals. Unlikely, even when the TD probe is hybridized with non-target sequences, its 5'-second hybridization portion is not hybridized with non-target sequences to generate no false positive signals.

(d) In real-time PCR method for the detection of target nucleic acid sequences, the TD probe with the reporter molecule and the quencher molecule all positioned on the 5'-second hybridization portion or each positioned on the 5'-second hybridization portion and the separation portion is shown to excellently prevent occurrence of false signals. The conventional technologies such as TaqMan™ probe method are suffering from false positive signals due to non-specific binding of labeled probes, particularly in multiplex target detection. However, the present invention successfully overcomes such problems by using the TD probe having the reporter molecule and the quencher molecule all positioned on the 5'-second hybridization portion. Moreover, the TD probe peculiarly dual-labeled as described above allows for overcoming shortcomings associated with 5' to 3' endonuclease activity of polymerases that becomes problematic depending on types of polymerases and reaction conditions.

(e) The unique hybridization pattern of the TD probe also permits to excellently prevent false positive signals in target detection processes using ligation activity. Generally, target detection methods using ligation of two probes (an upstream first probe and a downstream second probe) demand double strand forms (duplex) of adjacent end portions of the two probes for ligation. In the present ligation assay using the TD probe as a second probe, the 5'-second hybridization portion of the TD probe forms a single strand form when the TD probe is hybridized with non-target sequences, and therefore prevents ligation reactions to generate no false positive signals.

(f) The TD probe shows excellent specificity to discriminate a single nucleotide variation by using the different hybridization patterns of the 5'-second hybridization portion. Even though a single mismatch nucleotide is present between the 5'-second hybridization portion of TD probe and a nucleic acid sequence, the TD probe is able to recognize the sequence as a non-target sequence and its 5'-second hybridization portion forms a single strand resulting in no false positive signals. Specifically, the TD probe has a plausible resolution power in SNP detection.

(g) The TD probe permits to embody microarray systems for accurate and high-throughput solid phase assay. The conventional microarray systems using conventional probes are suffering from false positive signals due to non-specific hybridization of the conventional probes. In contrast, the present solid phase assay using the TD probe together with 5' to 3' exonuclease activity (or ligation activity) allows for detecting target nucleic acid sequences in a real-time manner as well as detecting target nucleic acid sequences in more accurate and rapid manner.

The present invention will now be described in further detail by examples. It would be obvious to those skilled in the art that these examples are intended to be more concretely illustrative and the scope of the present invention as set forth in the appended claims is not limited to or by the examples.

EXAMPLES

Example 1: Evaluation of Cleavage Activity of an Enzyme Having a 5' to 3' Exonuclease Activity on 5'-End Mismatched Probe We examined whether an enzyme having a 5' to 3' exonuclease activity can cleave a probe having mismatched nucleotides at its 5'-end portion.

To examine this evaluation, the synthetic oligonucleotide for *Staphylococcus aureus* (SA) gene was used as templates. Five different types of dual-labeled probes were used and they have a matched sequence, single mismatched nucleotide, three mismatched nucleotides, six mismatched nucleotides and nine mismatched nucleotides at their 5'-end portions, respectively. The dual-labeled probe has 6-FAM (6-carboxyfluorescein) as a fluorescent reporter molecule at its 5'-end and Black Hole Quencher 1 (BHQ-1) as a quencher molecule at its 3'-end portion. The dual-labeled probe is modified by C3 spacer at its 3'-end, such that the dual-labeled probe is not extended.

A DNA polymerase having a 5' to 3' exonuclease activity was used for 5' to 3' exonucleolytic reactions with the dual-labeled probes and the template (*S. aureus* gene). The signals were measured at the hybridization step of each cycle.

The sequences of the synthetic template and the dual-labeled probes for *S. aureus* gene used in this Example are:

```
SA_T70
                                            (SEQ ID NO: 1)
5'-GGTGTAGGTGGTGGCGGTAACAACGCCGTAAACCGAATGATTGAC

CACGGAATGAATAATGTTGAATTTA-3'

SA_P0
                                            (SEQ ID NO: 2)
5'-[FAM]CATTCGGT[T(BHQ-1)]TACGGCGTTGTTACC[C3 spacer]-3'

SA_P1
                                            (SEQ ID NO: 3)
5'-[FAM]CCATTCGGT[T(BHQ-1)]TACGGCGTTGTTACC[C3 spacer]-3'

SA_P3
                                            (SEQ ID NO: 4)
5'-[FAM]TGCCATTCGGT[T(BHQ-1)]TACGGCGTTGTTACC[C3 spacer]-3'

SA_P6
                                            (SEQ ID NO: 5)
5'-[FAM]ACTTGCCATTCGGT[T(BHQ-1)]TACGGCGTTGTTACC[C3 spacer]-3'

SA_P9
                                            (SEQ ID NO: 6)
5'-[FAM]ACAACTTGCCATTCGGT[T(BHQ-1)]TACGGCGTTGTTAC

C[C3 spacer]-3'
(Underlined and bold letters indicate the mismatched nucleo-
tides.)
```

The exonucleolytic reaction was conducted in the final volume of 20 μl containing 0.2 pmole of the synthetic oligonucleotide for *S. aureus* (SEQ ID NO: 1), 5 pmole of the dual-labeled probe (SEQ ID NO: 2, 3, 4, 5 or 6), and 10 μl of 2× Master Mix containing 6 mM $MgCl_2$, 200 μM of dNTPs, and 2 units of DiaStar™ Taq DNA polymerase (Solgent, Korea); the tube containing the reaction mixture was placed in the real-time thermocycler (CFX96, Bio-Rad); the reaction mixture was denatured for 2 min at 95° C. and subjected to 40 cycles of 20 sec at 95° C., and 60 sec at 60° C. Detection of the generated signal was performed at the hybridization step (60° C.) of each cycle.

As shown in FIG. 8, when the dual-labeled probes having the matched sequence and having the single mismatched nucleotide at their 5'-end portions were used, the fluorescent signals for SA were generated (NOs. 1 and 3). On the other hand, no fluorescent signals for SA were observed in case of using the dual-labeled probes having at least three mismatched nucleotides at their 5'-end portions (NOs. 5, 7 and 9). There were no signals in the absence of the template as a negative control (NOs. 2, 4, 6, 8 and 10).

These results indicate that the enzyme having 5' to 3' exonuclease activity dose not cleave the probe having at least three mismatched nucleotides at its 5'-end portion.

Example 2: Evaluation of a Dual-Labeled TD Probe for the Discrimination of a Target Nucleic Acid Sequence and a Non-Target Nucleic Acid Sequence Using an Enzyme Having a 5' to 3' Exonuclease Activity The TD probe of this invention was evaluated whether a dual-labeled TD probe can discriminate a target nucleic acid sequence from a non-target nucleic acid sequence using an enzyme having a 5' to 3' exonuclease activity.

First, we demonstrated whether the target-specific signal can be generated by the different hybridization patterns of the TD probe at its 5'-second hybridization portion.

To examine this evaluation, the synthetic oligonucleotides for *Staphylococcus aureus* (SA) and *Neisseria gonorrhoeae* (NG) genes were used as templates. Two different types of TD probes for each gene have a matched sequence and a mismatched sequence at their 5'-second hybridization portions, respectively. The dual-labeled TD probe has 6-FAM (6-carboxyfluorescein) as a fluorescent reporter molecule at its 5'-end and Black Hole Quencher 1 (BHQ-1) as a quencher molecule at its 3'-first hybridization portion. The dual-labeled TD probe is modified by C3 spacer at its 3'-end, such that the dual-labeled TD probe is not extended.

A DNA polymerase having a 5' to 3' exonuclease activity was used for 5' to 3' exonucleolytic reactions with the dual-labeled TD probe and the target template (*S. aureus* or *N. gonorrhoeae* gene). The signals were measured at the hybridization step of each cycle.

A. The Target-Specific Signal Generation for *S. aureus* Gene Using a TD Probe

The sequences of the synthetic template and the dual-labeled TD probes for *S. aureus* gene used in this Example are:

SA_T70
(SEQ ID NO: 1)
5'-GGTGTAGGTGGTGGCGGTAACAACGCCGTAAACCGAATGATTGAC

CACGGAATGAATAATGTTGAATTTA-3'

SA_TD_M
(SEQ ID NO: 7)
5'-[6-FAM]CATTCCGTGGIIIIICATTCGGTT[T(BHQ-1)]ACGGCG

TTGTTACC[C3 spacer]-3'

SA_TD_m
(SEQ ID NO: 8)
5'-[6-FAM]TGCCTTATAAIIIIICATTCGGTT[T(BHQ-1)]ACGGCG

TTGTTACC[C3 spacer]-3'
(Underlined and bold letters indicate the mismatch nucleotides.)

The exonucleolytic reaction was conducted in the final volume of 20 µl containing 0.2 pmole of the synthetic oligonucleotide for *S. aureus* (SEQ ID NO: 1), 5 pmole of the dual-labeled TD probe (SEQ ID NO: 7 or 8), and 10 µl of 2× Master Mix containing 6 mM MgCl$_2$, 200 µM of dNTPs, and 2 units of DiaStar™ Taq DNA polymerase (Solgent, Korea); the tube containing the reaction mixture was placed in the real-time thermocycler (CFX96, Bio-Rad); the reaction mixture was denatured for 2 min at 95° C. and subjected to 40 cycles of 20 sec at 95° C., and 60 sec at 60° C. Detection of the generated signal was performed at the hybridization step (60° C.) of each cycle.

As shown in FIG. 9A, the fluorescent signal for the target nucleic acid sequence of SA was generated, when the dual-labeled TD probe having the matched sequence at its 5'-second hybridization portion was used (NO. 1). On the other hand, no fluorescent signal for the target nucleic acid sequence of SA was observed in case of using the dual-labeled TD probe having the mismatched sequence at its 5'-second hybridization portion (NO. 3). There were no signals in the absence of the template as a negative control (NOs. 2 and 4).

B. The Target-Specific Signal Generation for *N. gonorrhoeae* Gene Using a TD Probe The sequences of the synthetic template and the dual-labeled TD probes for *N. gonorrhoeae* gene used in this Example are:

NG_T100
(SEQ ID NO: 9)
5'-GAAATTATGCCCTTAAATATGCGAAACACGCCAATGAGGGGC

ATGATGCTTTCTTTTTGTTCTTGCTCGGCAGAGCGAGTGATACCGAT

CCATTGAAAAA-3';

NG_TD_M
(SEQ ID NO: 10)
5'-[6-FAM]AGCATCATGCIIIIIATTGGCGTG[T(BHQ-1)]TTCGCA

TATTTAAG[C3 spacer]-3';

NG_TD_m
(SEQ ID NO: 11)
5'-[6-FAM]GATGCTGTATIIIIIATTGGCGTG[T(BHQ-1)]TTCGCA

TATTTAAG[C3 spacer]-3';
(Underlined and bold letters indicate the mismatch nucleotides.)

The exonucleolytic reaction was conducted as the same protocol used for *S. aureus*, except for the template (2 pmole of *N. gonorrhoeae*) and the dual-labeled TD probes (SEQ ID NO: 10 or 11).

As shown in FIG. 9B, the fluorescent signal for the target nucleic acid sequence of NG was generated, when the dual-labeled TD probe having the matched sequence at its 5'-second hybridization portion was used (NO. 1). On the other hand, no fluorescent signal for the target nucleic acid sequence of NG was observed in case of using the dual-labeled TD probe having the mismatched sequence at its 5'-second hybridization portion (NO. 3). There were no signals in the absence of the template as a negative control (NOs. 2 and 4).

These results showed the target signal generation of the TD probe depending on the hybridization of its 5'-second hybridization portion, indicating that the TD probe can discriminate a target nucleic acid sequence from a non-target nucleic acid sequence.

Example 3: Effect of 5'-End Portions Between TD Probe and Conventional Probe

We examined whether the 5'-end portion of a conventional probe has the same effect of the 5'-second hybridization portion of a TD probe.

For this examination, we used two different types of TD probes; one TD probe has a matched sequence at its 5'-second hybridization portion and the other has three mismatched nucleotides at their 5'-second hybridization portion. The conventional probes have the same sequences of the TD probes except to deoxyinosine.

The synthetic oligonucleotide for *Staphylococcus aureus* (SA) was used as a template. The conventional and TD probes each has 6-FAM (6-carboxyfluorescein) as a fluorescent reporter molecule at its 5'-end and Black Hole Quencher 1 (BHQ-1) as a quencher molecule at its 3'-portion. All probes are modified by C3 spacer at their 3'-ends.

A DNA polymerase having a 5' to 3' exonuclease activity was used for 5' to 3' exonucleolytic reactions with the dual-labeled TD probe and the target template (*S. aureus*).

The sequences of the synthetic template and the dual-labeled conventional and TD probes for *S. aureus* gene used in this Example are:

```
SA_T70
                                            (SEQ ID NO: 1)
5'-GGTGTAGGTGGTGGCGGTAACAACGCCGTAAACCGAATGATTGACCA

CGGAATGAATAATGTTG

AATTTA-3'

SA_TD_M
                                            (SEQ ID NO: 7)
5'-[6-FAM]CATTCCGTGGIIIIICATTCGGTT[T(BHQ-1)]ACGGC

GTTGTTACC[C 3spacer]-3'

SA_TD_m1
                                           (SEQ ID NO: 12)
5'-[6-FAM]CACCTCGTGGIIIIICATTCGGTT[T(BHQ1)]ACGGCGT

TGTTACC[C3 spacer]-3'

SA_Con_M
                                           (SEQ ID NO: 13)
5'-[6-FAM]CATTCCGTGGTCAATCATTCGGTT[T(BHQ-1)]ACGG

CGTTGTTACC[C3 spacer]-3'

SA_Con_m1
                                           (SEQ ID NO: 14)
5'-[6-FAM]CACCTCGTGGTCAATCATTCGGTT[T(BHQ-1)]ACGG

CGTTGTTACC[C3 spacer]-3'
(Underlined and bold letters indicate the mismatch nucleotides.)
```

The exonucleolytic reaction was conducted in the final volume of 20 μl containing 0.2 pmole of the synthetic oligonucleotide for *S. aureus* (SEQ ID NO: 1), 5 pmole of the dual-labeled probe (SEQ ID NO: 7, 12, 13 or 14), and 10 μl of 2× Master Mix containing 6 mM $MgCl_2$, 200 μM of dNTPs, and 2 units of DiaStar™ Taq DNA polymerase (Solgent, Korea); the tube containing the reaction mixture was placed in the real-time thermocycler (CFX96, Bio-Rad); the reaction mixture was denatured for 2 min at 95° C. and subjected to 40 cycles of 20 sec at 95° C., and 60 sec at 60° C. Detection of the generated signal was performed at the hybridization step (60° C.) of each cycle.

Figure 10:
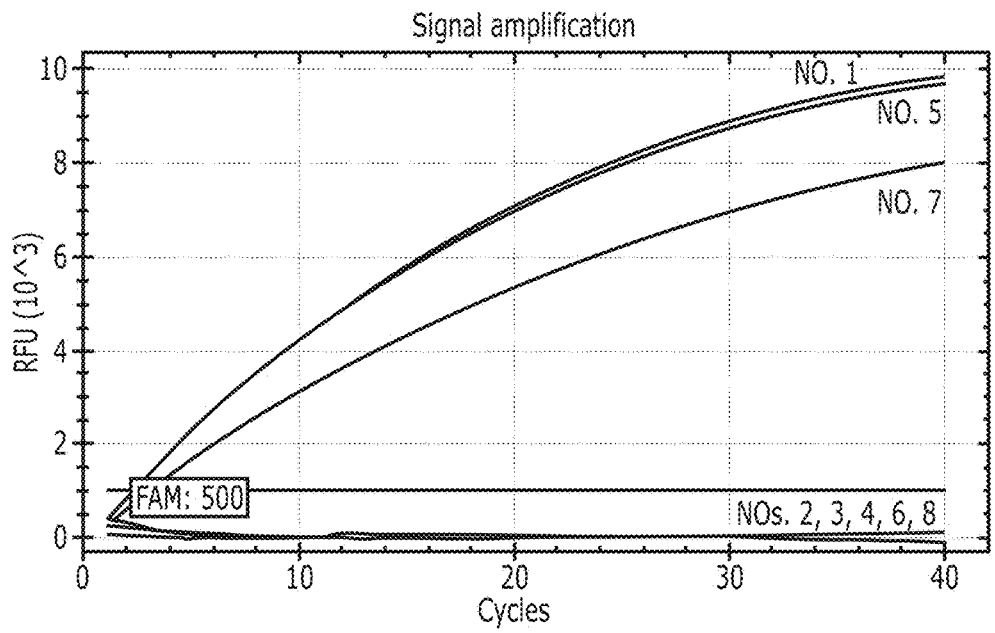
FIG. 10 shows the results of comparison between a TD probe and a conventional probe for the detection of *Staphylococcus aureus* gene. Symbols, [1]Template is a synthetic oligonucleotide for *Staphylococcus aureus* gene; [2]Probe has a reporter molecule at its 5'-end and a quencher molecule at its 3'-end portion; [3]SA_TD_M is a TD probe and has a matched sequence at its 5'-second hybridization portion; [4]SA_TD_m1 is a TD probe and has three mismatched nucleotides at its 5'-second hybridization portion; [5]SA_Con_M is a conventional probe and has a matched sequence at its 5'-end portion; [6]SA_Con_m1 is a conventional probe and has three mismatched nucleotides at its 5'-end portion.

As shown in FIG. 10, the fluorescent signal for the target nucleic acid sequence was generated, when the dual-labeled TD probe having the matched sequence at its 5'-second hybridization portion was used (NO. 1). Interestingly, in the case of the TD probe having the three mismatched nucleotides at its 5'-second hybridization portion, no signal was observed (NO. 3). In contrast, when the conventional probes having three mismatched nucleotides as well as having the matched sequence at their 5'-end portions were used (NOs. 5 and 7), the signals were generated. There were no signals in the absence of the template as a negative control (NOs. 2, 4, 6 and 8)

These results showed that in contrast to the TD probe, the conventional probe generated the false positive signal on non-specific hybridization. Therefore, it could be understood that a TD probe can detect a target nucleic acid sequence without false positive signals.

Example 4: Real-Time PCR Using a TD Probe for the Detection of a Target Nucleic Acid Sequence We applied the TD probe in real-time PCR reaction for the detection of a target nucleic acid sequence with a DNA polymerase having 5' to 3' exonuclease activity.

For this application, genomic DNAs of *Staphylococcus aureus* and *Neisseria gonorrhoeae* were extracted from each cell line and used. TD probe has either a matched or a mismatched sequence at its 5'-second hybridization portion. Both of a reporter molecule and a quencher molecule were positioned at the 5'-second hybridization portion of the dual-labeled TD probe.

A. Real-Time PCR for Detection of *S. aureus* Gene

When the target nucleic acid sequence of the *S. aureus* gene is used as a template, the sequences of the primers and the dual-labeled TD probes used in this Example are:

```
SA_F
                                           (SEQ ID NO: 15)
5'-TGTTAGAATTTGAACAAGGATTTAAIIIIIITAGCGACTTT-3'

SA_R
                                           (SEQ ID NO: 16)
5'-GATAAGTTTAAAGCTTGACCGTCIIIIIITGATAGCGAT-3'

SA_TD2_M
                                           (SEQ ID NO: 17)
5'-[6-FAM]CATTCCG[T(BHQ-1)]GGIIIIICATTCGGTTTACGGC

GTTGTTACC[C3 spacer]-3'

SA_TD2_m
                                           (SEQ ID NO: 18)
5'-[6-FAM]TGCCTTA[T(BHQ-1)]]AAIIIIICATTCGGTTTACGG

CGTTGTTACC[C3 spacer]-3';
(Underlined and bold letters indicate the mismatch nucleotides.)
```

The real-time PCR reaction was conducted in the final volume of 20 μl containing 1 ng of *S. aureus* genomic DNA, 5 pmole of dual-labeled TD probe (SEQ ID NO: 17 or 18), 10 pmole of forward primer (SEQ ID NO: 15), 10 pmole of reverse primer (SEQ ID NO: 16) and 10 μl of 2× Master Mix containing 6 mM $MgCl_2$, 200 μM of dNTPs, and 2 units of DiaStar™ Taq DNA polymerase (Solgent, Korea); the tube containing the reaction mixture was placed in the real-time thermocycler (CFX96, Bio-Rad); the reaction mixture was denatured for 2 min at 95° C. and subjected to 40 cycles of 20 sec at 95° C., and 60 sec at 60° C. Detection of the generated signal was performed at the hybridization step (60° C.) of each cycle.

Figure 11A:
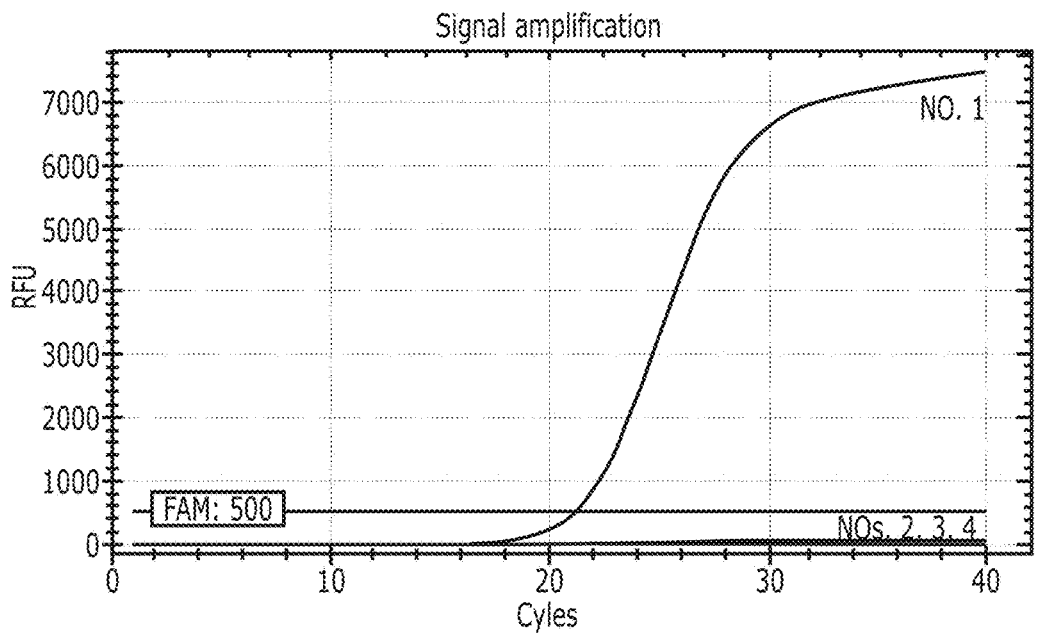
FIGS. 11A and 11B show the results of a real-time PCR reaction for the detection of a target nucleic acid sequence using a TD probe having both a reporter molecule and a quencher molecule at its 5'-second hybridization portion.

As shown in FIG. 11A, the target fluorescent signal for *S. aureus* gene was generated when the dual-labeled TD probe having the matched sequence at its 5'-second hybridization portion was used (NO. 1). On the other hand, no fluorescent signal for the target nucleic acid sequence of *S. aureus* gene was observed in case of using the dual-labeled TD probe having the mismatched sequence at its 5'-second hybridization portion (NO. 3), indicating that the report molecule and the quencher molecule positioned on the 5'-second hybridization portion were not separated. There were no signals in the absence of the template as a negative control (NOs. 2 and 4)

B. Real-Time PCR for Detection of *N. gonorrhoeae* Gene

When the target nucleic acid sequence of the *N. gonorrhoeae* gene is used as a template, the sequences of the primers and the dual-labeled TD probes used in this Example are:

```
NG_F
                                    (SEQ ID NO: 19)
5'-TACGCCTGCTACTTTCACGCTIIIIIGTAATCAGATG-3'

NG_R
                                    (SEQ ID NO: 20)
5'-CAATGGATCGGTATCACTCGCIIIIICGAGCAAGAAC-3'

NG_TD2_M
                                    (SEQ ID NO: 21)
5'-[6-FAM]AGCATCA[T(BHQ-1)]GCIIIIIATTGGCGTGTTTCG

CATATTTAAG[C3 spacer]-3';

NG_TD2_m
                                    (SEQ ID NO: 22)
5'-[6-FAM]GATGCTG[T(BHQ-1)]ATIIIIIATTGGCGTGTTTCGC

ATATTTAAG[C3 spacer]-3';
(Underlined and bold letters indicate the mismatch nucleo-
tides.)
```

The real-time PCR reaction was conducted as the same protocol used for *S. aureus*, except for template (1 ng of *N. gonorrhoeae*), dual-labeled TD probes (SEQ ID NOs: 21 and 22), and primers (SEQ ID NOs: 19 and 20)

Figure 11B:
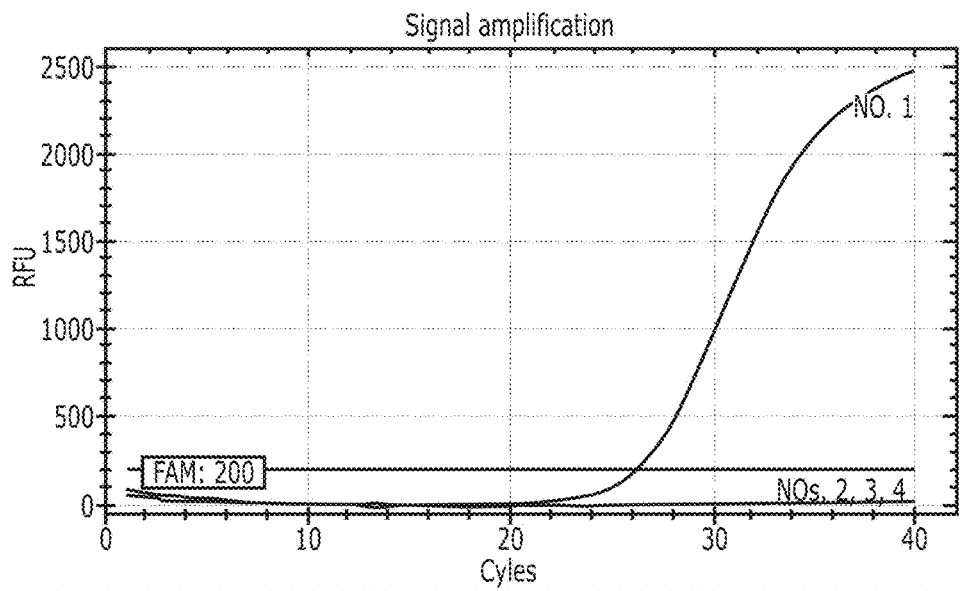

As shown in FIG. 11B, the target fluorescent signal for *N. gonorrhoeae* gene was generated when the dual-labeled TD probe having the matched sequence at its 5'-second hybridization portion was used (NO. 1). On the other hand, no fluorescent signal for the target nucleic acid sequence of *N. gonorrhoeae* gene was observed in case of using the dual-labeled TD probe having the mismatched sequence at its 5'-second hybridization portion (NO. 3), indicating that the report molecule and the quencher molecule positioned on the 5'-second hybridization portion were not separated. There were no signals in the absence of the template as a negative control (NOs. 2 and 4).

These results showed that the TD probe having an interactive label system on its 5'-second hybridization portion can be used in the real-time PCR for discriminating a target nucleic acid sequence from a non-target nucleic acid sequence.

Example 5: Discrimination of Single Nucleotide Variation Using a Dual-Labeled TD Probe in Real-Time PCR Reaction We examined whether a TD probe can discriminate a single nucleotide variation on a nucleic acid sequence.

For this examination, TD probe has either a matched sequence or a single mismatched nucleotide at its 5'-second hybridization portion. Both of a reporter molecule and a quencher molecule were positioned at its 5'-second hybridization portion of the dual-labeled TD probe.

The genomic DNA of *S. aureus* is used as a template. The sequences of the primers and the dual-labeled TD probes used in this Example are:

```
SA_F
                                    (SEQ ID NO: 15)
5'-TGTTAGAATTTGAACAAGGATTTAAIIIIITAGCGACTTT-3'

SA_R
                                    (SEQ ID NO: 16)
5'-GATAAGTTTAAAGCTTGACCGTCIIIIITGATAGCGAT-3'

SA_TD_S_M
                                    (SEQ ID NO: 23)
5'-[6-FAM]TTCCG[T(BHQ-1)]GGIIIIICATTCGGTTTACGGCGTT

GTTACC[C3 spacer]-3'

SA_TD_S_m
                                    (SEQ ID NO: 24)
5'-[6-FAM]TTCTG[T(BHQ-1)]GGIIIIICATTCGGTTTACGGCGTT

GTTACC[C3 spacer]-3'
```

The real-time PCR reaction was conducted in the final volume of 20 µl containing 500 pg of *S. aureus* genomic DNA, 5 pmole of dual-labeled TD probe (SEQ ID NO: 23 or 24), 10 pmole of forward primer (SEQ ID NO: 15), 10 pmole of reverse primer (SEQ ID NO: 16) and 10 µl of 2× Master Mix containing 6 mM $MgCl_2$, 200 µM of dNTPs, and 2 units of DiaStar™ Taq DNA polymerase (Solgent, Korea); the tube containing the reaction mixture was placed in the real-time thermocycler (CFX96, Bio-Rad); the reaction mixture was denatured for 2 min at 95° C. and subjected to 40 cycles of 20 sec at 95° C., and 60 sec at 63° C. Detection of the generated signal was performed at the hybridization step (63° C.) of each cycle.

Figure 12:
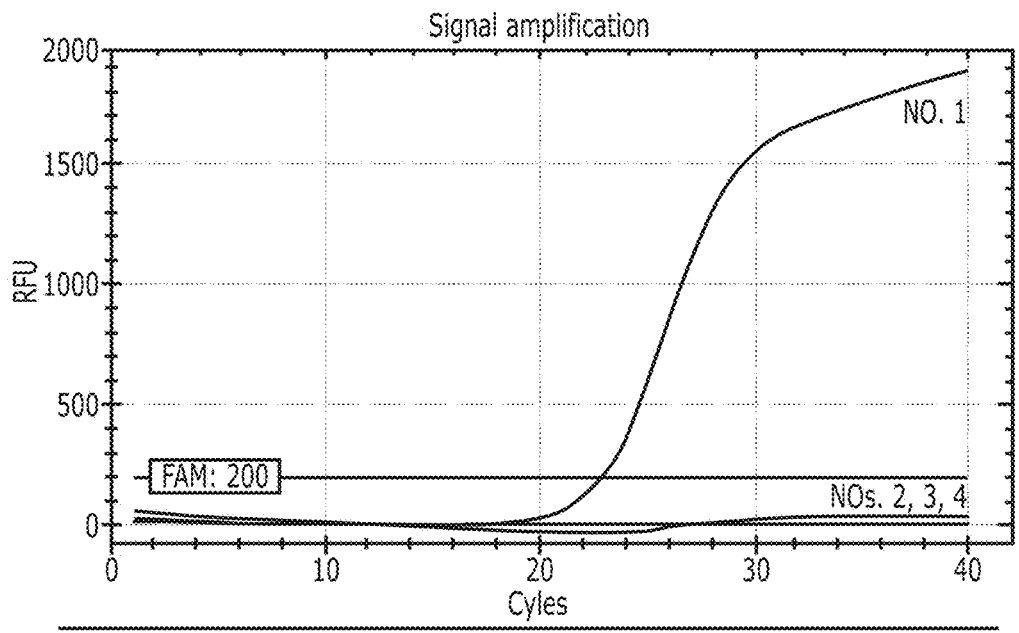
FIG. 12 shows the results of a real-time PCR reaction for the discrimination of a single nucleotide mismatch using a TD probe having both a reporter molecule and a quencher molecule at its 5'-second hybridization portion. Symbols, [1]Template is a genomic DNA of *Staphylococcus aureus*; [2]TD probe has both a reporter molecule and a quencher molecule at its 5'-second hybridization portion; [3]SA_TD_S_M has a matched sequence at its 5'-second hybridization portion; [4]SA_TD_S_m has a single mismatched nucleotide at its 5'-second hybridization portion.

As shown in FIG. 12, the fluorescent signal for *S. aureus* was generated when the dual-labeled TD probe having a matched sequence at its 5'-second hybridization portion was used (NO. 1). On the other hand, no fluorescent signal was observed in case of using the dual-labeled TD probe having a single mismatched nucleotide at its 5'-second hybridization portion (NO. 3). There were no signals in the absence of the template as a negative control (NOs. 2 and 4).

These results showed the different hybridization pattern of TD probe depending on even single nucleotide mismatch at its 5'-second hybridization portion. Therefore, it could be understood that a TD probe has high specificity to discriminate a single nucleotide variation including SNP without false positive signals in real-time PCR reaction.

Example 6: Evaluation of an Immobilized TD Probe on Solid Phase Using an Enzyme Having a 5' to 3' Exonuclease Activity We further evaluated whether an immobilized TD probe can discriminate a target nucleic acid sequence from a non-target nucleic acid sequence using an enzyme having a 5' to 3' exonuclease activity in solid phase.

To examine this evaluation, the synthetic oligonucleotide for *Staphylococcus aureus* (SA) gene was used as a template. The TD probe has either a matched or a mismatched sequence at its 5'-second hybridization portion. The TD probe has a Quasar570 as a fluorescent reporter molecule at its 3'-first hybridization portion, a Black Hole Quencher 2 (BHQ-2) as a quencher molecule at its 5'-end and poly(T)₇ as a linker arm. The dual-labeled TD probes were immobilized on the surface of solid substrate by using an amino group (AminnoC7) at its 3'-end. Bst DNA polymerase having a 5' to 3' exonuclease activity was used for 5' to 3' exonucleolytic reactions.

The sequences of the synthetic template and the dual-labeled TD probes used in this Example are:

SA_T70
                                                    (SEQ ID NO: 1)
5'-GGTGTAGGTGGTGGCGGTAACAACGCCGTAAACCGAATGATTGA

CCACGGAATGAATAATGTTGAATTTA-3'

SA_TD1_Chip_M
                                                    (SEQ ID NO: 25)
5'-[BHQ2]CATTCCGTGGIIIIICATTCGGTT[T(Quasar570)]ACG GCGTTGTTACCTTTTT[AminoC7]-3'

SA_TD1_Chip_m
                                                    (SEQ ID NO: 26)
5'-[BHQ-2]TGCCTTATAAIIIIICATTCGGTT[T(Quasar570)]AC GGCGTTGTTACCTTTTT[AminoC7]
(Underlined and bold letters indicate the mismatch nucleotides.)

NSB9 NHS slides (NSBPOSTECH, Korea) were used for fabrication of two different types of TD probes (SEQ ID NO: 25 and 26). The TD probes dissolved in NSB spotting buffer at the final concentration of 20 μM were printed on the NSB9 NHS slides with OmniGrid Accent Microarrayer (DIGILAB, US). Each TD probe was spotted side by side in a 2×1 format (duplicate spots), and the resulting microarray was incubated in a chamber maintained at ~85% humidity for overnight. The slides were then washed in a buffer solution containing 2×SSPE (0.3 M sodium chloride, 0.02 M sodium hydrogen phosphate and 2.0 mM EDTA), pH 7.4 and 7.0 mM SDS at 37° C. for 10 min to remove the non-specifically bound TD probe and rinsed with distilled water. Then, the DNA-functionalized slides were dried using slide centrifuge and stored in dark at 4° C. until use.

The exonucleolytic reaction was conducted on the surface of the DNA-functionalized slide in the final volume of 30 μl containing 10 pmole of synthetic oligonucleotide for SA (SEQ ID NO: 1), and 3 μl of 10× reaction buffer, 0.6 μl of 10 mM each of dNTPs, 2 units of Bst DNA polymerase (NEB, USA). The whole mixture was applied to a chamber assembled on the surface of NSB glass slide on which the TD probes were cross-linked. The slide was placed on in situ block in a thermocycler (Genepro B4I, China). The exonucleolytic reaction was carried out for 30 min at 50° C. and stopped by washing at 95° C. for 1 min with distilled water. The image acquisition was carried out by the use of Confocal Laser Scanner, Axon GenePix4100A (molecular Device, US) with scanning at 5-μm pixel resolution. The fluorescence intensity was analyzed by the use of quantitative microarray analysis software, GenePix pro5.1 software (Molecular Device, US). The fluorescence intensity was expressed as spot-medians after local background subtractions. Each spot was duplicated for the test of reproducibility. The fluorescence intensity indicates the average value of the duplicated spots.

Figure 13A:
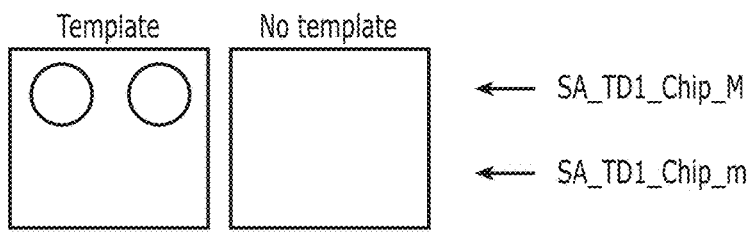
FIGS. 13A and 13B show the results of the discrimination of a target nucleic acid sequence from a non-target nucleic acid sequence depending on the hybridization of the 5'-second hybridization portion of a dual-labeled TD probe immobilized on a surface of solid substrate. Each spot was duplicated for the test of reproducibility. The fluorescence intensity indicates the average value of the duplicated spots. Symbols: SA_TD1_Chip_M is a TD probe having a matched sequence at its 5'-second hybridization portion; SA_TD1_Chip_m is a TD probe having a mismatched sequence at its 5'-second hybridization portion.
Figure 13B:
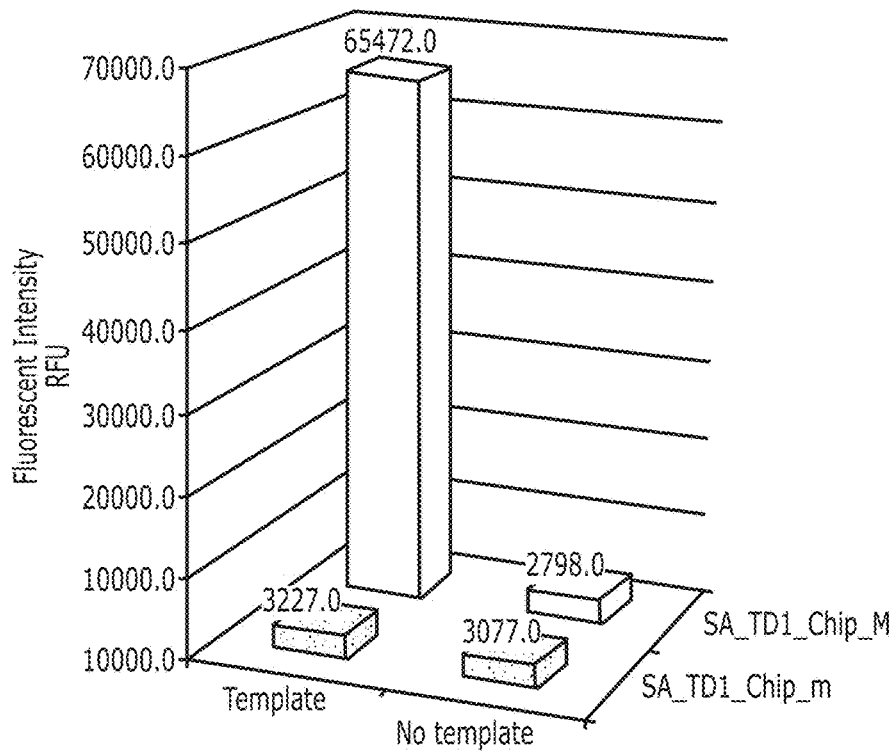

As shown in FIG. 13, the fluorescent signal for *S. aureus* was generated when the dual-labeled TD probe having the matched sequence at its 5'-second hybridization portion was used with the template (SA_TD1_Chip_M, RFU 65472.0±4.2). On the other hand, no fluorescent signal for *S. aureus* was observed in case of using the dual-labeled TD probe having the mismatched sequence at its 5'-second hybridization portion (SA_TD1_Chip_m, RFU 3227.0±17.0). There were no signals in the absence of the template as a negative control (SA_TD1_Chip_M, RFU 2798.0±4.2 or SA_TD1_Chip_m, RFU 3077.0±9.9).

These results showed that the immobilized TD probe can be applied for microarray assays to discriminate target nucleic acid sequences from non-target nucleic acid sequences.

Example 7: Effect of the 5'-Second Hybridization Portion of Immobilized TD Probes We further examined whether immobilized TD probes can eliminate false positive signals on solid phase by the effect of the 5'-second hybridization portion.

For this examination, the synthetic oligonucleotide for *Staphylococcus aureus* (SA) gene was used as a template. The TD probe has either a matched sequence or three mismatched nucleotides at its 5'-second hybridization portion. The conventional probes have the same sequences of the TD probes except to deoxyinosine. The TD and conventional probes have Quasar570 as a fluorescent reporter molecule at its 3'-first hybridization portion, Black Hole Quencher 2 (BHQ-2) as a quencher molecule at its 5'-end and poly(T)₇ as a linker arm. The dual-labeled probes were immobilized on the surface of solid substrate by using an amino group (AminnoC7) at their 3'-ends. Bst DNA polymerase having a 5' to 3' exonuclease activity was used for 5' to 3' exonucleolytic reactions.

The sequences of the synthetic template and the dual-labeled TD and conventional probes used in this Example are:

SA_T70
                                                    (SEQ ID NO: 1)
5'-GGTGTAGGTGGTGGCGGTAACAACGCCGTAAACCGAATGA

TTGACCACGGAATGAATAATGTTGAATTTA-3'

SA_TD1_Chip_M
                                                    (SEQ ID NO: 25)
5'-[BHQ2]CATTCCGTGGIIIIICATTCGGTT[T(Quasar570)]AC GGCGTTGTTACCTTTTT[AminoC7]-3'

SA_TD1_Chip_m1
                                                    (SEQ ID NO: 27)
5'-[BHQ-2]CACCTCGTGGIIIIICATTCGGTT[T(Quasar570)]AC GGCGTTGTTACCTTTTT[AminoC7]-3'

SA_Con_Chip_M
                                                    (SEQ ID NO: 28)
5'-[BHQ-2]CATTCCGTGGTCAATCATTCGGTT[T(Quasar570)]A CGGCGTTGTTACCTTTTT[AminoC7]-3'

SA_Con_Chip_m1
                                                    (SEQ ID NO: 29)
5'-[BHQ-2]CACCTCGTGGTCAATCATTCGGTT[T(Quasar570)]A CGGCGTTGTTACCTTTTT[AminoC7]-3'
(Underlined and bold letters indicate the mismatch nucleotides.)

NSB9 NHS slides (NSBPOSTECH, Korea) were used for fabrication of the probes (SEQ ID NOs: 25, 27, 28 and 29). Each probe dissolved in NSB spotting buffer at the final concentration of 20 μM was printed on the NSB9 NHS slide with OmniGrid Accent Microarrayer (DIGILAB, US). Each probe was spotted side by side in a 2×1 format (duplicate spots), and the resulting microarray was incubated in a chamber maintained at ~85% humidity for overnight. The slides were then washed in a buffer solution containing 2×SSPE (0.3 M sodium chloride, 0.02 M sodium hydrogen phosphate and 2.0 mM EDTA), pH 7.4 and 7.0 mM SDS at 37° C. for 10 min to remove the non-specifically bound probes and rinsed with distilled water. Then the DNA-functionalized slides were dried using slide centrifuge and store in dark at 4° C. until use.

The exonucleolytic reaction was conducted on the surface of the DNA-functionalized slide in the final volume of 30 μl containing 10 pmole of synthetic oligonucleotide for SA (SEQ ID NO: 1), and 3 μl of 10× reaction buffer, 0.6 μl of 10 mM each of dNTPs, 2 units of Bst DNA polymerase (NEB, USA). The whole mixture was applied to a chamber assembled on the surface of NSB glass slide on which the probes were cross-linked. The slide was placed on in situ block in a thermocycler (Genepro B4I, China). The exonucleolytic reaction was carried out for 30 min at 50° C. and stopped by washing at 95° C. for 1 min with distilled water. The image acquisition was carried out by the use of Confocal Laser Scanner, Axon GenePix4100A (molecular Device, US) with scanning at 5-μm pixel resolution. The fluorescence intensity was analyzed by the use of quantitative microarray analysis software, GenePix pro5.1 software (Molecular Device, US). The fluorescence intensity was expressed as spot-medians after local background subtractions. Each spot was duplicated for the test of reproducibility. The fluorescence intensity indicates the average value of the duplicated spots.

As shown in FIG. 14, the fluorescent signal for the target nucleic acid sequence of SA was generated when the dual-labeled immobilized TD probe having a matched sequence at its 5'-second hybridization portion was used with the template (SA_TD1_Chip_M, RFU: 65467.0±5.7). In case of using the TD probe having three mismatched nucleotides at its 5'-second hybridization portion, no signal was observed (SA_TD1_Chip_m1, RFU: 6679.5±222.7). On the other hand, the signals were generated when the conventional probes having three mismatched nucleotides (SA_Con_Chip_m1, RFU: 65464.0±5.7) as well as having the matched sequence (SA_Con_Chip_M, RFU: 65464.5±6.4) were used. There were no signals in the absence of the template as a negative control (SA_TD1_Chip_M, RFU: 2716.5±12.0) (SA_TD1_Chip_m1, RFU: 2810.5±14.8) (SA_Con_Chip_m1, RFU: 3216.5±41.7) (SA_Con_Chip_M, RFU: 2749.5±19.1)

These results showed that in contrast to the immobilized TD probe, the immobilized conventional probe generated the false positive signal on non-specific hybridization. Therefore, it could be understood that immobilized TD probes can detect target nucleic acid sequences without false positive signals.

Example 8: Detection of Target Nucleic Acid Sequences Using Single-Labeled TD Probes Immobilized on the Surface of Solid Substrate We further applied single-labeled TD probes for the detection of target nucleic acid sequences on solid phase.

For this application, the synthetic oligonucleotide for *Staphylococcus aureus* (SA) gene was used as a template. A TD probe has either a matched or a mismatched sequence at its 5'-second hybridization portion. The TD probe has 6-FAM or 6-TAMRA (6-Carboxytetramethylrhodamine) as a fluorescent reporter molecule at its 5'-end and poly(T), as a linker arm. The single-labeled TD probe was immobilized on the surface of solid substrate by using an amino group (AminnoC7) at its 3'-end. Bst or Taq polymerase having a 5' to 3' exonuclease activity was used for 5' to 3' exonucleolytic reactions.

A. Signal Generation by Performing Exonucleolytic Reaction

The sequences of the synthetic template and single-labeled TD probes used in this reaction are:

SA_T70
(SEQ ID NO: 1)
5'-GGTGTAGGTGGTGGCGGTAACAACGCCGTAAACCGAATGATTGA

CCACGGAATGAATAATGTTG

AATTTA-3'

SA_TD2_Chip_M
(SEQ ID NO: 30)
5'-[6-FAM]CATTCCGTGGIIIIICATTCGGTTTACGGCGTTGTTACC

TTTTT[AminoC7]-3'

SA_TD2_Chip_m
(SEQ ID NO: 31)
5'-[6-FAM]TGCCTTATAAIIIIICATTCG61TTACGGCGTTGTTACC TTTTT[AminoC7]-3'
(Underlined and bold letters indicate the mismatch nucleotides.)

NSB9 NHS slides (NSBPOSTECH, Korea) were used for fabrication of the probes (SEQ ID NOs: 30 and 31). Each probe dissolved in NSB spotting buffer at the final concentration of 20 μM was printed on the NSB9 NHS slide with OmniGrid Accent Microarrayer (DIGILAB, US). Each probe was spotted side by side in a 2×1 format (duplicate spots), and the resulting microarray was incubated in a chamber maintained at ~85% humidity for overnight. The slides were then washed in a buffer solution containing 2×SSPE (0.3 M sodium chloride, 0.02 M sodium hydrogen phosphate and 2.0 mM EDTA), pH 7.4 and 7.0 mM SDS at 37° C. for 10 min to remove the non-specifically bound probes and rinsed with distilled water. Then the DNA-functionalized slides were dried using slide centrifuge and store in dark at 4° C. until use.

The exonucleolytic reaction was conducted on the surface of the DNA-functionalized slide in the final volume of 30 μl containing 10 pmole of synthetic oligonucleotide for SA (SEQ ID NO: 1), and 3 μl of 10× reaction buffer, 50 μM each of dNTPs, 2 units of Bst DNA polymerase. The whole mixture was applied to a chamber assembled on the surface of NSB glass slide on which the probes were cross-linked. The slide was placed on in situ block of a thermocycler (Genepro B4I, China). The exonucleolytic reaction was carried out for 30 min at 50° C. and stopped by washing at 95° C. for 1 min with distilled water. The image acquisition was carried out by the use of Confocal Laser Scanner, Axon GenePix4300A (molecular Device, USA) with scanning at 5-μm pixel resolution. The fluorescence intensity was analyzed by the use of quantitative microarray analysis software, GenePix software (Molecular Device, USA). The fluorescence intensity was expressed as spot-medians after local background subtractions. Each spot was duplicated for the test of reproducibility. The fluorescence intensity indicates the average value of the duplicated spots.

B. Signal Generation by Performing Cyclic Exonucleolytic Reaction

The sequences of the synthetic template and single-labeled TD probes used in this reaction are:

```
SA_T70
                                             (SEQ ID NO: 1)
5'-GGTGTAGGTGGTGGCGGTAACAACGCCGTAAACCGAATGATTG

ACCACGGAATGAATAATGTTG

AATTTA-3'

SA_TD2_Chip_M_2
                                            (SEQ ID NO: 32)
5'-[6-TAMRA]CATTCCGTGGIIIIICATTCGGTTTACGGCGTTGTTAC CTTTTT[AminoC7]-3'

SA_TD2_Chip_m_2
                                            (SEQ ID NO: 33)
5'-[6-TAMRA]TGCCTTATAAIIIIICATTCGGTTTACGGCGTTGTTAC CTTTTT[AminoC7]-3'
(Underlined and bold letters indicate the mismatch nucleotides.)
```

NSB9 NHS slides (NSBPOSTECH, Korea) were used for fabrication of the probes (SEQ ID NOs: 32 and 33). Each probe dissolved in NSB spotting buffer at the final concentration of 20 μM was printed on the NSB9 NHS slide with OmniGrid Accent Microarrayer (DIGILAB, US). Each probe was spotted side by side in a 2×1 format (duplicate spots), and the resulting microarray was incubated in a chamber maintained at ~85% humidity for overnight. The slides were then washed in a buffer solution containing 2×SSPE (0.3 M sodium chloride, 0.02 M sodium hydrogen phosphate and 2.0 mM EDTA), pH 7.4 and 7.0 mM SDS at 37° C. for 10 min to remove the non-specifically bound probes and rinsed with distilled water. Then the DNA-functionalized slides were dried using slide centrifuge and store in dark at 4° C. until use.

The cyclic exonucleolytic reaction was conducted on the surface of the DNA-functionalized slide in the final volume of 30 μl containing 10 pmole of synthetic oligonucleotide for SA (SEQ ID NO: 1), and 3 μl of 10× reaction buffer (5 mM MgCl$_2$), 50 μM each of dNTPs, 2 units of Taq DNA polymerase (Solgent, Korea). The whole mixture was applied to a chamber assembled on the surface of NSB glass slide on which the probes were cross-linked. The slide was placed on in situ block in a thermocycler (Genepro B4I, China). The thermocycling was carried out as follows: 2 min denaturation at 95° C. and a cycle (5, 10, 20, 30, 40 or 50 cycles) of 95° C. for 20 sec and 55° C. for 20 sec. The image acquisition was carried out by the use of Confocal Laser Scanner, Axon GenePix4100A (molecular Device, USA) with scanning at 5-μm pixel resolution. The fluorescence intensity was analyzed by the use of quantitative microarray analysis software, GenePix software (Molecular Device, USA). The fluorescence intensity was expressed as spot-medians after local background subtractions. Each spot was duplicated for the test of reproducibility. The fluorescence intensity indicates the average value of the duplicated spots.

In the case of exonucleolytic reaction, when the single-labeled immobilized TD probe having a matched sequence at its 5'-second hybridization portion was used with the template, the fluorescent signal on the solid substrate was finally eliminated. In the case of cyclic exonucleolytic reaction, the fluorescent intensity on the solid substrate was decreased depending on the number of cycles.

Example 9: Detection of a Single Nucleotide Variation Using a TD Probe and Ligase on Solid Phase We further examined whether a TD probe can discriminate a single nucleotide variation on a nucleic acid sequence by a ligase reaction on solid phase.

For this examination, a first probe having DSO structure has Quasar570 as a reporter molecule at its 5'-end and is used as a mobilized probe. The TD probe as a second probe has either a matched sequence or a single mismatched nucleotide at its 5'-second hybridization portion. The TD probe has poly(T), as a linker arm. The TD probe was immobilized on the surface of solid substrate by using an amino group (AminnoC7) at its 3'-end. The synthetic oligonucleotide for *Staphylococcus aureus* (SA) gene was used as a template. Ampligase Thermostable DNA Ligase was used for the ligation.

The sequences of the synthetic template and the first and second (TD) probes used in this Example are:

```
SA_T110:
                                            (SEQ ID NO: 34)
5'-TGTAGGTGGTGGCGGTAACAACGCCGTAAACCGAATGATTGAC

CACGGAATGAATAATGTTGAATTTATCGCTATCAACACAGACGGTCA

AGCTTTAAACTTATCTAAAG-3'

SA_TD_Chip_S_M:
                                            (SEQ ID NO: 35)
5'-TTCCGTGGIIIIICATTCGGTTTACGGCGTTGTTACCTTTTT

[AminoC7]-3'

SA_TD_Chip_S_m:
                                            (SEQ ID NO: 36)
5'-TTCTGTGGIIIIICATTCGGTTTACGGCGTTGTTACCTTTTT

[AminoC7]-3'

SA_Chip_DSO:
                                            (SEQ ID NO: 37)
5'-[Quasar570]ACCGTCTGTGTTGATAGCGATAAIIIIIAC ATTATTCA-3'
(Underlined and bold letter indicates the mismatch nucleotide.)
```

NSB9 NHS slides (NSBPOSTECH, Korea) were used for fabrication of the TD probes (SEQ ID NOs: 35 and 36). Each probe dissolved in NSB spotting buffer at the final concentration of 20 μM was printed on the NSB9 NHS slide with OmniGrid Accent Microarrayer (DIGILAB, US). Each probe was spotted side by side in a 2×1 format (duplicate spots), and the resulting microarray was incubated in a chamber maintained at ~85% humidity for overnight. The slides were then washed in a buffer solution containing 2×SSPE (0.3 M sodium chloride, 0.02 M sodium hydrogen phosphate and 2.0 mM EDTA), pH 7.4 and 7.0 mM SDS at 37° C. for 10 min to remove the non-specifically bound probes and rinsed with distilled water. Then the DNA-functionalized slides were dried using slide centrifuge and store in dark at 4° C. until use.

The ligase reaction was conducted on the surface of the DNA-functionalized slide in the final volume of 30 μl containing 10 pmole of synthetic template for SA (SEQ ID NO: 34), 5 pmole of first probe (SEQ ID NO: 37) and 3 μl of Ampligase 10× reaction buffer containing 20 mM Tris-HCl (pH 8.3), 25 mM KCl, 10 mM MgCl2, 0.5 mM NAD, and 0.01% Triton® X-100, 0.2 μl of Ampligase Thermostable DNA Ligase (5 U/μl) (Epicentre Biotechnologies, USA). The whole mixture was applied to a chamber assembled on the surface of NSB glass slide on which the probes were cross-linked. The reaction was carried out as follows: the hybridization of the target nucleic acid, the first probe and the immobilized TD probe was carried out at 45° C. for 5 min and the ligase reaction was further carried out for 30 min at 65° C. The reaction was stopped and denaturation was performed by washing at 95° C. for 2 min with distilled water. The image acquisition was carried out by the use of Confocal Laser Scanner, Axon GenePix4100A (molecular Device, USA) with scanning at 5-μm pixel resolution. The fluorescence intensity was analyzed by the use of quantitative microarray analysis software, GenePix software (Molecular Device, USA). The fluorescence intensity was expressed as spot-medians after local background subtractions. Each spot was duplicated for the test of reproducibility. The fluorescence intensity indicates the average value of the duplicated spots.

The fluorescent signal for the target nucleic acid sequence of SA was generated when the TD probe having a matched sequence at its 5'-second hybridization portion was used as the second probe with the template. In case of using the TD probe having the single mismatched nucleotide at its 5'-second hybridization portion as the second probe, no signal was observed. These results demonstrate that our ligation reaction allows for detection of a single nucleotide variation.

Example 10: Detection of Target Nucleic Acid Sequence by Fluorescence Change Upon Hybridization of 5'-Second Hybridization Portion of TD Probe We further examined whether a TD probe having a fluorescent molecule at its 5'-second hybridization portion can be applied for a target detection based on fluorescent signal change depending on the hybridization of the labeled portion.

For this application, genomic DNA of *Staphylococcus aureus* was used as a template. The TD probe has either a matched or mismatched sequence at its 5'-second hybridization portion. The fluorescent molecule was linked to the internal nucleotide of the 5'-second hybridization portion of the TD probe. A template-dependent nucleic acid polymerase having no 5' to 3' exonuclease activity was used for the target amplification.

The sequences of the primers and the single-labeled TD probes used in this Example are:

```
SA_F
                                      (SEQ ID NO: 15)
5'-TGTTAGAATTTGAACAAGGATTTAAIIIIITAGCGACTTT-3'

SA_R
                                      (SEQ ID NO: 16)
5'-GATAAGTTTAAAGCTTGACCGTCIIIIITGATAGCGAT-3'

SA_TD3_M
                                      (SEQ ID NO: 38)
5'-CATTCCG[T(FAM)]GGIIIIICATTCGGTTTACGGCGTTGTTACC

[C3 spacer]-3'

SA_TD3_m
                                      (SEQ ID NO: 39)
5'-TGCCTTA[T(FAM)]]AAIIIIICATTCGGTTTACGGCGTTGTTACC

[C3 spacer]-3';
(Underlined and bold letters indicate the mismatch nucleotides.)
```

The real-time PCR reaction was conducted in the final volume of 20 μl containing 1 ng of *S. aureus* genomic DNA, 5 pmole of single-labeled TD probe (SEQ ID NO: 38 or 39), 10 pmole of forward primer (SEQ ID NO: 15), 10 pmole of reverse primer (SEQ ID NO: 16), 2 μl of 10× Stoffel buffer [containing 100 mM Tris-HCl (pH 8.3) and 100 mM KCl], 200 μM each of four dNTPs (dATP, dCTP, dGTP and dTTP), 5 mM of MgCl$_2$ and 1 unit of AmpliTaq® DNA polymerase, Stoffel Fragment (Applied BioSystems, US); the tube containing the reaction mixture was placed in the real-time thermocycler (CFX96, Bio-Rad); the reaction mixture was denatured for 2 min at 95° C. and subjected to 40 cycles of 20 sec at 95° C., 30 sec at 55° C., and 10 sec at 72° C. Detection of the generated signal was performed at the hybridization step (55° C.) of each cycle.

Our experimental results address that the TD probe permits to discriminately detect target sequences by measuring fluorescent change from a single label molecule depending on hybridization of the 5'-second hybridization portion.

Exemplary target nucleic acids are provided below:

| Target sequence | Genbank Accession number | Date released |
|---|---|---|
| Respiratory disease | | |
| Influenza A virus | J02167.1 | 1993 Aug. 2 |
| Influenza B virus | K01395.1 | 1993 Aug. 2 |
| Respiratory syncytial virus A | AF348809.1 | 2002 Jan. 14 |
| Respiratory syncytial virus B | M17213.1 | 1993 Aug. 3 |
| Adenovirus | NC_001405.1 | 2000 Aug. 1 |
| Enterovirus | NC_001430.1 | 2000 Aug. 1 |
| Parainfluenza virus 1 | NC_003461.1 | 2002 Mar. 26 |
| Parainfluenza virus 2 | NC_003443.1 | 2002 Mar. 16 |
| Parainfluenza virus 3 | NC_001796.2 | 2000 Aug. 1 |
| Parainfluenza virus 4 | FJ608692.1 | 2009 May 11 |
| Metapneumovirus | NC_004148.2 | 2002 Sep. 11 |
| Bocavirus | NC_007455.1 | 2005 Oct. 5 |
| Rhinovirus | K02121.1 | 1993 Aug. 2 |
| Coronavirus NL63 | AY567487.2 | 2004 May 17 |
| Coronavirus 229E | NC_002645.1 | 2001 Jan. 13 |
| Coronavirus OC43 | AY391777.1 | 2003 Oct. 22 |
| *Mycoplasma pneumoniae* | U00089.2 | 1999 Dec. 22 |
| *Chlamydophila pneumoniae* | AE001363.1 | 1999 Dec. 22 |
| *Legionella pneumophila* | NC_002942.5 | 2002 Apr. 8 |
| *Haemophilus influenza* | L42023.1 | 1999 Dec. 22 |
| *Streptococcus pneumoniae* | NC_003098.1 | 2001 Oct. 3 |

-continued

| Target sequence | Genbank Accession number | Date released |
| --- | --- | --- |
| *Bordetella pertussis* | NC_002929.2 | 2002 Apr. 8 |
| *Bordetella parapertussis* | NC_002928.3 | 2002 Apr. 8 |
| Gastrointestinal disease | | |
| Norovirus GI | NC_001959.2 | 2000 Aug. 1 |
| Norovirus GII | AY032605.1 | 2001 Dec. 31 |
| Rotavirus | NC_007558.1 | 2005 Nov. 2 |
| Adenovirus | NC_001405.1 | 2000 Aug. 1 |
| Astrovirus | NC_001943.1 | 2000 Aug. 1 |
| Sapovirus | AY237423.2 | 2004 Feb. 26 |
| *Campylobacter* spp. | NC_002163.1 | 2001 Sep. 27 |
| *Clostridium difficile* (toxin B) | X53138.1 | 1993 Apr. 21 |
| *Salmonella* spp. | AE006468.2 | 2001 Oct. 26 |
| *Shigella* spp. | M76444.1 | 1993 Apr. 26 |
| *Vibrio* spp. | NZ_AAKJ00000000.3 | 2005 Sep. 17 |
| *Yersinia enterocolitica* | NC_008800.1 | 2007 Jan. 19 |
| *Aeromonas* spp. | CP000462.1 | 2006 Nov. 6 |
| *Clostridium difficile* (hypervirulent) | DQ363256.1 | 2006 Feb. 11 |
| *E. coli* O157 | S83460.1 | 1997 Mar. 28 |
| Enterohemorrhagic *E. coli*, | AF162758.1 | 1999 Aug. 9 |
| Enteropathogenic *E. coli* | AF043226.1 | 1998 Jan. 27 |
| Enterotoxigenic *E. coli* | AB011677.1 | 1998 Apr. 18 |
| Enteroaggregative *E. coli* | Z18751.1 | 1993 Jun. 16 |
| *Giardia lamblia* | AACB02000076.1 | 2007 Sep. 24 |
| *Entamoeba histolytica* | M84216.1 | 1993 Apr. 26 |
| *Cryptosporidium* spp. | AAEE00000000.1 | 2004 Apr. 5 |
| *Blastocystis hominis* | AY244620.1 | 2004 Feb. 11 |
| *Dientamoeba fragilis* | U37461.1 | 1996 Jul. 12 |
| *Cyclospora cayetanensis* | AF111183.1 | 1999 Mar. 12 |
| *Clostridium perfringens* | NC_003366.1 | 2002 Jan. 24 |
| Verocytotoxin-producing *E. coli* (VTEC) | M36727.1 | 1993 Apr. 26 |
| Sexually transmitted disease | | |
| *Atopobium vaginae* | NZ_ACGK00000000.2 | 2009 Feb. 18 |
| *Lactobacillus* spp. | NZ_ACKR00000000.1 | 2009 Apr. 27 |
| *Bacteroides fragilis* | NC_003228.3 | 2002 Apr. 8 |
| *Megasphaera* type 1 | ADGP00000000.1 | 2010 Mar. 9 |
| Bacterial vaginosis-associated bacteria 2 (BVAB2) | AF407407.1 | 2001 Sep. 5 |
| *Mobiluncus* spp. | NZ_ACKW00000000.1 | 2009 Apr. 27 |
| *Chlamydia trachomatis* | AE001273.1 | 2001 Jan. 9 |
| *Neisseria gonorrhoeae* | NC_002946.2 | 2002 Apr. 8 |
| *Mycoplasma genitalium* | L43967.2 | 1999 Dec. 22 |
| *Mycoplasma hominis* | AJ243692.1 | 1999 Dec. 3 |
| *Trichomonas vaginalis* | AAHC00000000.1 | 2005 May 25 |
| *Ureaplasma urealyticum* | AAYQ00000000.2 | 2007 May 21 |
| *Ureaplasma parvum* | NC_002162.1 | 2001 Mar. 16 |
| Herpes simplex virus type 1 | X14112.1 | 1993 Apr. 21 |
| Herpes simplex virus type 2 | Z86099.2 | 1997 Mar. 5 |
| Varicella-zoster virus | X04370.1 | 1993 Apr. 21 |
| Cytomegalovirus | X17403.1 | 1993 Apr. 21 |
| Lymphogranuloma venereum | NC_010287.1 | 2008 Jan. 25 |
| *Treponema pallidum* | AE000520.1 | 1999 Dec. 22 |
| *Haemophilus ducreyi* | NC_002940.2 | 2002 Apr. 8 |
| *Candida albicans* | M90812.1 | 1993 Apr. 27 |
| *Candida glabrata* | NC_006036.2 | 2004 Jul. 14 |
| *Candida tropicalis* | AAFN00000000.2 | 2005 Mar. 16 |
| *Candida parapsilosis* | CABE00000000.1 | 2008 Dec. 17 |
| *Candida krusei* | FJ445765.1 | 2008 Dec. 29 |
| *Candida lusitaniae* | AAFT00000000.1 | 2005 Mar. 16 |
| *Candida dubliniensis* | FM992695.1 | 2009 Feb. 16 |
| *Mobiluncus curtisii* | X53186.1 | 1993 Apr. 21 |
| *Mobiluncus mulieris* | NZ_ACKW00000000.1 | 2009 Apr. 27 |
| Group B *Streptococcus* | NC_004116.1 | 2002 Aug. 29 |
| Cervical cancer | | |
| Human papillomavirus type 16 | AY686584.1 | 2005 May 21 |
| Human papillomavirus type 18 | A06328.1 | 1993 Nov. 2 |
| Human papillomavirus type 26 | X74472.1 | 1993 Sep. 3 |
| Human papillomavirus type 31 | J04353.1 | 1993 Aug. 2 |
| Human papillomavirus type 33 | M12732.1 | 1993 Aug. 2 |
| Human papillomavirus type 35 | M74117.1 | 1993 Aug. 2 |
| Human papillomavirus type 39 | U45905.1 | 1996 Mar. 1 |
| Human papillomavirus type 45 | X74479.1 | 1993 Sep. 3 |
| Human papillomavirus type 51 | M62877.1 | 1993 Aug. 2 |
| Human papillomavirus type 52 | X74481.1 | 1993 Sep. 3 |

| Target sequence | Genbank Accession number | Date released |
|---|---|---|
| Human papillomavirus type 53 | X74482.1 | 1993 Sep. 3 |
| Human papillomavirus type 56 | X74483.1 | 1993 Sep. 3 |
| Human papillomavirus type 58 | D90400.1 | 1993 Apr. 29 |
| Human papillomavirus type 59 | X77858.1 | 1994 Oct. 11 |
| Human papillomavirus type 66 | U31794.1 | 1995 Oct. 18 |
| Human papillomavirus type 68 | DQ080079.1 | 2005 Dec. 6 |
| Human papillomavirus type 69 | AB027020.1 | 2000 Feb. 14 |
| Human papillomavirus type 73 | X94165.1 | 1996 Aug. 15 |
| Human papillomavirus type 82 | AB027021.1 | 2000 Feb. 14 |
| Human papillomavirus type 6 | AF092932.1 | 1999 Oct. 1 |
| Human papillomavirus type 11 | M14119.1 | 1993 Aug. 2 |
| Human papillomavirus type 40 | X74478.1 | 1993 Sep. 3 |
| Human papillomavirus type 42 | GQ472847.1 | 2009 Oct. 6 |
| Human papillomavirus type 43 | AJ620205.1 | 2004 Jan. 12 |
| Human papillomavirus type 44 | U31788.1 | 1995 Oct. 18 |
| Human papillomavirus type 54 | U37488.1 | 1995 Oct. 12 |
| Human papillomavirus type 61 | U31793.1 | 1995 Oct. 18 |
| Human papillomavirus type 70 | U21941.1 | 1995 Mar. 20 |
| *Tuberculosis* | | |
| *Mycobacterium tuberculosis* | AL123456.3 | 2003 May 9 |
| *Sepsis* | | |
| *Streptococcus agalactiae* | NC_004116.1 | 2002 Aug. 29 |
| *Streptococcus pyogenes* | AE004092.2 | 2001 Jun. 4 |
| *Streptococcus pneumoniae* | NC_003098.1 | 2001 Oct. 3 |
| *Enterococcus faecalis* | AE016830.1 | 2003 Mar. 28 |
| *Enterococcus gallinarum* | NZ_ACAJ00000000.1 | 2009 May 21 |
| *Enterococcus faecium* | NZ_ACHL00000000.1 | 2009 Mar. 11 |
| *Staphylococcus epidermidis* | NC_002976.3 | 2002 Apr. 8 |
| *Staphylococcus haemolyticus* | AP006716.1 | 2005 Jun. 30 |
| *Staphylococcus aureus* | NC_002745.2 | 2001 Oct. 4 |
| *Pseudomonas aeruginosa* | AE004091.2 | 2001 Jan. 9 |
| *Acinetobacter baumannii* | CP000521.1 | 2007 Mar. 1 |
| *Stenotrophomonas maltophilia* | NC_010943.1 | 2008 Jun. 17 |
| *Serratia marcescens* | AC148075.4 | 2004 Jan. 30 |
| *Bacteroides fragilis* | NC_003228.3 | 2002 Apr. 8 |
| *Salmonella typhi* (*Salmonella enterica* subsp. *enterica*) | NC_003198.1 | 2001 Nov. 7 |
| *Klebsiella pneumoniae* | AP006725.1 | 2005 Jan. 5 |
| *Klebsiella oxytoca* | L27431.1 | 1994 Apr. 19 |
| *Proteus mirabilis* | NC_010554.1 | 2008 Aug. 26 |
| *Escherichia coli* | AE005174.2 | 2005 Jan. 27 |
| *Enterobacter cloacae* | CP001918.1 | 2010 Apr. 23 |
| *Enterobacter aerogenes* | X00254.1 | 1993 Apr. 21 |
| *Candida albicans* | M90812.1 | 1993 Apr. 27 |
| *Candida tropicalis* | AAFN00000000.2 | 2005 Mar. 16 |
| *Candida parapsilosis* | CABE00000000.1 | 2008 Dec. 17 |
| *Candida glabrata* | NC_006036.2 | 2004 Jul. 14 |
| *Candida krusei* | FJ445765.1 | 2008 Dec. 29 |
| *Aspergillus fumigatus* | AL713629.1 | 2002 Mar. 21 |
| *Meningitis* | | |
| Herpes simplex virus type 1 | X14112.1 | 1993 Apr. 21 |
| Herpes simplex virus type 2 | Z86099.2 | 1997 Mar. 5 |
| Varicella-zoster virus | X04370.1 | 1993 Apr. 21 |
| Epstein-Barr virus | V01555.2 | 1993 Apr. 21 |
| Cytomegalovirus | X17403.1 | 1993 Apr. 21 |
| Enteroviruses | NC_001612.1 | 2000 Aug. 1 |
| *Streptococcus pneumoniae* | NC_003098.1 | 2001 Oct. 3 |
| *Neisseria meningitides* | AE002098.2 | 2001 Jan. 9 |
| *Haemophilus influenza* | L42023.1 | 1999 Dec. 22 |
| *Listeria monocytogenes* | NC_002973.6 | 2002 Apr. 8 |
| Group B *Streptococcus* (*Streptococcus agalactiae*) | NC_004116.1 | 2002 Aug. 29 |
| *Others* | | |
| Vancomycin-resistant *Enterococci* (VanA; VanB; VanC) | M97297.1; U94530.1; U72706.1 | 1993 Apr. 26; 1997 Jul. 2; 1997 Mar. 4 |
| Clarithomycin-resistant *Helicobacter pylori* (A2142G; A2143G) | AE000511.1 | 1999 Dec. 22 |
| ApoE genotypes (SNP in codon112 and codon158) | U35114.1 | 1995 Nov. 2 |
| Factor II (G20210A); Factor V (R506Q, H1299R, Y1702C); MTHFR (C677T, | NM_000506.4; NM_000130.4 | 1999 Mar. 24; 1999 Mar. 24; |

| Target sequence | Genbank Accession number | Date released |
| --- | --- | --- |
| A1298C) | AH007464.3 | 1999 Mar. 4 |
| BRAF (V600E) | M95712.2 | 1993 Apr. 27 |
| BCR/ABL (b2a2, b3a2, e1a2, c3a2, b1a1, b3a3, b2a3, e1a3) | M15025.1 | 1993 Apr. 27 |
| *Homo sapiens* | | |
| (chromosome 1) | NC_000001.11 | 2002 Aug. 29 |
| (chromosome 2) | NC_000002.12 | 2002 Aug. 29 |
| (chromosome 3) | NC_000003.12 | 2002 Aug. 29 |
| (chromosome 4) | NC_000004.12 | 2002 Aug. 29 |
| (chromosome 5) | NC_000005.10 | 2002 Aug. 22 |
| (chromosome 6) | NC_000006.12 | 2002 Aug. 30 |
| (chromosome 7) | NC_000007.14 | 2002 Aug. 5 |
| (chromosome 8) | NC_000008.11 | 2002 Aug. 29 |
| (chromosome 9) | NC_000009.12 | 2002 Aug. 29 |
| (chromosome 10) | NC_000010.11 | 2002 Aug. 29 |
| (chromosome 11) | NC_000011.10 | 2002 Aug. 29 |
| (chromosome 12) | NC_000012.12 | 2002 Aug. 29 |
| (chromosome 13) | NC_000013.11 | 2002 Aug. 29 |
| (chromosome 14) | NC_000014.9 | 2002 Aug. 29 |
| (chromosome 15) | NC_000015.10 | 2002 Aug. 29 |
| (chromosome 16) | NC_000016.10 | 2002 Aug. 29 |
| (chromosome 17) | NC_000017.11 | 2002 Aug. 29 |
| (chromosome 18) | NC_000018.10 | 2002 Aug. 29 |
| (chromosome 19) | NC_000019.10 | 2002 Aug. 29 |
| (chromosome 20) | NC_000020.11 | 2002 Aug. 30 |
| (chromosome 21) | NC_000021.9 | 2002 Aug. 30 |
| (chromosome 22) | NC_000022.11 | 2002 Aug. 30 |
| (chromosome X) | NC_000023.11 | 2002 Aug. 29 |
| (chromosome Y) | NC_000024.10 | 2002 Aug. 29 |

INCORPORATION BY REFERENCE

The entire contents of all patents, published patent applications, and other references cited herein are hereby expressly incorporated herein in their entireties by reference.

Having described a preferred embodiment of the present invention, it is to be understood that variants and modifications thereof falling within the spirit of the invention may become apparent to those skilled in this art, and the scope of this invention is to be determined by appended claims and their equivalents.

What is claimed is:
1. A method for detecting a target nucleic acid sequence from a DNA or a mixture of nucleic acids in a sample using a target discriminative probe (TD probe), which comprises the steps of:
(a) preparing a reaction mixture containing a TD probe having a hybridizing nucleotide sequence complementary to the target nucleic acid sequence wherein the target nucleic acid sequence is derived from any one selected from the group consisting of Influenza A virus; Influenza B virus; Respiratory syncytial virus A; Respiratory syncytial virus B; Adenovirus; Enterovirus; Parainfluenza virus 1; Parainfluenza virus 2; Parainfluenza virus 3; Parainfluenza virus 4; Metapneumovirus; Bocavirus; Rhinovirus; Coronavirus NL63; Coronavirus 229E; Coronavirus OC43; *Mycoplasma pneumoniae; Chlamydophila pneumoniae; Legionella pneumophila; Haemophilus* influenza; *Streptococcus pneumoniae; Bordetella pertussis; Bordetella parapertussis*; Norovirus GI; Norovirus GII; Rotavirus; Astrovirus; Sapovirus; *Campylobacter* spp.; *Clostridium difficile* (toxin B); *Salmonella* spp.; *Shigella* spp.; *Vibrio* spp.; *Yersinia enterocolitica; Aeromonas* spp.; *Clostridium difficile* (hypervirulent); *E. coli* 0157; Enterohemorrhagic *E. coli*; Enteropathogenic *E. coli*; Enterotoxigenic *E. coli*; Enteroaggregative *E. coli*; *Giardia lamblia; Entamoeba histolytica; Cryptosporidium* spp.; *Blastocystis hominis; Dientamoeba fragilis; Cyclospora cayetanensis; Clostridium perfringens*; Verocytotoxin-producing *E. coli* (VTEC); Atopobium vaginae; *Lactobacillus* spp.; *Bacteroides fragilis; Megasphaera type* 1; Bacterial vaginosis-associated bacteria 2 (BV AB2); *Mobiluncus* spp.; *Chlamydia trachomatis; Neisseria gonorrhoeae; Mycoplasma genitalium; Mycoplasma hominis; Trichomonas vaginalis; Ureaplasma urealyticum; Ureaplasma parvum*; Herpes simplex virus type 1; Herpes simplex virus type 2; Varicella-zoster virus; Cytomegalovirus; Lymphogranuloma venereum; *Treponema pallidum; Haemophilus ducreyi; Candida albicans; Candida glabrata; Candida tropicalis; Candida parapsilosis; Candida krusei; Candida lusitaniae; Candida* dubliniensis; *Mobiluncus curtisii; Mobiluncus mulieris*; Group B *Streptococcus*; Human papillomavirus type 16; Human papillomavirus type 18; Human papillomavirus type 26; Human papillomavirus type 31; Human papillomavirus type 33; Human papillomavirus type 35; Human papillomavirus type 39; Human papillomavirus type 45; Human papillomavirus type 51; Human papillomavirus type 52; Human papillomavirus type 53; Human papillomavirus type 56; Human papillomavirus type 58; Human papillomavirus type 59; Human papillomavirus type 66; Human papillomavirus type 68; Human papillomavirus type 69; Human papillomavirus type 73; Human papillomavirus type 82; Human papillomavirus type 6; Human papillomavirus type 11; Human papillomavirus type 40; human papillomavirus type 42; Human papillomavirus type 43; Human papillomavirus type 44; Human papillomavirus type 54; Human papillomavirus type 61; Human papillomavirus type 70; *Mycobacterium tuberculosis; Streptococcus agalactiae; Streptococcus pyogenes; Enterococcus faecalis; Enterococcus gallinarum; Enterococcus faecium; Staphylococcus epidermidis; Staphylococcus haemolyticus; Staphylococcus aureus; Pseudomonas aeruginosa; Acinetobacter baumannii; Stenotrophomonas maltophilia; Serratia marcescens; Salmonella typhi* (*Salmonella enterica* subsp. *enterica*), *Klebsiella pneumoniae; Klebsiella oxytoca; Proteus mirabilis; Escherichia coli; Enterobacter cloacae; Enterobacter aerogenes; Aspergillus fumigatus*; Epstein-Barr virus; Enteroviruses; *Neisseria meningitides; Listeria monocytogenes*; Group B *Streptococcus* (*Streptococcus agalactiae*); Vancomycin-resistant Enterococci (VanA; VanB; VanC); Clarithomycin-resistant *Helicobacter pylori* (A2142G; A2143G); ApoE genotypes (SNP in codon112 and codon158); Factor II (G20210A); Factor V (R506Q, H1299R, YI 702C); MTHFR (C677T, A1298C); BRAF (V600E); BCR/ABL (b2a2, b3a2, ela2, c3a2, blal, b3a3, b2a3, ela3); and *Homo sapiens;*
(b) hybridizing the target nucleic acid sequence with the TD probe in the reaction mixture; wherein the TD probe has a modified dual specificity oligonucleotide (mDSO) structure represented by the following general formula I:

5'-X'p-Y'q-Z'r-3'     (I)

wherein, X'p represents a 5'-second hybridization portion having a hybridizing nucleotide sequence complementary to the target nucleic acid sequence; Y'q represents a separation portion comprising at least three contiguous universal bases, Z'r represents a 3'-first hybridization portion having a hybridizing nucleotide sequence complementary to the target nucleic acid sequence; the TD probe is dually labeled with a fluorescent reporter molecule and a quencher molecule that quenches the fluorescence of the reporter molecule; the fluorescent reporter molecule and the quencher molecule all are positioned on the 5'-second hybridization portion or the fluorescent reporter molecule and the quencher molecule each is positioned on each different portion of the 5'-second hybridization portion and the separation portion; p, q and r represent the number of nucleotides; and the sugar moiety in X', Y' and Z' is deoxyribose or ribose; the Tm of the 5'-second hybridization portion is lower than that of the 3'-first hybridization portion and the separation portion has the lowest Tm in the three portions of X'p, Y'q and Z'r; the 5'-second hybridization portion is 5-11 nucleotides in length, the 3'-first hybridization portion is 15-30 nucleotides in length and the 3'-first hybridization portion is longer than the 5'-second hybridization portion; the separation portion separates the 5'-second hybridization portion from the 3'-first hybridization portion in terms of hybridization events to the target nucleic acid sequence, whereby the hybridization specificity of the TD probe is determined dually by the 5'-second hybridization portion and the 3'-first hybridization;
wherein the TD probe is not extended;
wherein when the TD probe is hybridized with the target nucleic acid sequence, both of the 5'-second hybridization portion and the 3'-first hybridization portion are hybridized with the target nucleic acid sequence and the 5'-second hybridization portion is digested by an enzyme having a 5' to 3' exonuclease activity;
wherein when the TD probe is hybridized with the non-target nucleic acid sequence, both the 5'-second hybridization portion and the separation portion form a single strand such that the 5'-second hybridization portion is not digested by the enzyme having the 5' to 3' exonuclease activity, whereby the TD probe allows discriminating the target nucleic acid sequence from the non-target nucleic acid sequence;

wherein the hybridization is performed under conditions such that the hybridization solely by the 5'-second hybridization portion is prevented;

wherein the universal base is selected from the group consisting of deoxyinosine, inosine, 7-deaza-2'-deoxyinosine, 2-aza-2'-deoxyinosine, 2'-OMe inosine, 2'-F inosine, deoxy 3-nitropyrrole, 3-nitropyrrole, 2'-OMe 3-nitropyrrole, 2'-F 3-nitropyrrole, 1-(2'-deoxy-beta-D-ribofuranosyl)-3-nitropyrrole, deoxy 5-nitroindole, 5-nitroindole, 2'-OMe 5-nitroindole, 2'-F 5-nitroindole, deoxy 4-nitrobenzimidazole, 4-nitrobenzimidazole, deoxy 4-aminobenzimidazole, 4-aminobenzimidazole, deoxy nebularine, 2'-F nebularine, 2'-F 4-nitrobenzimidazole, PNA-5-introindole, PNA-nebularine, PNA-inosine, PNA-4-nitrobenzimidazole, PNA-3-nitropyrrole, morpholino-5-nitroindole, morpholinonebularine, morpholino-inosine, morpholino-4-nitrobenzimidazole, morpholino-3-nitropyrrole, phosphoramidate-5-nitroindole, phosphoramidate-nebularine, phosphoramidate-inosine, phosphoramidate-4-nitrobenzimidazole, phosphoramidate-3-nitropyrrole, 2'-O-methoxyethyl inosine, 2'0-methoxyethyl nebularine, 2'-O-methoxyethyl 5-nitroindole, 2'-O-methoxyethyl 4-nitro-benzimidazole, 2'-O-methoxyethyl 3-nitropyrrole, and combinations thereof;

(c) contacting the resultant of step (b) to the enzyme having the 5' to 3' exonuclease activity; wherein when the TD probe is hybridized with the target nucleic acid sequence, the 5'-second hybridization portion is digested by the enzyme having the 5' to 3' exonuclease activity to separate the fluorescent reporter molecule from the quencher molecule on the TD probe, resulting in generation of a fluorescence signal; wherein when the TD probe is hybridized with the non-target nucleic acid sequence, the 5'-second hybridization portion is not digested by the enzyme having the 5' to 3' exonuclease activity, resulting in no fluorescence signal; and (d) detecting the fluorescence signal, such that the fluorescence signal generated by the digestion on the 5'-second hybridization portion is indicative of the presence of the target nucleic acid sequence.

2. The method of claim 1, wherein the enzyme having the 5' to 3' exonuclease activity is a template-dependent nucleic acid polymerase having the 5' to 3' exonuclease activity.

3. The method of claim 1, wherein the step (b) is carried out using the TD probe together with an forward primer to be hybridized with a site downstream of a hybridized site of the TD probe and the enzyme having the 5' to 3' exonuclease activity is a template-dependent nucleic acid polymerase having the 5' to 3' exonuclease activity such that the forward primer is extended by the template-dependent nucleic acid polymerase in the step (c).

4. The method of claim 3, wherein the target nucleic acid sequence comprises at least two types of nucleic acid sequences, the TD probe comprises at least two types of probes and the forward primer comprises at least two types of primers or the reverse primer comprises at least two types of primers.

5. The method of claim 1, wherein the step (b) is carried out using the TD probe together with a reverse primer and the enzyme having the 5' to 3' exonuclease activity is a template-dependent nucleic acid polymerase having the 5' to 3' exonuclease activity such that the step (c) produces the target nucleic acid sequence hybridizable with the TD probe by an extension reaction of the reverse primer by the template-dependent nucleic acid polymerase.

6. The method of claim 1, wherein the method further comprises repeating the steps (b)-(c) or (b)-(d) with denaturation between repeating cycles.

7. The method of claim 1, wherein the target nucleic acid sequence comprises at least two types of nucleic acid sequences and the TD probe comprises at least two types of probes.

8. The method of claim 1, wherein the target nucleic acid sequence comprises a nucleotide variation and the nucleotide variation on the target nucleic acid sequence is present at a site opposite to the 5'-second hybridization portion of the TD probe.

9. The method of claim 1, wherein the TD probe has a blocker site containing as a blocker at least one nucleotide resistant to cleavage by the enzyme having 5' to 3' exonuclease activity and the blocker site is positioned at the 3'-first hybridization portion of the TD probe.

10. A method for detecting a target nucleic acid sequence on a solid phase from a DNA or a mixture of nucleic acids in a sample using a target discriminative probe (TD probe), which comprises the steps of:

(a) preparing a TD probe having a hybridizing nucleotide sequence complementary to the target nucleic acid sequence wherein the target nucleic acid sequence is derived from any one selected from the group consisting of Influenza A virus; Influenza B virus; Respiratory syncytial virus A; Respiratory syncytial virus B; Adenovirus; Enterovirus; Parainfluenza virus 1; Parainfluenza virus 2; Parainfluenza virus 3; Parainfluenza virus 4; Metapneumovirus; Bocavirus; Rhinovirus; Coronavirus NL63; Coronavirus 229E; Coronavirus OC43; *Mycoplasma pneumoniae*; *Chlamydophila pneumoniae*; *Legionella pneumophila*; *Haemophilus* influenza; *Streptococcus pneumoniae*; *Bordetella pertussis*; *Bordetella parapertussis*; Norovirus GI; Norovirus GII; Rotavirus; Astrovirus; Sapovirus; *Campylobacter* spp.; *Clostridium difficile* (toxin B); *Salmonella* spp.; *Shigella* spp.; *Vibrio* spp.; *Yersinia enterocolitica*; *Aeromonas* spp.; *Clostridium difficile* (hypervirulent); *E. coli* 0157; Enterohemorrhagic *E. coli*; Enteropathogenic *E. coli*; Enterotoxigenic *E. coli*; Enteroaggregative *E. coli*; *Giardia lamblia*; *Entamoeba histolytica*; *Cryptosporidium* spp.; *Blastocystis hominis*; *Dientamoeba fragilis*; *Cyclospora cayetanensis*; *Clostridium perfringens*; Verocytotoxin-producing *E. coli* (VTEC); *Atopobium vaginae*; *Lactobacillus* spp.; *Bacteroides fragilis*; *Megasphaera* type 1; Bacterial vaginosis-associated bacteria 2 (BV AB2); Mobiluncus spp.; *Chlamydia trachomatis*; *Neisseria gonorrhoeae*; *Mycoplasma genitalium*; *Mycoplasma hominis*; *Trichomonas vaginalis*; *Ureaplasma urealyticum*; *Ureaplasma parvum*; Herpes simplex virus type 1; Herpes simplex virus type 2; Varicella-zoster virus; Cytomegalovirus; Lymphogranuloma venereum; *Treponema pallidum*; *Haemophilus ducreyi*; *Candida albicans*; *Candida glabrata*; *Candida tropicalis*; *Candida parapsilosis*; *Candida krusei*; *Candida lusitaniae*; *Candida* dubliniensis; Mobiluncus *curtisii*; Mobiluncus mulieris; Group B *Streptococcus*; Human papillomavirus type 16; Human papillomavirus type 18; Human papillomavirus type 26; Human papillomavirus type 31; Human papillomavirus type 33; Human papillomavirus type 35; Human papillomavirus type 39; Human papillomavirus type 45; Human papillomavirus type 51; Human papillomavirus type 52; Human papillomavirus type 53; Human papillomavirus type 56; Human papillomavirus type 58; Human papillomavirus type 59; Human papillomavirus type 66; Human papillomavirus type 68; Human papillomavirus type 69; Human papillomavirus type 73; Human papillomavirus type 82; Human papillomavirus type 6; Human papillomavirus type 11; Human papillomavirus type 40; human papillomavirus type 42; Human papillomavirus type 43; Human papillomavirus type 44; Human papillomavirus type 54; Human papillomavirus type 61; Human papillomavirus type 70; *Mycobacterium tuberculosis; Streptococcus agalactiae; Streptococcus pyogenes; Enterococcus faecalis; Enterococcus gallinarum; Enterococcus faecium; Staphylococcus epidermidis; Staphylococcus haemolyticus; Staphylococcus aureus; Pseudomonas aeruginosa; Acinetobacter baumannii; Stenotrophomonas maltophilia; Serratia marcescens; Salmonella typhi* (*Salmonella enterica* subsp. *enterica*), *Klebsiella pneumoniae; Klebsiella oxytoca; Proteus mirabilis; Escherichia coli; Enterobacter cloacae; Enterobacter aerogenes; Aspergillus fumigatus*; Epstein-Barr virus; Enteroviruses; *Neisseria meningitides; Listeria monocytogenes*; Group B *Streptococcus* (*Streptococcus agalactiae*); Vancomycin-resistant Enterococci (VanA; VanB; VanC); Clarithomycin-resistant *Helicobacter pylori* (A2142G; A2143G); ApoE genotypes (SNP in codon112 and codon 158); Factor II (G20210A); Factor V (R506Q, H1299R, YI 702C); MTHFR (C677T, A1298C); BRAF (V600E); BCR/ABL (b2a2, b3a2, ela2, c3a2, blal, b3a3, b2a3, ela3); and *Homo sapiens*;
(b) hybridizing the target nucleic acid sequence with the TD probe; wherein the TD probe is immobilized through its 3'-end on the surface of the solid substrate; wherein the TD probe has a modified dual specificity oligonucleotide (mDSO) structure represented by the following general formula I:

5'-X'p-Y'q-Z'r-3'   (I)

wherein, X'p represents a 5'-second hybridization portion having a hybridizing nucleotide sequence complementary to the target nucleic acid sequence; Y'q represents a separation portion comprising at least three contiguous universal bases, Z'r represents a 3'-first hybridization portion having a hybridizing nucleotide sequence complementary to the target nucleic acid sequence; the TD probe has a label generating a detectable signal and the label is positioned on the 5'-second hybridization portion of the TD probe; p, q and r represent the number of nucleotides; and the sugar moiety in X', Y' and Z' is deoxyribose or ribose; the Tm of the 5'-second hybridization portion is lower than that of the 3'-first hybridization portion and the separation portion has the lowest Tm in the three portions of X'p, Y'q and Z'r; the 5'-second hybridization portion is 5-11 nucleotides in length, the 3'-first hybridization portion is 15-30 nucleotides in length and the 3'-first hybridization portion is longer than the 5'-second hybridization portion; the separation portion separates the 5'-second hybridization portion from the 3'-first hybridization portion in terms of hybridization events to the target nucleic acid sequence, whereby the hybridization specificity of the TD probe are determined dually by the 5'-second hybridization portion and the 3'-first hybridization portion;
wherein the TD probe is not extended;
wherein when the TD probe is hybridized with the target nucleic acid sequence, both of the 5'-second hybridization portion and the 3'-first hybridization portion are hybridized with the target nucleic acid sequence and the 5'-second hybridization portion is digested by the enzyme having the 5' to 3' exonuclease activity;
wherein when the TD probe is hybridized with the non-target nucleic acid sequence, both the 5'-second hybridization portion and the separation portion form a single strand such that the 5'-second hybridization portion is not digested by the enzyme having the 5' to 3' exonuclease activity, whereby the TD probe allows discriminating the target nucleic acid sequence from the non-target nucleic acid sequence;
wherein the hybridization is performed under conditions such that the hybridization solely by the 5'-second hybridization portion is prevented;
wherein the universal base is selected from the group consisting of deoxyinosine, inosine, 7-deaza-2'-deoxyinosine, 2-aza-2'-deoxyinosine, 2'-OMe inosine, 2'-F inosine, deoxy 3-nitropyrrole, 3-nitropyrrole, 2'-OMe 3-nitropyrrole, 2'-F 3-nitropyrrole, 1-(2'-deoxy-beta-D-ribofuranosyl)-3-nitropyrrole, deoxy 5-nitroindole, 5-nitroindole, 2'-OMe 5-nitroindole, 2'-F 5-nitroindole, deoxy 4-nitrobenzimidazole, 4-nitrobenzimidazole, deoxy 4-aminobenzimidazole, 4-aminobenzimidazole, deoxy nebularine, 2'-F nebularine, 2'-F 4-nitrobenzimidazole, PNA-5-introindole, PNA-nebularine, PNA-inosine, PNA-4-nitrobenzimidazole, PNA-3-nitropyrrole, morpholino-5-nitroindole, morpholinonebularine, morpholino-inosine, morpholino-4-nitrobenzimidazole, morpholino-3-nitropyrrole, phosphoramidate-5-nitroindole, phosphoramidate-nebularine, phosphoramidate-inosine, phosphoramidate-4-nitrobenzimidazole, phosphoramidate-3-nitropyrrole, 2'-O-methoxyethyl inosine, 2'0-methoxyethyl nebularine, 2'-O-methoxyethyl 5-nitroindole, 2'-O-methoxyethyl 4-nitro-benzimidazole, 2'-O-methoxyethyl 3-nitropyrrole, and combinations thereof;
(c) contacting the resultant of step (b) to the enzyme having the 5' to 3' exonuclease activity; wherein when the TD probe is hybridized with the target nucleic acid sequence, its 5'-second hybridization portion is digested by the enzyme having the 5' to 3' exonuclease activity to release the label from the TD probe, resulting in a signal change on the TD probe immobilized on the solid substrate; wherein when the TD probe is hybridized with the non-target nucleic acid sequence, the 5'-second hybridization portion is not digested by the enzyme having the 5' to 3' exonuclease activity, resulting in no signal change on the TD probe immobilized on the solid substrate; whereby the signal change on the solid substrate is detected to determine the presence of the target nucleic acid sequence; and
(d) detecting the signal change on the solid substrate, such that the signal change by the digestion on the 5'-second hybridization portion is indicative of the presence of the target nucleic acid sequence.

11. The method of claim 10, wherein the label is a fluorescent reporter molecule and the signal change is the decrease or elimination of fluorescent signals on the solid substrate.

12. The method of claim 10, wherein the label is the interactive label system comprising a pair of a fluorescent reporter molecule and a quencher molecule and the TD probe has one of the reporter molecule and the quencher molecule at a site on the 5'-second hybridization portion to be digested by the enzyme having the 5' to 3' exonuclease activity and the other on a site not to be digested by the enzyme having the 5' to 3' exonuclease activity.

13. The method of claim 12, wherein the quencher molecule is positioned at a site on the 5'-second hybridization portion of the TD probe to be digested by the enzyme having the 5' to 3' exonuclease activity and the fluorescent reporter molecule is positioned on a site not to be digested by the enzyme having the 5' to 3' exonuclease activity; wherein when the TD probe is hybridized with the target nucleic acid sequence, its 5'-second hybridization portion is digested by the enzyme having the 5' to 3' exonuclease activity to separate the fluorescent reporter molecule from the quencher molecule on the TD probe, resulting in generation of a fluorescence signal; wherein when the TD probe is hybridized with the non-target nucleic acid sequence, the 5'-second hybridization portion is not digested by the enzyme having the 5' to 3' exonuclease activity, resulting in no fluorescence signal; whereby the fluorescent signal on the solid substrate is detected to determine the presence of the target nucleic acid sequence.

14. The method of claim 10, wherein the method further comprises repeating the steps (b)-(c) or (b)-(d) with denaturation between repeating cycles.

15. The method of claim 10, wherein the target nucleic acid sequence comprises at least two types of nucleic acid sequences and the TD probe comprises at least two types of probes.

16. The method of claim 10, wherein the target nucleic acid sequence comprises a nucleotide variation and the nucleotide variation on the target nucleic acid sequence is present at a site opposite to the 5'-second hybridization portion of the TD probe.

17. The method of claim 10, wherein the TD probe has a blocker site containing as a blocker at least one nucleotide resistant to cleavage by the enzyme having 5' to 3' exonuclease activity and the blocker site is positioned at the 3'-first hybridization portion of the TD probe.

18. The method of claim 10, wherein the target nucleic acid sequence is selected from Previously Known Nucleic Acid Sequences, wherein said Previously Known Nucleic Acid Sequences are those nucleic acid sequences publicly available as of Sep. 3, 2009.

19. A method for detecting a target nucleic acid sequence from a DNA or a mixture of nucleic acids in a sample using a target discriminative probe (TD probe) and a polymerase chain reaction (PCR), which comprises the steps of:

(a) preparing a PCR mixture containing (i) the target nucleic acid sequence, (ii) the TD probe having a hybridizing nucleotide sequence complementary to the target nucleic acid sequence, (iii) a primer pair composed of two primers as an forward primer and a reverse primer each having a hybridizing nucleotide sequence complementary to the target nucleic acid sequence, and (iv) a template-dependent nucleic acid polymerase having a 5' to 3' exonuclease activity; wherein the TD probe is hybridized with a site between a hybridized site of the forward primer and a complementary site of a hybridized site of a reverse primer; wherein the TD probe has a modified dual specificity oligonucleotide (mDSO) structure represented by the following general formula I:

wherein, X'p represents a 5'-second hybridization portion having a hybridizing nucleotide sequence complementary to the target nucleic acid sequence; Y'q represents a separation portion comprising at least three contiguous universal bases, Z'r represents a 3'-first hybridization portion having a hybridizing nucleotide sequence complementary to the target nucleic acid sequence; the TD probe is dually labeled with a fluorescent reporter molecule and a quencher molecule capable of quenching the fluorescence of the reporter molecule; the fluorescent reporter molecule and the quencher molecule all are positioned on the 5'-second hybridization portion, or the reporter molecule and the quencher molecule each is positioned on each different portion of the 5'-second hybridization portion and the separation portion; p, q and r represent the number of nucleotides; and the sugar moiety in X', Y' and Z' is deoxyribose or ribose; the Tm of the 5'-second hybridization portion is lower than that of the 3'-first hybridization portion and the separation portion has the lowest Tm in the three portions of X'p, Y'q and Z'r; the 5'-second hybridization portion is 5-11 nucleotides in length, the 3'-first hybridization portion is 15-30 nucleotides in length and the 3'-first hybridization portion is longer than the 5'-second hybridization portion; the separation portion separates the 5'-second hybridization portion from the 3'-first hybridization portion in terms of hybridization events to the target nucleic acid sequence, whereby the hybridization specificity of the TD probe are determined dually by the 5'-second hybridization portion and the 3'-first hybridization portion;

wherein the TD probe is not extended;

wherein when the TD probe is hybridized with the target nucleic acid sequence, both of the 5'-second hybridization portion and the 3'-first hybridization portion are hybridized with the target nucleic acid sequence and the 5'-second hybridization portion is digested by the 5' to 3' exonuclease activity of the template-dependent nucleic acid polymerase;

wherein when the TD probe is hybridized with the non-target nucleic acid sequence, both the 5'-second hybridization portion and the separation portion form a single strand such that the 5'-second hybridization portion is not digested by the 5' to 3' exonuclease activity of the template-dependent nucleic acid polymerase, whereby the TD probe allows discriminating the target nucleic acid sequence from the non-target nucleic acid sequence;

wherein the target nucleic acid sequence is derived from any one selected from the group consisting of Influenza A virus; Influenza B virus; Respiratory syncytial virus A; Respiratory syncytial virus B; Adenovirus; Enterovirus; Parainfluenza virus 1; Parainfluenza virus 2; Parainfluenza virus 3; Parainfluenza virus 4; Metapneumovirus; Bocavirus; Rhinovirus; Coronavirus NL63; Coronavirus 229E; Coronavirus OC43; *Mycoplasma pneumoniae; Chlamydophila pneumoniae; Legionella pneumophila; Haemophilus influenza; Streptococcus pneumoniae; Bordetella pertussis; Bordetella parapertussis*; Norovirus GI; Norovirus GII; Rotavirus; Astrovirus; Sapovirus; *Campylobacter* spp.; *Clostridium difficile* (toxin B); *Salmonella* spp.; *Shigella* spp.; *Vibrio* spp.; *Yersinia enterocolitica; Aeromonas* spp.; *Clostridium difficile* (hypervirulent); *E. coli* 0157; Enterohemorrhagic *E. coli*; Enteropathogenic *E. coli*; Enterotoxigenic *E. coli*; Enteroaggregative *E. coli; Giardia lamblia; Entamoeba histolytica; Cryptosporidium* spp.; *Blastocystis hominis; Dientamoeba fragilis; Cyclospora cayetanensis; Clostridium perfringens*; Verocytotoxin-producing *E. coli* (VTEC); *Atopobium vaginae; Lactobacillus* spp.; *Bacteroides* fragilis; Megasphaera type I; Bacterial vaginosis-associated bacteria 2 (BV AB2); Mobiluncus spp.; Chlamydia trachomatis; Neisseria gonorrhoeae; Mycoplasma genitalium; Mycoplasma hominis; Trichomonas vaginalis; Ureaplasma urealyticum; Ureaplasma parvum; Herpes simplex virus type I; Herpes simplex virus type 2; Varicella-zoster virus; Cytomegalovirus; Lymphogranuloma venereum; Treponema pallidum; Haemophilus ducreyi; Candida albicans; Candida glabrata; Candida tropicalis; Candida parapsilosis; Candida krusei; Candida lusitaniae; Candida dubliniensis; Mobiluncus curtisii; Mobiluncus mulieris; Group B Streptococcus; Human papillomavirus type 16; Human papillomavirus type 18; Human papillomavirus type 26; Human papillomavirus type 31; Human papillomavirus type 33; Human papillomavirus type 35; Human papillomavirus type 39; Human papillomavirus type 45; Human papillomavirus type 51; Human papillomavirus type 52; Human papillomavirus type 53; Human papillomavirus type 56; Human papillomavirus type 58; Human papillomavirus type 59; Human papillomavirus type 66; Human papillomavirus type 68; Human papillomavirus type 69; Human papillomavirus type 73; Human papillomavirus type 82; Human papillomavirus type 6; Human papillomavirus type 11; Human papillomavirus type 40; human papillomavirus type 42; Human papillomavirus type 43; Human papillomavirus type 44; Human papillomavirus type 54; Human papillomavirus type 61; Human papillomavirus type 70; Mycobacterium tuberculosis; Streptococcus agalactiae; Streptococcus pyogenes; Enterococcus faecalis; Enterococcus gallinarum; Enterococcus faecium; Staphylococcus epidermidis; Staphylococcus haemolyticus; Staphylococcus aureus; Pseudomonas aeruginosa; Acinetobacter baumannii; Stenotrophomonas maltophilia; Serratia marcescens; Salmonella typhi (Salmonella enterica subsp. enterica), Klebsiella pneumoniae; Klebsiella oxytoca; Proteus mirabilis; Escherichia coli; Enterobacter cloacae; Enterobacter aerogenes; Aspergillus fumigatus; Epstein-Barr virus; Enteroviruses; Neisseria meningitides; Listeria monocytogenes; Group B Streptococcus (Streptococcus agalactiae); Vancomycin-resistant Enterococci (VanA; VanB; VanC); Clarithomycin-resistant Helicobacter pylori (A2142G; A2143G); ApoE genotypes (SNP in codon112 and codon158); Factor II (G20210A); Factor V (R506Q, H1299R, YI 702C); MTHFR (C677T, A1298C); BRAF (V600E); BCR/ABL (b2a2, b3a2, ela2, c3a2, blal, b3a3, b2a3, ela3); and Homo sapiens; wherein the universal base is selected from the group consisting of deoxyinosine, inosine, 7-deaza-2'-deoxyinosine, 2-aza-2'-deoxyinosine, 2'-OMe inosine, 2'-F inosine, deoxy 3-nitropyrrole, 3-nitropyrrole, 2'-OMe 3-nitropyrrole, 2'-F 3-nitropyrrole, 1-(2'-deoxy-beta-D-ribofuranosyl)-3-nitropyrrole, deoxy 5-nitroindole, 5-nitroindole, 2'-OMe 5-nitroindole, 2'-F 5-nitroindole, deoxy 4-nitrobenzimidazole, 4-nitrobenzimidazole, deoxy 4-aminobenzimidazole, 4-aminobenzimidazole, deoxy nebularine, 2'-F nebularine, 2'-F 4-nitrobenzimidazole, PNA-5-introindole, PNA-nebularine, PNA-inosine, PNA-4-nitrobenzimidazole, PNA-3-nitropyrrole, morpholino-5-nitroindole, morpholinonebularine, morpholino-inosine, morpholino-4-nitrobenzimidazole, morpholino-3-nitropyrrole, phosphoramidate-5-nitroindole, phosphoramidate-nebularine, phosphoramidate-inosine, phosphoramidate-4-nitrobenzimidazole, phosphoramidate-3-nitropyrrole, 2'-O-methoxyethyl inosine, 2'0-methoxyethyl nebularine, 2'-O-methoxyethyl 5-nitroindole, 2'-O-methoxyethyl 4-nitro-benzimidazole, 2'-O-methoxyethyl 3-nitropyrrole, and combinations thereof;

(b) amplifying the target nucleic acid sequence using the PCR mixture by performing at least two cycles of primer annealing, primer extending and denaturing, wherein the two primers are extended by a polymerase activity of the template-dependent nucleic acid polymerase to amplify the target nucleic acid sequence; wherein when the TD probe is hybridized with the target nucleic acid sequence, the 5'-second hybridization portion is digested by the 5' to 3' exonuclease activity of the template-dependent nucleic acid polymerase to separate the fluorescent reporter molecule from the quencher molecule on the TD probe, resulting in generation of a fluorescence signal; wherein when the TD probe is hybridized with the non-target nucleic acid sequence, the 5'-second hybridization portion is not digested by the 5' to 3' exonuclease activity of the template-dependent nucleic acid polymerase such that the fluorescent reporter molecule is not separated from the quencher molecule on the TD probe, resulting in no fluorescence signal;

wherein the hybridization is performed under conditions such that the hybridization solely by the 5'-second hybridization portion is prevented;

(c) detecting the fluorescence signal, such that the fluorescence signal generated is indicative of the presence of the target nucleic acid sequence.

20. The method of claim 19, wherein the target nucleic acid sequence comprises at least two types of nucleic acid sequences, the TD probe comprises at least two types of probes, the forward primer comprises at least two types of primers and the reverse primer comprises at least two types of primers.

21. The method of claim 19, wherein the target nucleic acid sequence comprises a nucleotide variation and the nucleotide variation on the target nucleic acid sequence is present at a site opposite to the 5'-second hybridization portion of the TD probe.

22. The method of claim 19, wherein the target nucleic acid sequence is selected from Previously Known Nucleic Acid Sequences, wherein said Previously Known Nucleic Acid Sequences are those nucleic acid sequences publicly available as of Sep. 3, 2009.

23. A method for detecting a target nucleic acid sequence from a DNA or a mixture of nucleic acids in a sample using a target discriminative probe (TD probe) by a ligation reaction, which comprises the steps of:

(a) preparing a reaction mixture containing a first probe having a hybridizing nucleotide sequence complementary to a first site of the target nucleic acid sequence and a second probe having a hybridizing nucleotide sequence complementary to a second site of the target nucleic acid sequence which is positioned upstream of the first site wherein the target nucleic acid sequence is derived from any one selected from the group consisting of Influenza A virus; Influenza B virus; Respiratory syncytial virus A; Respiratory syncytial virus B; Adenovirus; Enterovirus; Parainfluenza virus 1; Parainfluenza virus 2; Parainfluenza virus 3; Parainfluenza virus 4; Metapneumovirus; Bocavirus; Rhinovirus; Coronavirus NL63; Coronavirus 229E; Coronavirus OC43; Mycoplasma pneumoniae; Chlamydophila pneumoniae; Legionella pneumophila; Haemophilus influenza; Streptococcus pneumoniae; Bordetella pertussis; Bordetella parapertussis; Norovirus GI; Norovirus GII; Rotavirus; Adenovirus; Astrovirus; Sapovirus; Campylobacter spp.; Clostridium difficile (toxin B); Salmonella spp.; Shigella spp.; Vibrio spp.; Yersinia enterocolitica; Aeromonas spp.; Clostridium difficile (hypervirulent); E. coli 0157; Enterohemorrhagic E. coli; Enteropathogenic E. coli; Enterotoxigenic E. coli; Enteroaggregative E. coli; Giardia lamblia; Entamoeba histolytica; Cryptosporidium spp.; Blastocystis hominis; Dientamoeba fragilis; Cyclospora cayetanensis; Clostridium perfringens; Verocytotoxin-producing E. coli (VTEC); Atopobium vaginae; Lactobacillus spp.; Bacteroides fragilis; Megasphaera type 1; Bacterial vaginosis-associated bacteria 2 (BV AB2); Mobiluncus spp.; Chlamydia trachomatis; Neisseria gonorrhoeae; Mycoplasma genitalium; Mycoplasma hominis; Trichomonas vaginalis; Ureaplasma urealyticum; Ureaplasma parvum; Herpes simplex virus type I; Herpes simplex virus type 2; Varicella-zoster virus; Cytomegalovirus; Lymphogranuloma venereum; Treponema pallidum; Haemophilus ducreyi; Candida albicans; Candida glabrata; Candida tropicalis; Candida parapsilosis; Candida krusei; Candida lusitaniae; Candida dubliniensis; Mobiluncus curtisii; Mobiluncus mulieris; Group B Streptococcus; Human papillomavirus type 16; Human papillomavirus type 18; Human papillomavirus type 26; Human papillomavirus type 31; Human papillomavirus type 33; Human papillomavirus type 35; Human papillomavirus type 39; Human papillomavirus type 45; Human papillomavirus type 51; Human papillomavirus type 52; Human papillomavirus type 53; Human papillomavirus type 56; Human papillomavirus type 58; Human papillomavirus type 59; Human papillomavirus type 66; Human papillomavirus type 68; Human papillomavirus type 69; Human papillomavirus type 73; Human papillomavirus type 82; Human papillomavirus type 6; Human papillomavirus type 11; Human papillomavirus type 40; human papillomavirus type 42; Human papillomavirus type 43; Human papillomavirus type 44; Human papillomavirus type 54; Human papillomavirus type 61; Human papillomavirus type 70; Mycobacterium tuberculosis; Streptococcus agalactiae; Streptococcus pyogenes; Enterococcus faecalis; Enterococcus gallinarum; Enterococcus faecium; Staphylococcus epidermidis; Staphylococcus haemolyticus; Staphylococcus aureus; Pseudomonas aeruginosa; Acinetobacter baumannii; Stenotrophomonas maltophilia; Serratia marcescens; Salmonella typhi (Salmonella enterica subsp. enterica), Klebsiella pneumoniae; Klebsiella oxytoca; Proteus mirabilis; Escherichia coli; Enterobacter cloacae; Enterobacter aerogenes; Aspergillus fumigatus; Epstein-Barr virus; Enteroviruses; Neisseria meningitides; Listeria monocyotogenes; Group B Streptococcus (Streptococcus agalactiae); Vancomycin-resistant Enterococci (VanA; VanB; VanC); Clarithromycin-resistant Helicobacter pylori (A2142G; A2143G); ApoE genotypes (SNP in codon112 and codon158); Factor II (G20210A); Factor V (R506Q, H1299R, YI 702C); MTHFR (C677T, A1298C); BRAF (V600E); BCR/ABL (b2a2, b3a2, ela2, c3a2, blal, b3a3, b2a3, ela3); and Homo sapiens;
(b) hybridizing the target nucleic acid sequence with the first probe and the second probe;
wherein at least one of the first probe and the second probe has a label to generate a detectable signal; wherein the second probe is a TD probe; wherein the TD probe has a modified dual specificity oligonucleotide (mDSO) structure represented by the following general formula I:

$$5'\text{-}X'p\text{-}Y'q\text{-}Z'r\text{-}3' \qquad (I)$$

wherein, X'p represents a 5'-second hybridization portion having a hybridizing nucleotide sequence complementary to the target nucleic acid sequence; Y'q represents a separation portion comprising at least three contiguous universal bases, Z'r represents a 3'-first hybridization portion having a hybridizing nucleotide sequence complementary to the target nucleic acid sequence; the label is positioned on the 5'-second hybridization portion or the separation portion; p, q and r represent the number of nucleotides; and the sugar moiety in X', Y' and Z' is deoxyribose or ribose; the Tm of the 5'-second hybridization portion is lower than that of the 3'-first hybridization portion and the separation portion has the lowest Tm in the three portions of X'p, Y'q and Z'r; the 5'-second hybridization portion is 5-11 nucleotides in length, the 3'-first hybridization portion is 15-30 nucleotides in length and the 3'-first hybridization portion is longer than the 5'-second hybridization portion; the separation portion separates the 5'-second hybridization portion from the 3'-first hybridization portion in terms of hybridization events to the target nucleic acid sequence, whereby the hybridization specificity of the TD probe are determined dually by the 5'-second hybridization portion and the 3'-first hybridization portion;

wherein the second probe is not extended;

wherein when the second probe is hybridized with the target nucleic acid sequence, both of the 5'-second hybridization portion and the 3'-first hybridization portion of the second probe are hybridized with the target nucleic acid sequence to allow ligation of the first probe and the second probe; wherein when the second probe is hybridized with the nontarget nucleic acid sequence, both of the 5'-second hybridization portion and the separation portion of the second probe form a single strand such that the first probe and the second probe are not ligated, whereby the second probe allows discriminating the target nucleic acid sequence from the nontarget nucleic acid sequence;

wherein the universal base is selected from the group consisting of deoxyinosine, inosine, 7-deaza-2'-deoxyinosine, 2-aza-2'-deoxyinosine, 2'-OMe inosine, 2'-F inosine, deoxy 3-nitropyrrole, 3-nitropyrrole, 2'-OMe 3-nitropyrrole, 2'-F 3-nitropyrrole, 1-(2'-deoxy-beta-D-ribofuranosyl)-3-nitropyrrole, deoxy 5-nitroindole, 5-nitroindole, 2'-OMe 5-nitroindole, 2'-F 5-nitroindole, deoxy 4-nitrobenzimidazole, 4-nitrobenzimidazole, deoxy 4-aminobenzimidazole, 4-aminobenzimidazole, deoxy nebularine, 2'-F nebularine, 2'-F 4-nitrobenzimidazole, PNA-5-introindole, PNA-nebularine, PNA-inosine, PNA-4-nitrobenzimidazole, PNA-3-nitropyrrole, morpholino-5-nitroindole, morpholinonebularine, morpholino-inosine, morpholino-4-nitrobenzimidazole, morpholino-3-nitropyrrole, phosphoramidate-5-nitroindole, phosphoramidate-nebularine, phosphoramidate-inosine, phosphoramidate-4-nitrobenzimidazole, phosphoramidate-3-nitropyrrole, 2'-O-methoxyethyl inosine, 2'0-methoxyethyl nebularine, 2'-O-methoxyethyl 5-nitroindole, 2'-O-methoxyethyl 4-nitro-benzimidazole, 2'-O-methoxyethyl 3-nitropyrrole, and combinations thereof;
(c) ligating the first probe and the second probe hybridized with the target nucleic acid sequence such that a ligated probe is produced;
(d) denaturing the resultant of step (c);
(e) detecting the signal from the label on the ligated probe, such that the signal is indicative of the presence of the target nucleic acid sequence.

24. The method of claim 23, wherein the label is the interactive label system comprising a pair of a reporter molecule and a quencher molecule.

25. The method of claim 23, wherein the first probe has a dual specificity oligonucleotide (DSO) structure represented by the following general formula II:

5'-Xp-Yq-Zr-3'  (II)

wherein, Xp represents a 5'-first hybridization portion having a hybridizing nucleotide sequence complementary to the target nucleic acid; Yq represents a separation portion comprising at least three contiguous universal bases, Zr represents a 3'-second hybridization portion having a hybridizing nucleotide sequence complementary to the target nucleic acid; p, q and r represent the number of nucleotides, and the sugar moiety in X, Y, and Z is deoxyribose or ribose; the Tm of the 5'-first hybridization portion is higher than that of the 3'-second hybridization portion and the separation portion has the lowest Tm in the three portions; the 5'-second hybridization portion is 5-11 nucleotides in length, the 3'-first hybridization portion is 15-30 nucleotides in length and the 3'-first hybridization portion is longer than the 5'-second hybridization portion; the separation portion separates the 5'-first hybridization portion from the 3'-second hybridization portion in terms of hybridization events to the target nucleic acid, whereby the hybridization specificity of the oligonucleotide are determined dually by the 5'-first hybridization portion and the 3'-second hybridization portion;
wherein the first probe is not extended;
wherein the universal base is selected from the group consisting of deoxyinosine, inosine, 7-deaza-2'-deoxyinosine, 2-aza-2'-deoxyinosine, 2'-OMe inosine, 2'-F inosine, deoxy 3-nitropyrrole, 3-nitropyrrole, 2'-OMe 3-nitropyrrole, 2'-F 3-nitropyrrole, 1-(2'-deoxy-beta-D-ribofuranosyl)-3-nitropyrrole, deoxy 5-nitroindole, 5-nitroindole, 2'-OMe 5-nitroindole, 2'-F 5-nitroindole, deoxy 4-nitrobenzimidazole, 4-nitrobenzimidazole, deoxy 4-aminobenzimidazole, 4-aminobenzimidazole, deoxy nebularine, 2'-F nebularine, 2'-F 4-nitrobenzimidazole, PNA-5-introindole, PNA-nebularine, PNA-inosine, PNA-4-nitrobenzimidazole, PNA-3-nitropyrrole, morpholino-5-nitroindole, morpholinonebularine, morpholino-inosine, morpholino-4-nitrobenzimidazole, morpholino-3-nitropyrrole, phosphoramidate-5-nitroindole, phosphoramidate-nebularine, phosphoramidate-inosine, phosphoramidate-4-nitrobenzimidazole, phosphoramidate-3-nitropyrrole, 2'-O-methoxyethyl inosine, 2'0-methoxyethyl nebularine, 2'-O-methoxyethyl 5-nitroindole, 2'-O-methoxyethyl 4-nitro-benzimidazole, 2'-O-methoxyethyl 3-nitropyrrole, and combinations thereof.

26. The method of claim 23, wherein the method further comprises repeating the steps (b)-(d) or (b)-(e).

27. The method of claim 23, wherein the method is performed on a solid phase;
wherein the first probe is immobilized through its 5'-end on the surface of a solid substrate and the second probe is not immobilized.

28. The method of claim 23, wherein the method is performed on a solid phase;
wherein the second probe is immobilized through its 3'-end on the surface of the solid substrate and the first probe is not immobilized.

29. The method of claim 23, wherein the target nucleic acid sequence comprises at least two types of nucleic acid sequences and the first probe and the second probe each comprises at least two types of probes.

30. The method of claim 23, wherein the target nucleic acid sequence comprises a nucleotide variation and the nucleotide variation on the target nucleic acid sequence is present at a site opposite to the 5'-second hybridization portion of the TD probe.

31. The method of claim 23, wherein the target nucleic acid sequence is selected from Previously Known Nucleic Acid Sequences, wherein said Previously Known Nucleic Acid Sequences are those nucleic acid sequences publicly available as of Sep. 3, 2009.

32. A method for detecting a target nucleic acid sequence from a DNA or a mixture of nucleic acids in a sample using a target discriminative probe (TD probe), which comprises the steps of:
(a) preparing a reaction mixture containing a TD probe having a hybridizing nucleotide sequence complementary to the target nucleic acid sequence wherein the selected target nucleic acid sequence is derived from any one selected from the group consisting of Influenza A virus; Influenza B virus; Respiratory syncytial virus A; Respiratory syncytial virus B; Adenovirus; Enterovirus; Parainfluenza virus 1; Parainfluenza virus 2; Parainfluenza virus 3; Parainfluenza virus 4; Metapneumovirus; Bocavirus; Rhinovirus; Coronavirus NL63; Coronavirus 229E; Coronavirus OC43; *Mycoplasma pneumoniae; Chlamydophila pneumoniae; Legionella pneumophila; Haemophilus* influenza; *Streptococcus pneumoniae; Bordetella pertussis; Bordetella parapertussis*; Norovirus GI; Norovirus GII; Rotavirus; Astrovirus; Sapovirus; *Campylobacter* spp.; *Clostridium difficile* (toxin B); *Salmonella* spp.; *Shigella* spp.; *Vibrio* spp.; *Yersinia enterocolitica; Aeromonas* spp.; *Clostridium difficile* (hypervirulent); *E. coli* 0157; Enterohemorrhagic *E. coli*; Enteropathogenic *E. coli*; Enterotoxigenic *E. coli*; Enteroaggregative *E. coli*; *Giardia lamblia; Entamoeba histolytica; Cryptosporidium* spp.; *Blastocystis hominis; Dientamoeba fragilis; Cyclospora cayetanensis; Clostridium perfringens*; Verocytotoxin-producing *E. coli* (VTEC); Atopobium vaginae; *Lactobacillus* spp.; *Bacteroides fragilis; Megasphaera type* 1; Bacterial vaginosis-associated bacteria 2 (BV AB2); Mobiluncus spp.; *Chlamydia trachomatis; Neisseria gonorrhoeae; Mycoplasma genitalium; Mycoplasma hominis; Trichomonas vaginalis; Ureaplasma urealyticum; Ureaplasma parvum*; Herpes simplex virus type 1; Herpes simplex virus type 2; Varicella-zoster virus; Cytomegalovirus; Lymphogranuloma venereum; *Treponema pallidum; Haemophilus ducreyi; Candida albicans; Candida glabrata; Candida tropicalis; Candida parapsilosis; Candida krusei; Candida lusitaniae; Candida dubliniensis*; Mobiluncus *curtisii; Mobiluncus mulieris*; Group B *Streptococcus*; Human papillomavirus type 16; Human papillomavirus type 18; Human papillomavirus type 26; Human papillomavirus type 31; Human papillomavirus type 33; Human papillomavirus type 35; Human papillomavirus type 39; Human papillomavirus type 45; Human papillomavirus type 51; Human papillomavirus type 52; Human papillomavirus type 53; Human papillomavirus type 56; Human papillomavirus type 58; Human papillomavirus type 59; Human papillomavirus type 66; Human papillomavirus type 68; Human papillomavirus type 69; Human papillomavirus type 73; Human papillomavirus type 82; Human papillomavirus type 6; Human papillomavirus type 11; Human papillomavirus type 40; human papillomavirus type 42; Human papillomavirus type 43; Human papillomavirus type 44; Human papillomavirus type 54; Human papillomavirus type 61; Human papillomavirus type 70; *Mycobacterium tuberculosis; Streptococcus agalactiae; Streptococcus pyogenes; Enterococcus faecalis; Enterococcus gallinarum; Enterococcus faecium; Staphylococcus epidermidis; Staphylococcus haemolyticus; Staphylococcus aureus; Pseudomonas aeruginosa; Acinetobacter baumannii; Stenotrophomonas maltophilia; Serratia marcescens; Salmonella typhi (Salmonella enterica* subsp. *enterica), Klebsiella pneumoniae; Klebsiella oxytoca; Proteus mirabilis; Escherichia coli; Enterobacter cloacae; Enterobacter aerogenes; Aspergillus fumigatus*; Epstein-Barr virus; Enteroviruses; *Neisseria meningitides; Listeria monocytogenes*; Group B *Streptococcus (Streptococcus agalactiae)*; Vancomycin-resistant Enterococci (VanA; VanB; VanC); Clarithomycin-resistant *Helicobacter pylori* (A2142G; A2143G); ApoE genotypes (SNP in codon112 and codon158); Factor II (G20210A); Factor V (R506Q, H1299R, YI 702C); MTHFR (C677T, A1298C); BRAF (V600E); BCR/ABL (b2a2, b3a2, ela2, c3a2, blal, b3a3, b2a3, ela3); and *Homo sapiens;*
(b) hybridizing the target nucleic acid sequence with the TD probe; wherein the TD probe has a modified dual specificity oligonucleotide (mDSO) structure represented by the following general formula I:

5'-X'p-Y'q-Z'r-3' (I)

wherein, X'p represents a 5'-second hybridization portion having a hybridizing nucleotide sequence complementary to the target nucleic acid sequence; Y'q represents a separation portion comprising at least three contiguous universal bases, Z'r represents a 3'-first hybridization portion having a hybridizing nucleotide sequence complementary to the target nucleic acid sequence; the TD probe is labeled with a fluorescent reporter molecule on the 5'-second hybridization portion; the fluorescent reporter molecule generates different fluorescent intensity depending on whether it is in single-strand or double-strand; p, q and r represent the number of nucleotides; and the sugar moiety in X', Y' and Z' is deoxyribose or ribose; the Tm of the 5'-second hybridization portion is lower than that of the 3'-first hybridization portion and the separation portion has the lowest Tm in the three portions of X'p, Y'q and Z'r; the 5'-second hybridization portion is 5-11 nucleotides in length, the 3'-first hybridization portion is 15-30 nucleotides in length and the 3'-first hybridization portion is longer than the 5'-second hybridization portion; the separation portion separates the 5'-second hybridization portion from the 3'-first hybridization portion in terms of hybridization events to the target nucleic acid sequence, whereby the hybridization specificity of the TD probe is determined dually by the 5'-second hybridization portion and the 3'-first hybridization portion;

wherein the TD probe is not extended;

wherein when the TD probe is hybridized with the target nucleic acid sequence, both of the 5'-second hybridization portion and the 3'-first hybridization portion are hybridized with the target nucleic acid sequence to render the fluorescent reporter molecule in double-strand, thereby inducing a change in fluorescence from the fluorescent reporter molecule; wherein when the TD probe is hybridized with the non-target nucleic acid sequence, both the 5'-second hybridization portion and the separation portion form a single strand to induce no change in fluorescence from the fluorescent reporter molecule, whereby the TD probe allows discriminating the target nucleic acid sequence from the non-target nucleic acid sequence;

wherein the hybridization is performed under conditions such that the hybridization solely by the 5'-second hybridization portion is prevented;

wherein the universal base is selected from the group consisting of deoxyinosine, inosine, 7-deaza-2'-deoxyinosine, 2-aza-2'-deoxyinosine, 2'-OMe inosine, 2'-F inosine, deoxy 3-nitropyrrole, 3-nitropyrrole, 2'-OMe 3-nitropyrrole, 2'-F 3-nitropyrrole, 1-(2'-deoxy-beta-D-ribofuranosyl)-3-nitropyrrole, deoxy 5-nitroindole, 5-nitroindole, 2'-OMe 5-nitroindole, 2'-F 5-nitroindole, deoxy 4-nitrobenzimidazole, 4-nitrobenzimidazole, deoxy-4-aminobenzimidazole, 4-aminobenzimidazole, deoxy nebularine, 2'-F nebularine, 2'-F 4-nitrobenzimidazole, PNA-5-introindole, PNA-nebularine, PNA-inosine, PNA-4-nitrobenzimidazole, PNA-3-nitropyrrole, morpholino-5-nitroindole, morpholinonebularine, morpholino-inosine, morpholino-4-nitrobenzimidazole, morpholino-3-nitropyrrole, phosphoramidate-5-nitroindole, phosphoramidate-nebularine, phosphoramidate-inosine, phosphoramidate-4-nitrobenzimidazole, phosphoramidate-3-nitropyrrole, 2'-O-methoxyethyl inosine, 2'0-methoxyethyl nebularine, 2'-O-methoxyethyl 5-nitroindole, 2'-O-methoxyethyl 4-nitro-benzimidazole, 2'-O-methoxyethyl 3-nitropyrrole, and combinations thereof; and (c) detecting the fluorescence change, such that the fluorescence change is indicative of the presence of the target nucleic acid sequence.

33. The method of claim 32, wherein the step (b) is carried out using the TD probe together with a reverse primer and a template-dependent nucleic acid polymerase such that the target nucleic acid sequence hybridizable with the TD probe is additionally generated to enhance the fluorescence change indicative of the presence of the target nucleic acid sequence.

34. The method of claim 32, wherein the step (b) is carried out using the TD probe together with a primer pair composed of two primers as a forward primer and a reverse primer and a template-dependent nucleic acid polymerase such that the target nucleic acid sequence hybridizable with the TD probe is amplified by PCR to enhance the fluorescence change indicative of the presence of the target nucleic acid sequence.

35. The method of claim 32, wherein the TD probe is additionally labeled with a quencher molecule capable of quenching the fluorescence of the reporter molecule.

* * * * *

SEQUENCE LISTING

<160> NUMBER OF SEQ ID NOS: 39

<210> SEQ ID NO 1
<211> LENGTH: 70
<212> TYPE: DNA
<213> ORGANISM: Artificial Sequence
<220> FEATURE:
<223> OTHER INFORMATION: SA_T70 Probe

<400> SEQUENCE: 1
ggtgtaggtg gtggcggtaa caacgccgta aaccgaatga ttgaccacgg aatgaataat     60
gttgaattta                                                           70

<210> SEQ ID NO 2
<211> LENGTH: 24
<212> TYPE: DNA
<213> ORGANISM: Artificial Sequence
<220> FEATURE:
<223> OTHER INFORMATION: SA_P0 Probe

<400> SEQUENCE: 2
cattcggttt acggcgttgt tacc                                            24

<210> SEQ ID NO 3
<211> LENGTH: 25

```
<212> TYPE: DNA
<213> ORGANISM: Artificial Sequence
<220> FEATURE:
<223> OTHER INFORMATION: SA_P1 Probe

<400> SEQUENCE: 3
ccattcggtt tacggcgttg ttacc                                    25

<210> SEQ ID NO 4
<211> LENGTH: 27
<212> TYPE: DNA
<213> ORGANISM: Artificial Sequence
<220> FEATURE:
<223> OTHER INFORMATION: SA_P3 Probe

<400> SEQUENCE: 4
tgccattcgg tttacggcgt tgttacc                                  27

<210> SEQ ID NO 5
<211> LENGTH: 30
<212> TYPE: DNA
<213> ORGANISM: Artificial Sequence
<220> FEATURE:
<223> OTHER INFORMATION: SA_P6 Probe

<400> SEQUENCE: 5
acttgccatt cggtttacgg cgttgttacc                               30

<210> SEQ ID NO 6
<211> LENGTH: 33
<212> TYPE: DNA
<213> ORGANISM: Artificial Sequence
<220> FEATURE:
<223> OTHER INFORMATION: SA_P9 Probe

<400> SEQUENCE: 6
acaacttgcc attcggttta cggcgttgtt acc                           33

<210> SEQ ID NO 7
<211> LENGTH: 39
<212> TYPE: DNA
<213> ORGANISM: Artificial Sequence
<220> FEATURE:
<223> OTHER INFORMATION: SA_TD_M Probe
<220> FEATURE:
<221> NAME/KEY: misc_feature
<222> LOCATION: (11)..(15)
<223> OTHER INFORMATION: n denotes deoxyinosine

<400> SEQUENCE: 7
cattccgtgg nnnnncattc ggtttacggc gttgttacc                     39

<210> SEQ ID NO 8
<211> LENGTH: 39
<212> TYPE: DNA
<213> ORGANISM: Artificial Sequence
<220> FEATURE:
<223> OTHER INFORMATION: SA_TD_m Probe
<220> FEATURE:
<221> NAME/KEY: misc_feature
<222> LOCATION: (11)..(15)
<223> OTHER INFORMATION: n denotes deoxyinosine

<400> SEQUENCE: 8
tgccttataa nnnnncattc ggtttacggc gttgttacc                     39

<210> SEQ ID NO 9
```

```
<211> LENGTH: 100
<212> TYPE: DNA
<213> ORGANISM: Artificial Sequence
<220> FEATURE:
<223> OTHER INFORMATION: NG_T100 Probe

<400> SEQUENCE: 9
gaaattatgc ccttaaatat gcgaaacacg ccaatgaggg gcatgatgct ttcttttgt      60 tcttgctcgg cagagcgagt gataccgatc cattgaaaaa                         100

<210> SEQ ID NO 10
<211> LENGTH: 39
<212> TYPE: DNA
<213> ORGANISM: Artificial Sequence
<220> FEATURE:
<223> OTHER INFORMATION: NG_TD_M Probe
<220> FEATURE:
<221> NAME/KEY: misc_feature
<222> LOCATION: (11)..(15)
<223> OTHER INFORMATION: n denotes deoxyinosine

<400> SEQUENCE: 10
agcatcatgc nnnnnattgg cgtgtttcgc atatttaag                          39

<210> SEQ ID NO 11
<211> LENGTH: 39
<212> TYPE: DNA
<213> ORGANISM: Artificial Sequence
<220> FEATURE:
<223> OTHER INFORMATION: NG_TD_m Probe
<220> FEATURE:
<221> NAME/KEY: misc_feature
<222> LOCATION: (11)..(15)
<223> OTHER INFORMATION: n denotes deoxyinosine

<400> SEQUENCE: 11
gatgctgtat nnnnnattgg cgtgtttcgc atatttaag                          39

<210> SEQ ID NO 12
<211> LENGTH: 39
<212> TYPE: DNA
<213> ORGANISM: Artificial Sequence
<220> FEATURE:
<223> OTHER INFORMATION: SA_TD_m1 Probe
<220> FEATURE:
<221> NAME/KEY: misc_feature
<222> LOCATION: (11)..(15)
<223> OTHER INFORMATION: n denotes deoxyinosine

<400> SEQUENCE: 12
cacctcgtgg nnnnncattc ggtttacggc gttgttacc                          39

<210> SEQ ID NO 13
<211> LENGTH: 39
<212> TYPE: DNA
<213> ORGANISM: Artificial Sequence
<220> FEATURE:
<223> OTHER INFORMATION: SA_Con_M Probe

<400> SEQUENCE: 13
cattccgtgg tcaatcattc ggtttacggc gttgttacc                          39

<210> SEQ ID NO 14
<211> LENGTH: 39
<212> TYPE: DNA
<213> ORGANISM: Artificial Sequence
<220> FEATURE:
<223> OTHER INFORMATION: SA_Con_m1 Probe
```

<400> SEQUENCE: 14
cacctcgtgg tcaatcattc ggtttacggc gttgttacc                              39

<210> SEQ ID NO 15
<211> LENGTH: 40
<212> TYPE: DNA
<213> ORGANISM: Artificial Sequence
<220> FEATURE:
<223> OTHER INFORMATION: SA_F Probe
<220> FEATURE:
<221> NAME/KEY: misc_feature
<222> LOCATION: (26)..(30)
<223> OTHER INFORMATION: n denotes deoxyinosine

<400> SEQUENCE: 15
tgttagaatt tgaacaagga tttaannnnn tagcgactttt                             40

<210> SEQ ID NO 16
<211> LENGTH: 38
<212> TYPE: DNA
<213> ORGANISM: Artificial Sequence
<220> FEATURE:
<223> OTHER INFORMATION: SA_R Probe
<220> FEATURE:
<221> NAME/KEY: misc_feature
<222> LOCATION: (24)..(28)
<223> OTHER INFORMATION: n denotes deoxyinosine

<400> SEQUENCE: 16
gataagttta aagcttgacc gtcnnnnntg atagcgat                               38

<210> SEQ ID NO 17
<211> LENGTH: 39
<212> TYPE: DNA
<213> ORGANISM: Artificial Sequence
<220> FEATURE:
<223> OTHER INFORMATION: SA_TD2_M Probe
<220> FEATURE:
<221> NAME/KEY: misc_feature
<222> LOCATION: (11)..(15)
<223> OTHER INFORMATION: n denotes deoxyinosine

<400> SEQUENCE: 17
cattccgtgg nnnnncattc ggtttacggc gttgttacc                              39

<210> SEQ ID NO 18
<211> LENGTH: 39
<212> TYPE: DNA
<213> ORGANISM: Artificial Sequence
<220> FEATURE:
<223> OTHER INFORMATION: SA_TD2_m Probe
<220> FEATURE:
<221> NAME/KEY: misc_feature
<222> LOCATION: (11)..(15)
<223> OTHER INFORMATION: n denotes deoxyinosine

<400> SEQUENCE: 18
tgccttataa nnnnncattc ggtttacggc gttgttacc                              39

<210> SEQ ID NO 19
<211> LENGTH: 37
<212> TYPE: DNA
<213> ORGANISM: Artificial Sequence
<220> FEATURE:
<223> OTHER INFORMATION: NG_F Probe
<220> FEATURE:
<221> NAME/KEY: misc_feature
<222> LOCATION: (22)..(26)

<223> OTHER INFORMATION: n denotes deoxyinosine

<400> SEQUENCE: 19
tacgcctgct actttcacgc tnnnnngtaa tcagatg    37

<210> SEQ ID NO 20
<211> LENGTH: 37
<212> TYPE: DNA
<213> ORGANISM: Artificial Sequence
<220> FEATURE:
<223> OTHER INFORMATION: NG_R Probe
<220> FEATURE:
<221> NAME/KEY: misc_feature
<222> LOCATION: (22)..(26)
<223> OTHER INFORMATION: n denotes deoxyinosine

<400> SEQUENCE: 20
caatggatcg gtatcactcg cnnnnncgag caagaac    37

<210> SEQ ID NO 21
<211> LENGTH: 39
<212> TYPE: DNA
<213> ORGANISM: Artificial Sequence
<220> FEATURE:
<223> OTHER INFORMATION: NG_TD2_M Probe
<220> FEATURE:
<221> NAME/KEY: misc_feature
<222> LOCATION: (11)..(15)
<223> OTHER INFORMATION: n denotes deoxyinosine

<400> SEQUENCE: 21
agcatcatgc nnnnnattgg cgtgtttcgc atatttaag    39

<210> SEQ ID NO 22
<211> LENGTH: 39
<212> TYPE: DNA
<213> ORGANISM: Artificial Sequence
<220> FEATURE:
<223> OTHER INFORMATION: NG_TD2_m Probe
<220> FEATURE:
<221> NAME/KEY: misc_feature
<222> LOCATION: (11)..(15)
<223> OTHER INFORMATION: n denotes deoxyinosine

<400> SEQUENCE: 22
gatgctgtat nnnnnattgg cgtgtttcgc atatttaag    39

<210> SEQ ID NO 23
<211> LENGTH: 37
<212> TYPE: DNA
<213> ORGANISM: Artificial Sequence
<220> FEATURE:
<223> OTHER INFORMATION: SA_TD_S_M Probe
<220> FEATURE:
<221> NAME/KEY: misc_feature
<222> LOCATION: (9)..(13)
<223> OTHER INFORMATION: n denotes deoxyinosine

<400> SEQUENCE: 23
ttccgtggnn nnncattcgg tttacggcgt tgttacc    37

<210> SEQ ID NO 24
<211> LENGTH: 37
<212> TYPE: DNA
<213> ORGANISM: Artificial Sequence
<220> FEATURE:
<223> OTHER INFORMATION: SA_TD_S_m Probe
<220> FEATURE:
<221> NAME/KEY: misc_feature

```
<222> LOCATION: (9)..(13)
<223> OTHER INFORMATION: n denotes deoxyinosine

<400> SEQUENCE: 24
ttctgtggnn nnncattcgg tttacggcgt tgttacc                              37

<210> SEQ ID NO 25
<211> LENGTH: 44
<212> TYPE: DNA
<213> ORGANISM: Artificial Sequence
<220> FEATURE:
<223> OTHER INFORMATION: SA_TD1_Chip_M Probe
<220> FEATURE:
<221> NAME/KEY: misc_feature
<222> LOCATION: (11)..(15)
<223> OTHER INFORMATION: n denotes deoxyinosine

<400> SEQUENCE: 25
cattccgtgg nnnnncattc ggtttacggc gttgttacct tttt                     44

<210> SEQ ID NO 26
<211> LENGTH: 44
<212> TYPE: DNA
<213> ORGANISM: Artificial Sequence
<220> FEATURE:
<223> OTHER INFORMATION: SA_TD1_Chip_m Probe
<220> FEATURE:
<221> NAME/KEY: misc_feature
<222> LOCATION: (11)..(15)
<223> OTHER INFORMATION: n denotes deoxyinosine

<400> SEQUENCE: 26
tgccttataa nnnnncattc ggtttacggc gttgttacct tttt                     44

<210> SEQ ID NO 27
<211> LENGTH: 44
<212> TYPE: DNA
<213> ORGANISM: Artificial Sequence
<220> FEATURE:
<223> OTHER INFORMATION: SA_TD1_Chip_m1 Probe
<220> FEATURE:
<221> NAME/KEY: misc_feature
<222> LOCATION: (11)..(15)
<223> OTHER INFORMATION: n denotes deoxyinosine

<400> SEQUENCE: 27
cacctcgtgg nnnnncattc ggtttacggc gttgttacct tttt                     44

<210> SEQ ID NO 28
<211> LENGTH: 44
<212> TYPE: DNA
<213> ORGANISM: Artificial Sequence
<220> FEATURE:
<223> OTHER INFORMATION: SA_Con_Chip_M Probe

<400> SEQUENCE: 28
cattccgtgg tcaatcattc ggtttacggc gttgttacct tttt                     44

<210> SEQ ID NO 29
<211> LENGTH: 44
<212> TYPE: DNA
<213> ORGANISM: Artificial Sequence
<220> FEATURE:
<223> OTHER INFORMATION: SA_Con_Chip_m1 Probe

<400> SEQUENCE: 29
cacctcgtgg tcaatcattc ggtttacggc gttgttacct tttt                     44
```

```
<210> SEQ ID NO 30
<211> LENGTH: 44
<212> TYPE: DNA
<213> ORGANISM: Artificial Sequence
<220> FEATURE:
<223> OTHER INFORMATION: SA_TD2_Chip_M Probe
<220> FEATURE:
<221> NAME/KEY: misc_feature
<222> LOCATION: (11)..(15)
<223> OTHER INFORMATION: n denotes deoxyinosine

<400> SEQUENCE: 30
cattccgtgg nnnnncattc ggtttacggc gttgttacct tttt                44

<210> SEQ ID NO 31
<211> LENGTH: 44
<212> TYPE: DNA
<213> ORGANISM: Artificial Sequence
<220> FEATURE:
<223> OTHER INFORMATION: SA_TD2_Chip_m Probe
<220> FEATURE:
<221> NAME/KEY: misc_feature
<222> LOCATION: (11)..(15)
<223> OTHER INFORMATION: n denotes deoxyinosine

<400> SEQUENCE: 31
tgccttataa nnnnncattc ggtttacggc gttgttacct tttt                44

<210> SEQ ID NO 32
<211> LENGTH: 44
<212> TYPE: DNA
<213> ORGANISM: Artificial Sequence
<220> FEATURE:
<223> OTHER INFORMATION: SA_TD2_Chip_M_2 Probe
<220> FEATURE:
<221> NAME/KEY: misc_feature
<222> LOCATION: (11)..(15)
<223> OTHER INFORMATION: n denotes deoxyinosine

<400> SEQUENCE: 32
cattccgtgg nnnnncattc ggtttacggc gttgttacct tttt                44

<210> SEQ ID NO 33
<211> LENGTH: 44
<212> TYPE: DNA
<213> ORGANISM: Artificial Sequence
<220> FEATURE:
<223> OTHER INFORMATION: SA_TD2_Chip_m_2 Probe
<220> FEATURE:
<221> NAME/KEY: misc_feature
<222> LOCATION: (11)..(15)
<223> OTHER INFORMATION: n denotes deoxyinosine

<400> SEQUENCE: 33
tgccttataa nnnnncattc ggtttacggc gttgttacct tttt                44

<210> SEQ ID NO 34
<211> LENGTH: 110
<212> TYPE: DNA
<213> ORGANISM: Artificial Sequence
<220> FEATURE:
<223> OTHER INFORMATION: SA_T110 Probe

<400> SEQUENCE: 34
tgtaggtggt ggcggtaaca acgccgtaaa ccgaatgatt gaccacggaa tgaataatgt    60
tgaatttatc gctatcaaca cagacggtca agctttaaac ttatctaaag              110
```

```
<210> SEQ ID NO 35
<211> LENGTH: 42
<212> TYPE: DNA
<213> ORGANISM: Artificial Sequence
<220> FEATURE:
<223> OTHER INFORMATION: SA_TD_Chip_S_M Probe
<220> FEATURE:
<221> NAME/KEY: misc_feature
<222> LOCATION: (9)..(13)
<223> OTHER INFORMATION: n denotes deoxyinosine

<400> SEQUENCE: 35
ttccgtggnn nnncattcgg tttacggcgt tgttaccttt tt                    42

<210> SEQ ID NO 36
<211> LENGTH: 42
<212> TYPE: DNA
<213> ORGANISM: Artificial Sequence
<220> FEATURE:
<223> OTHER INFORMATION: SA_TD_Chip_S_m Probe
<220> FEATURE:
<221> NAME/KEY: misc_feature
<222> LOCATION: (9)..(13)
<223> OTHER INFORMATION: n denotes deoxyinosine

<400> SEQUENCE: 36
ttctgtggnn nnncattcgg tttacggcgt tgttaccttt tt                    42

<210> SEQ ID NO 37
<211> LENGTH: 38
<212> TYPE: DNA
<213> ORGANISM: Artificial Sequence
<220> FEATURE:
<223> OTHER INFORMATION: SA_Chip_DSO Probe
<220> FEATURE:
<221> NAME/KEY: misc_feature
<222> LOCATION: (24)..(28)
<223> OTHER INFORMATION: n denotes deoxyinosine

<400> SEQUENCE: 37
accgtctgtg ttgatagcga taannnnnac attattca                         38

<210> SEQ ID NO 38
<211> LENGTH: 39
<212> TYPE: DNA
<213> ORGANISM: Artificial Sequence
<220> FEATURE:
<223> OTHER INFORMATION: SA_TD3_M Probe
<220> FEATURE:
<221> NAME/KEY: misc_feature
<222> LOCATION: (11)..(15)
<223> OTHER INFORMATION: n denotes deoxyinosine

<400> SEQUENCE: 38
cattccgtgg nnnnncattc ggtttacggc gttgttacc                        39

<210> SEQ ID NO 39
<211> LENGTH: 39
<212> TYPE: DNA
<213> ORGANISM: Artificial Sequence
<220> FEATURE:
<223> OTHER INFORMATION: SA_TD3_m Probe
<220> FEATURE:
<221> NAME/KEY: misc_feature
<222> LOCATION: (11)..(15)
<223> OTHER INFORMATION: n denotes deoxyinosine

<400> SEQUENCE: 39
tgccttataa nnnnncattc ggtttacggc gttgttacc                        39
```